US006630680B2

(12) United States Patent
Hakamata et al.

(10) Patent No.: US 6,630,680 B2
(45) Date of Patent: Oct. 7, 2003

(54) SCANNER HAVING CONFOCAL OPTICAL SYSTEM, METHOD FOR PRODUCING FOCUS POSITION DATA OF CONFOCAL OPTICAL SYSTEM OF SCANNER HAVING CONFOCAL OPTICAL SYSTEM AND METHOD FOR PRODUCING DIGITAL DATA OF SCANNER HAVING CONFOCAL OPTICAL SYSTEM

(75) Inventors: Masashi Hakamata, Kanagawa (JP); Takashi Kobayashi, Kanagawa (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 91 days.

(21) Appl. No.: 10/020,137

(22) Filed: Dec. 18, 2001

(65) Prior Publication Data

US 2002/0117632 A1 Aug. 29, 2002

(30) Foreign Application Priority Data

Dec. 25, 2000  (JP) ...................... 2000-392072

(51) Int. Cl.[7] .............................................. G01N 21/64
(52) U.S. Cl. .................................. 250/458.1; 250/201.2
(58) Field of Search .......................... 250/201.2, 458.1, 250/459.1

(56) References Cited

U.S. PATENT DOCUMENTS

| | | | | |
|---|---|---|---|---|
| 5,578,832 A | * | 11/1996 | Trulson et al. | 250/458.1 |
| 5,834,785 A | * | 11/1998 | Coon | 250/492.2 |
| 6,134,002 A | * | 10/2000 | Stimson et al. | 250/459.1 |
| 6,462,345 B1 | * | 10/2002 | Simon et al. | 250/458.1 |
| 6,507,009 B1 | * | 1/2003 | Ohnishi et al. | 250/201.2 |
| 6,522,441 B1 | * | 2/2003 | Rudeen | 250/201.2 |

* cited by examiner

Primary Examiner—G. Bradley Bennett
(74) Attorney, Agent, or Firm—Sughrue Mion, PLLC

(57) ABSTRACT

A scanner includes laser stimulating ray sources, a motor for an objective lens incorporated in a confocal optical system and a controller adapted to produce position data by placing a sample carrier in which five distance measuring devices are set on a sample stage, and measuring a distance between the objective lens and a reference position on the distance measuring devices and a distance between the objective lens and measurement positions on the distance measuring devices, to produce focus position data produced by setting a luminescent material included in a focus position determination device at the reference position, scanning the focus position determination device with the laser beam, detecting fluorescence emission, and changing the position of the objective lens with a predetermined pitch, and to cause the motor to adjust the position of the objective lens based on the focus position data corrected with the position data.

63 Claims, 14 Drawing Sheets

SCANNER HAVING CONFOCAL OPTICAL SYSTEM, METHOD FOR PRODUCING FOCUS POSITION DATA OF CONFOCAL OPTICAL SYSTEM OF SCANNER HAVING CONFOCAL OPTICAL SYSTEM AND METHOD FOR PRODUCING DIGITAL DATA OF SCANNER HAVING CONFOCAL OPTICAL SYSTEM

BACKGROUND OF THE INVENTION

The present invention relates to a scanner having a confocal optical system, a method for producing focus position data of a confocal optical system of a scanner having a confocal optical system and a method for producing digital data of a scanner having a confocal optical system and, particularly, to a scanner having a confocal optical system, a method for producing focus position data of a confocal optical system of a scanner having a confocal optical system and a method for producing digital data of a scanner having a confocal optical system which can adjust the focus of a confocal optical system with high accuracy without need for special devices and produce digital data for biochemical analysis in a desired manner.

DESCRIPTION OF THE PRIOR ART

An autoradiography detecting system using as a detecting material for detecting radiation a stimulable phosphor which can absorb, store and record the energy of radiation when it is irradiated with radiation and which, when it is then stimulated by an electromagnetic wave having a specified wavelength, can release stimulated emission whose light amount corresponds to the amount of radiation with which it was irradiated is known, which comprises the steps of introducing a radioactive labeling substance into an organism, using the organism or a part of the tissue of the organism as a specimen, superposing the specimen and a stimulable phosphor sheet formed with a stimulable phosphor layer for a certain period of time, storing and recording radiation energy in a stimulable phosphor contained in the stimulable phosphor layer, scanning the stimulable phosphor layer with an electromagnetic wave to excite the stimulable phosphor, photoelectrically detecting the stimulated emission released from the stimulable phosphor to produce digital image signals, effecting image processing on the obtained digital image signals, and reproducing an image on displaying means such as a CRT or the like or a photographic film (see, for example, Japanese Patent Publication No. 1-60784, Japanese Patent Publication No. 1-60782, Japanese Patent Publication No. 4-3952 and the like).

Unlike the system using a photographic film, according to the autoradiography detecting system using the stimulable phosphor as a detecting material, development, which is chemical processing, becomes unnecessary. Further, it is possible to reproduce a desired image by effecting image processing on the obtained image data and effect quantitative analysis using a computer. Use of a stimulable phosphor in these processes is therefore advantageous.

On the other hand, a fluorescence detecting system using a fluorescent substance as a labeling substance instead of a radioactive labeling substance in the autoradiography detecting-system is known. According to this system, it is possible to study a genetic sequence, to study the expression level of a gene, and to effect separation or identification of protein or estimation of the molecular weight or properties of protein or the like. For example, this system can perform a process including the steps of distributing a plurality of DNA fragments on a gel support by means of electrophoresis after a fluorescent dye was added to a solution containing a plurality of DNA fragments to be distributed, or distributing a plurality of DNA fragments on a gel support containing a fluorescent dye, or dipping a gel support on which a plurality of DNA fragments have been distributed by means of electrophoresis in a solution containing a fluorescent dye, thereby labeling the electrophoresed DNA fragments, exciting the fluorescent dye by a stimulating ray to cause it to release fluorescent light, detecting the released fluorescent light to produce an image and detecting the distribution of the DNA fragments on the gel support. This system can also perform a process including the steps of distributing a plurality of DNA fragments on a gel support by means of electrophoresis, denaturing the DNA fragments, transferring at least a part of the denatured DNA fragments onto a transfer support such as a nitrocellulose support by the Southern-blotting method, hybridizing a probe prepared by labeling target DNA and DNA or RNA complementary thereto with the denatured DNA fragments, thereby selectively labeling only the DNA fragments complementary to the probe DNA or probe RNA, exciting the fluorescent dye by a stimulating ray to cause it to release fluorescent light, detecting the released fluorescent light to produce an image and detecting the distribution of the target DNA on the transfer support. This system can further perform a process including the steps of preparing a DNA probe complementary to DNA containing a target gene labeled by a labeling substance, hybridizing it with DNA on a transfer support, combining an enzyme with the complementary DNA labeled by a labeling substance, causing the enzyme to contact a fluorescent substance, transforming the fluorescent substance to a fluorescent substance having fluorescent light releasing property, exciting the thus produced fluorescent substance by a stimulating ray to release fluorescent light, detecting the fluorescent light to produce an image and detecting the distribution of the target DNA on the transfer support. This fluorescence detecting system is advantageous in that a genetic sequence or the like can be easily detected without using a radioactive substance.

Further, a micro-array detecting system has been recently developed, which comprises the steps of using a spotting device to drop at different positions on the surface of a carrier such as a slide glass plate, a membrane filter or the like specific binding substances, which can specifically bind with a substance derived from a living organism such as a hormone, tumor marker, enzyme, antibody, antigen, abzyme, other protein, a nucleic acid, cDNA, DNA, RNA or the like and whose sequence, base length, composition and the like are known, thereby forming a number of independent spots, specifically binding the specific binding substances using a hybridization method or the like with a substance derived from a living organism such as a hormone, tumor marker, enzyme, antibody, antigen, abzyme, other protein, a nuclear acid, cDNA, DNA or mRNA, which is gathered from a living organism by extraction, isolation or the like or is further subjected to chemical processing, chemical modification or the like and which is labeled with a labeling substance such as a fluorescent substance, dye or the like, thereby forming a micro-array, irradiating the micro-array with a stimulating ray, photoelectrically detecting light such as fluorescence emitted from a labeling substance such as a fluorescent substance, dye or the like, and analyzing the substance derived from a living organism. This micro-array image detecting system is advantageous in that a substance derived from a living organism can be analyzed in a short time period by forming a number of spots of specific binding substances at different positions of the surface of a carrier such as a slide glass plate at high density and hybridizing them with a substance derived from a living organism and labeled with a labeling substance.

In addition, a macro-array detecting system using a radio-active labeling substance as a labeling substance has been further developed, which comprises the steps of using a spotting device to drop at different positions on the surface of a carrier such as a membrane filter or the like specific binding substances, which can specifically bind with a substance derived from a living organism such as a hormone, tumor marker, enzyme, antibody, antigen, abzyme, other protein, a nuclear acid, cDNA, DNA, RNA or the like and whose sequence, base length, composition and the like are known, thereby forming a number of independent spots, specifically binding the specific binding substance using a hybridization method or the like with a substance derived from a living organism such as a hormone, tumor marker, enzyme, antibody, antigen, abzyme, other protein, a nuclear acid, cDNA, DNA or mRNA, which is gathered from a living organism by extraction, isolation or the like or is further subjected to chemical processing, chemical modification or the like and which is labeled with a radioactive labeling substance, thereby forming a macro-array, superposing the macro-array and a stimulable phosphor sheet formed with a stimulable phosphor layer, exposing the stimulable phosphor layer to a radioactive labeling substance, irradiating the stimulable phosphor layer with a stimulating ray to excite the stimulable phosphor, photoelectrically detecting the stimulated emission released from the stimulable phosphor to produce biochemical analysis data, and analyzing the substance derived from a living organism.

These systems are constituted so as to irradiate a sample with a stimulating ray to stimulate a stimulable phosphor or a labeling substance such as a fluorescent substance and photoelectrically detect stimulated emission released from the stimulable phosphor, fluorescence emission released from the fluorescent substance or the like, thereby producing biochemical analysis data such as image data of a labeling substance and emitted light amount data. The data producing apparatuses used in these systems fall in two general categories: those that use a scanner and those that use a two-dimensional sensor.

The data producing apparatus using a scanner is advantageous in that data can be produced with high resolution in comparison with one using a two-dimensional sensor.

The micro-array detecting system is constituted so as to scan a sample with a stimulating ray to stimulate a labeling substance such as a fluorescent substance and photoelectrically detect fluorescence emission released from the fluorescent substance or the like, thereby producing biochemical analysis data such as image data of a labeling substance and emitted light amount data and, therefore, it is indispensable to adjust the focus of a light condensing optical system with high accuracy in order to enable high accurate detection.

Therefore, U.S. Pat. Nos. 5,578,832 and 5,834,785 propose a method for adjusting the focus of a light condensing optical system using an auto-focusing system.

In order to adjust the focus of a light condensing optical system using an auto-focusing system, however, it is necessary to provide special devices such as a reflected light detecting optical system, a sensor, a detection circuit and the like and cost increases in proportion.

SUMMARY OF THE INVENTION

It is therefore an object of the present invention to provide a scanner having a confocal optical system, a method for producing focus position data of a confocal optical system of a scanner having a confocal optical system and a method for producing digital data of a scanner having a confocal optical system which can adjusting the focus of a confocal optical system with high accuracy without need for special devices and produce digital data for biochemical analysis in a desired manner.

The above and other objects of the present invention can be accomplished by a scanner comprising at least one laser stimulating ray source for emitting a laser beam, a sample stage on which a sample carrier for carrying at least one sample is to be placed, a scanning means for moving the sample stage in a main scanning direction and in a sub-scanning direction, a confocal optical system, a drive means for an objective lens incorporated in the confocal optical system, a light detector for photoelectrically detecting light, a non-volatile memory, and a control means, the non-volatile memory being constituted so as to store position data produced by setting at least one distance measuring device in the sample carrier for carrying at least one sample, placing the sample carrier on the sample stage, and measuring a distance between the objective lens incorporated in the confocal optical system and a reference position on a surface of the at least one distance measuring device set in the sample carrier and a distance between the objective lens and at least one measurement position on a surface of the at least one distance measuring device different from the reference position, and to store focus position data produced by setting a focus position determination device including a luminescent material having a property to release fluorescence emission or photoluminescence emission upon being irradiated with the laser beam in the sample carrier so that the luminescent material is located at the reference position, scanning the focus position determination device with the laser beam to stimulate the luminescent material located at the reference position, photoelectrically detecting fluorescence emission or photoluminescence emission released from the luminescent material by the light detector, changing the position of the objective lens of the confocal optical system with a predetermined pitch, and determining a focus position of the confocal optical system, the control means being constituted so as to correct the focus position data of the confocal optical system stored in the non-volatile memory with the position data stored in the non-volatile memory, and output a drive signal to the drive means based on the thus corrected focus position data of the confocal optical system, thereby causing it to move the objective lens of the confocal optical system and adjust the position of the objective lens.

According to the present invention, the non-volatile memory is constituted so as to store position data produced by setting at least one distance measuring device in the sample carrier for carrying at least one sample, placing the sample carrier on the sample stage, and measuring the distance between the objective lens incorporated in the confocal optical system and a reference position on the surface of the at least one distance measuring device set in the sample carrier and the distance between the objective lens and at least one measurement position on the surface of the at least one distance measuring device different from the reference position, and to store focus position data produced by setting a focus position determination device including a luminescent material having a property to release fluorescence emission or photoluminescence emission upon being irradiated with the laser beam in the sample carrier so that the luminescent material is located at the reference position, scanning the focus position determination device with the laser beam to stimulate the luminescent material located at the reference position, photoelectrically detecting fluorescence emission or photoluminescence emission released from the luminescent material by the light detector, changing the position of the objective lens of the confocal optical system with a predetermined pitch, and determining the focus position of the confocal optical system, and the control means is constituted so as to correct the focus position data of the confocal optical system stored in the non-volatile memory with the position data stored in the non-volatile memory, and output a drive signal to the drive means based on the thus corrected focus position data of the confocal optical system, thereby causing it to move the objective lens of the confocal optical system and adjust the position of the objective lens. Therefore, since the position of the objective lens of the confocal optical system can be adjusted based on the distance between the at least one distance determination device set in the sample carrier and the objective lens of the confocal optical system, the focus of the confocal optical system can be adjusted in a desired manner without an auto-focusing system provided with special devices such as a reflected light detecting optical system, a sensor, a detection circuit and the like.

In a preferred aspect of the present invention, the position of the objective lens of the confocal optical system at which an integrated value of signal intensity of fluorescence emission or photoluminescence emission detected by the light detector becomes maximum is determined as the focus position of the confocal optical system and is stored in the non-volatile memory as the focus position data.

In a further preferred aspect of the present invention, the position data are produced by measuring the distance between the objective lens incorporated in the confocal optical system and the reference position on the surface of the at least one distance measuring device set in the sample carrier and the distance between the objective lens and the at least one measurement position on the surface of the at least one distance measuring device different from the reference position and calculating a displacement of the at least one measurement position on the surface of the at least one distance measuring device set in the sample carrier different from the reference position with respect to the reference position on the surface of the at least one distance measuring device and are stored in the non-volatile memory.

In a further preferred aspect of the present invention, the position data are produced by measuring the distance between the objective lens incorporated in the confocal optical system and the reference position on the surface of the at least one distance measuring device set in the sample carrier and the distance between the objective lens and two or more measurement positions different from the reference position on the surface of the at least one distance measuring device, calculating displacements of the two or more measurement positions different from the reference position on the surface of the at least one distance measuring device set in the sample carrier with respect to the reference position on the surface of the at least one distance measuring device, and averaging the displacements of the two or more measurement positions different from the reference position on the surface of the at least one distance measuring device with respect to the reference position, and are stored in the non-volatile memory.

According to this preferred aspect of the present invention, it is possible to more accurately adjust the focus of the confocal system because the position data are produced by measuring the distance between the objective lens incorporated in the confocal optical system and the reference position on the surface of the at least one distance measuring device set in the sample carrier and the distance between the objective lens and two or more measurement positions different from the reference position on the surface of the at least one distance measuring device, calculating displacements of the two or more measurement positions different from the reference position on the surface of the at least one distance measuring device set in the sample carrier with respect to the reference position on the surface of the at least one distance measuring device, and averaging the displacements of the two or more measurement positions different from the reference position on the surface of the at least one distance measuring device with respect to the reference position, and are stored in the non-volatile memory.

In a further preferred aspect of the present invention, the scanner further comprises a temperature sensor for detecting a temperature in the scanner and the non-volatile memory is constituted so as to store the temperature coefficients of the displacements of the two or more measurement positions different from the reference position on the surface of the at least one distance measuring device with respect to the reference position produced by measuring the distance between the objective lens incorporated in the confocal optical system and the reference position on the surface of the at least one distance measuring device set in the sample carrier and the distance between the objective lens and two or more measurement positions different from the reference position on the surface of the at least one distance measuring device at two or more different temperatures from each other, and calculating displacements of the two or more measurement positions different from the reference position on the surface of the at least one distance measuring device set in the sample carrier with respect to the reference position on the surface of the at least one distance measuring device, and to store an average value of temperatures in the scanner detected by the temperature sensor when the focus position data of the confocal optical system were produced, and the control means is constituted so as to correct the focus position data of the confocal optical system stored in the non-volatile memory according to difference in temperature between a temperature in the scanner detected by the temperature sensor and the average value of temperatures in the scanner when the focus position data of the confocal optical system were produced and in accordance with the temperature coefficients of the two or more measurement positions different from the reference position on the surface of each of the two or more distance measuring devices with respect to the reference position stored in the non-volatile memory.

According to this preferred aspect of the present invention, it is possible to more accurately adjust the focus of the confocal system even when the temperature in the scanner changes because the non-volatile memory is constituted so as to store the temperature coefficients of the displacements of the two or more measurement positions different from the reference position on the surface of the at least one distance measuring device with respect to the reference position produced by measuring the distance between the objective lens incorporated in the confocal optical system and the reference position on the surface of the at least one distance measuring device set in the sample carrier and the distance between the objective lens and two or more measurement positions different from the reference position on the surface of the at least one distance measuring device at two or more different temperatures from each other, and calculating displacements of the two or more measurement positions different from the reference position on the surface of the at least one distance measuring device set in the sample carrier with respect to the reference position on the surface of the at least one distance measuring device, and to store an average value of temperatures in the scanner detected by the temperature sensor when the focus position data of the confocal optical system were produced, and the control means is constituted so as to correct the focus position data of the confocal optical system stored in the non-volatile memory according to difference in temperature between a temperature in the scanner detected by the temperature sensor and the average value of temperatures in the scanner when the focus position data of the confocal optical system were produced and in accordance with the temperature coefficients of the displacements of the two or more measurement positions different from the reference position on the surface of the at least one distance measuring device with respect to the reference position stored in the non-volatile memory.

In a further preferred aspect of the present invention, the sample carrier is constituted so as to carry two or more distance measuring devices, the non-volatile memory is constituted so as to store the position data produced by placing the sample carrier carrying two or more samples on the sample stage, measuring distances between the objective lens incorporated in the confocal optical system and three or more measurement positions different from each other on each of the two or more distance measuring devices, determining one of the measurement positions on one of the two or more distance measuring devices as the reference position, calculating displacements of the measurement positions on each of the two or more distance measuring devices with respect to the reference position, and averaging the displacements of the measurement positions on each of the two or more distance measuring devices, and the control means is constituted so as to correct the focus position data of the confocal optical system stored in the non-volatile memory based on the position data stored in the non-volatile memory for each of samples set at positions corresponding to positions of the two or more distance measuring devices set in the sample carrier, and output a drive signal to the drive means in accordance with the thus corrected focus position data of the confocal optical system, thereby causing it to move the objective lens of the confocal optical system and adjust the position of the objective lens.

According to this preferred aspect of the present invention, it is possible to accurately adjust the focus of the confocal system for each of a plurality of samples set in the sample carrier because the sample carrier is constituted so as to carry two or more distance measuring devices, the non-volatile memory is constituted so as to store the position data produced by placing the sample carrier carrying two or more samples on the sample stage, measuring distances between the objective lens incorporated in the confocal optical system and three or more measurement positions different from each other on each of the two or more distance measuring devices, determining one of the measurement positions on one of the two or more distance measuring devices as the reference position, calculating displacements of the measurement positions on each of the two or more distance measuring devices with respect to the reference position, and averaging the displacements of the measurement positions on each of the two or more distance measuring devices, and the control means is constituted so as to correct the focus position data of the confocal optical system stored in the non-volatile memory based on the position data stored in the non-volatile memory for each of samples set at positions corresponding to positions of the two or more distance measuring devices set in the sample carrier, and output a drive signal to the drive means in accordance with the thus corrected focus position data of the confocal optical system, thereby causing it to move the objective lens of the confocal optical system and adjust the position of the objective lens.

In a further preferred aspect of the present invention, the temperature coefficients of displacements of the measurement positions with respect to the reference position are calculated by measuring distances between the objective lens incorporated in the confocal optical system and the three or more measurement positions on each of the two or more distance measuring devices determined by one of the measurement positions on one of the two or more distance measuring devices at two or more temperatures different from each other, determining one of the measurement positions on one of the two or more distance measuring devices as the reference position and calculating displacements of the measurement positions on each of the two or more distance measuring devices with respect to the reference position, the non-volatile memory is constituted so as to store an average value of the temperature coefficients of displacements of the measurement positions with respect to the reference position as the temperature coefficient of each of the two or more distance measuring devices and to store an average value of the temperatures in the scanner detected by the temperature sensor when the focus position data were produced, and the control means is constituted so as to correct the focus position data of the confocal optical system stored in the non-volatile memory for each of the two or more distance measuring devices according to difference in temperature between a temperature in the scanner detected by the temperature sensor and the average value of temperatures in the scanner when the focus position data of the confocal optical system were produced and in accordance with the temperature coefficients of the two or more measurement positions different from the reference position on the surface of each of the two or more distance measuring devices with respect to the reference position stored in the non-volatile memory, and output a drive signal to the drive means in accordance with the thus corrected focus position data of the confocal optical system, thereby causing it to move the objective lens of the confocal optical system and adjust the position of the objective lens.

According to this preferred aspect of the present invention, it is possible to accurately adjust the focus of the confocal system for each of a plurality of samples set in the sample carrier even when the temperature in the scanner changes because the temperature coefficients of displacements of the measurement positions with respect to the reference position are calculated by measuring distances between the objective lens incorporated in the confocal optical system and the three or more measurement positions on each of the two or more distance measuring devices at two or more temperatures different from each other and calculating displacements of the measurement positions on each of the two or more distance measuring devices with respect to the reference position, the non-volatile memory is constituted so as to store an average value of the temperature coefficients of displacements of the measurement positions with respect to the reference position as the temperature coefficient of each of the two or more distance measuring devices and to store an average value of the temperatures in the scanner detected by the temperature sensor when the focus position data were produced, and the control means is constituted so as to correct the focus position data of the confocal optical system stored in the non-volatile memory for each of the two or more distance measuring devices according to difference in temperature between a temperature in the scanner detected by the temperature sensor and the average value of temperatures in the scanner when the focus position data of the confocal optical system were produced and in accordance with the temperature coefficients of the two or more distance measuring devices stored in the non-volatile memory, and output a drive signal to the drive means in accordance with the thus corrected focus position data of the confocal optical system, thereby causing it to move the objective lens of the confocal optical system and adjust the position of the objective lens.

In a further preferred aspect of the present invention, the non-volatile memory is constituted so as to store the position data produced by measuring distances between the objective lens incorporated in the confocal optical system and at least two measurement positions different from each other in each main scanning line on each of the two or more distance measuring devices set in the sample carrier, determining one of the measurement positions on one of the two or more distance measuring devices as the reference position, calculating displacements of the measurement positions on each of the two or more distance measuring devices with respect to the reference position, and averaging the displacements of the measurement positions on each of the two or more distance measuring devices.

In a further preferred aspect of the present invention, the temperature coefficients of displacements of the measurement positions with respect to the reference position are calculated by measuring distances between the objective lens incorporated in the confocal optical system and the at least two measurement positions in each main scanning line on each of the two or more distance measuring devices at two or more temperatures different from each other, determining one of the measurement positions on one of the two or more distance measuring devices as the reference position and calculating displacements of the measurement positions on each of the two or more distance measuring devices with respect to the reference position, the non-volatile memory is constituted so as to store an average value of the temperature coefficients of displacements of the measurement positions with respect to the reference position as the temperature coefficient of each of the two or more distance measuring devices and to store an average value of the temperatures in the scanner detected by the temperature sensor when the focus position data were produced, and the control means is constituted so as to correct the focus position data of the confocal optical system stored in the non-volatile memory for each of the two or more distance measuring devices according to difference in temperature between a temperature in the scanner detected by the temperature sensor and the average value of temperatures in the scanner when the focus position data of the confocal optical system were produced and in accordance with the temperature coefficients of the two or more distance measuring devices stored in the non-volatile memory, and output a drive signal to the drive means in accordance with the thus corrected focus position data of the confocal optical system, thereby causing it to move the objective lens of the confocal optical system and adjust the position of the objective lens.

According to this preferred aspect of the present invention, it is possible to more accurately adjust the focus of the confocal system for each of a plurality of samples set in the sample carrier even when the temperature in the scanner changes because the temperature coefficients of displacements of the measurement positions with respect to the reference position are calculated by measuring distances between the objective lens incorporated in the confocal optical system and the at least two measurement positions in each main scanning line on each of the two or more distance measuring devices at two or more temperatures different from each other, determining one of the measurement positions on one of the two or more distance measuring devices as the reference position and calculating displacements of the measurement positions on each of the two or more distance measuring devices with respect to the reference position, the non-volatile memory is constituted so as to store an average value of the temperature coefficients of displacements of the measurement positions with respect to the reference position as the temperature coefficient of each of the two or more distance measuring devices and to store an average value of the temperatures in the scanner detected by the temperature sensor when the focus position data were produced, and the control means is constituted so as to correct the focus position data of the confocal optical system stored in the non-volatile memory for each of the two or more distance measuring devices according to difference in temperature between a temperature in the scanner detected by the temperature sensor and the average value of temperatures in the scanner when the focus position data of the confocal optical system were produced and in accordance with the temperature coefficients of the two or more distance measuring devices stored in the non-volatile memory, and output a drive signal to the drive means in accordance with the thus corrected focus position data of the confocal optical system, thereby causing it to move the objective lens of the confocal optical system and adjust the position of the objective lens.

In a preferred aspect of the present invention, the non-volatile memory is constituted so as to store the position data produced by measuring distances between the objective lens incorporated in the confocal optical system and three measurement positions different from each other in each main scanning line on each of the two or more distance measuring devices set in the sample carrier, determining one of the measurement positions on one of the two or more distance measuring devices as the reference position, calculating displacements of the measurement positions on each of the two or more distance measuring devices with respect to the reference position, and averaging the displacements of the measurement positions on each of the two or more distance measuring devices.

In a further preferred aspect of the present invention, the temperature coefficients of displacements of the measurement positions with respect to the reference position are calculated by measuring distances between the objective lens incorporated in the confocal optical system and the three measurement positions in each main scanning line on each of the two or more distance measuring devices at two or more temperatures different from each other, determining one of the measurement positions on one of the two or more distance measuring devices as the reference position and calculating displacements of the measurement positions on each of the two or more distance measuring devices with respect to the reference position, the non-volatile memory is constituted so as to store an average value of the temperature coefficients of displacements of the measurement positions with respect to the reference position as the temperature coefficient of each of the two or more distance measuring devices and to store an average value of the temperatures in the scanner detected by the temperature sensor when the focus position data were produced, and the control means is constituted so as to correct the focus position data of the confocal optical system stored in the non-volatile memory for each of the two or more distance measuring devices according to difference in temperature between a temperature in the scanner detected by the temperature sensor and the average value of temperatures in the scanner when the focus position data of the confocal optical system were produced and in accordance with the temperature coefficients of the two or more distance measuring devices stored in the non-volatile memory, and output a drive signal to the drive means in accordance with the thus corrected focus position data of the confocal optical system, thereby causing it to move the objective lens of the confocal optical system and adjust the position of the objective lens.

In a further preferred aspect of the present invention, the non-volatile memory is constituted so as to store the position data produced by averaging the displacements of the measurement positions with respect to the reference position for each predetermined number of main scanning lines on each of the two or more distance measuring devices, and the control means is constituted so as to correct the focus position data of the confocal optical system stored in the non-volatile memory for each number of main scanning lines corresponding to the predetermined number of main scanning lines of the samples set at positions in the sample carrier corresponding to positions where the two or more distance measuring devices were set based on the position data stored in the non-volatile memory, and output a drive signal to the drive means in accordance with the thus corrected focus position data of the confocal optical system, thereby causing it to move the objective lens of the confocal optical system and adjust the position of the objective lens.

According to this preferred aspect of the present invention, the non-volatile memory is constituted so as to store the position data produced by averaging the displacements of the measurement positions with respect to the reference position for each predetermined number of main scanning lines on each of the two or more distance measuring devices, and the control means is constituted so as to correct the focus position data of the confocal optical system stored in the non-volatile memory for each number of main scanning lines corresponding to the predetermined number of main scanning lines of the samples set at positions in the sample carrier corresponding to positions where the two or more distance measuring devices were set based on the position data stored in the non-volatile memory, and output a drive signal to the drive means in accordance with the thus corrected focus position data of the confocal optical system, thereby causing it to move the objective lens of the confocal optical system and adjust the position of the objective lens, and, therefore, the position of the objective lens can be more precisely adjusted to enable more accurate adjustment of the focus of the confocal system for each of the plurality of samples set in the sample carrier.

In a further preferred aspect of the present invention, the temperature coefficients of displacements of the measurement positions with respect to the reference position are calculated by measuring distances between the objective lens incorporated in the confocal optical system and three measurement positions in each main scanning line for each predetermined number of main scanning lines on each of the two or more distance measuring devices at two or more temperatures different from each other, determining one of the measurement positions on one of the two or more distance measuring devices as the reference position and calculating displacements of the measurement positions for each predetermined number of main scanning lines on each of the two or more distance measuring devices with respect to the reference position, the non-volatile memory is constituted so as to store an average value of the temperature coefficients of displacements of the measurement positions with respect to the reference position for each predetermined number of main scanning lines as the temperature coefficient of each predetermined number of main scanning lines of each of the two or more distance measuring devices and to store an average value of the temperatures in the scanner detected by the temperature sensor when the focus position data were produced, and the control means is constituted so as to correct the focus position data of the confocal optical system stored in the non-volatile memory for each number of main scanning lines corresponding to the predetermined number of main scanning lines of the samples set at positions in the sample carrier corresponding to positions where the two or more distance measuring devices were set according to difference in temperature between a temperature in the scanner detected by the temperature sensor and the average value of temperatures in the scanner when the focus position data of the confocal optical system were produced and in accordance with the temperature coefficients of the predetermined number of main scanning lines on each of the two or more distance measuring devices, and output a drive signal to the drive means in accordance with the thus corrected focus position data of the confocal optical system, thereby causing it to move the objective lens of the confocal optical system and adjust the position of the objective lens.

According to this preferred aspect of the present invention, the temperature coefficients of displacements of the measurement positions with respect to the reference position are calculated by measuring distances between the objective lens incorporated in the confocal optical system and three measurement positions in each main scanning line for each predetermined number of main scanning lines on each of the two or more distance measuring devices at two or more temperatures different from each other, determining one of the measurement positions on one of the two or more distance measuring devices as the reference position and calculating displacements of the measurement positions for each predetermined number of main scanning lines on each of the two or more distance measuring devices with respect to the reference position, the non-volatile memory is constituted so as to store an average value of the temperature coefficients of displacements of the measurement positions with respect to the reference position for each predetermined number of main scanning lines as the temperature coefficient of each predetermined number of main scanning lines of each of the two or more distance measuring devices and to store an average value of the temperatures in the scanner detected by the temperature sensor when the focus position data were produced, and the control means is constituted so as to correct the focus position data of the confocal optical system stored in the non-volatile memory for each number of main scanning lines corresponding to the predetermined number of main scanning lines of the samples set at positions in the sample carrier corresponding to positions where the two or more distance measuring devices were set according to difference in temperature between a temperature in the scanner detected by the temperature sensor and the average value of temperatures in the scanner when the focus position data of the confocal optical system were produced and in accordance with the temperature coefficients of the predetermined number of main scanning lines on each of the two or more distance measuring devices, and output a drive signal to the drive means in accordance with the thus corrected focus position data of the confocal optical system, thereby causing it to move the objective lens of the confocal optical system and adjust the position of the objective lens, and therefore the position of the objective lens can be more precisely adjusted even when the temperature in the scanner changes to enable more accurate adjustment of the focus of the confocal system for each of the plurality of samples set in the sample carrier.

In a further preferred aspect of the present invention, the scanner further comprises two or more laser stimulating ray sources for emitting laser beams having different wavelengths from each other and the non-volatile memory is constituted so as to store the focus position data of the confocal optical system produced for each wavelength of the laser beam, and the control means is constituted so as to read from the non-volatile memory the focus position data of the confocal optical system corresponding to the wavelength of the laser beam emitted from the laser stimulating ray source to be used for scanning the at least one sample from among the two or more laser stimulating ray sources, and output a drive signal to the drive means in accordance with the thus read the focus position data of the confocal optical system, thereby causing it to move the objective lens of the confocal optical system and adjust the position of the objective lens.

Although the focus position of the confocal optical system depends upon the wavelength of the laser beam, i.e., the stimulating ray, according to this preferred aspect of the present invention, the focus position of the confocal optical system can be adjusted in a desired manner when the laser beam having a wavelength capable of most efficiently stimulating a labeling substance, a fluorescent dye, is selected to stimulate a sample(s) and fluorescence emission released from the sample is photoelectrically detected, because the non-volatile memory is constituted so as to store the focus position data of the confocal optical system produced for each wavelength of the laser beam, and the control means is constituted so as to read from the non-volatile memory the focus position data of the confocal optical system corresponding to the wavelength of the laser beam emitted from the laser stimulating ray source to be used for scanning the at least one sample from among the two or more laser stimulating ray sources, and output a drive signal to the drive means in accordance with the thus read the focus position data of the confocal optical system, thereby causing it to move the objective lens of the confocal optical system and adjust the position of the objective lens.

In a further preferred aspect of the present invention, the distance measuring device is provided with a metal layer on the surface thereof and the position data are produced using an electrostatic capacitance displacement meter.

According to this preferred aspect of the present invention, since the distance measuring device is provided with a metal layer on the surface thereof and the position data are produced using an electrostatic capacitance displacement meter, it is possible to produce the position data on the sub-micron order to enable accurate adjustment of the focus position of the confocal optical system.

In a further preferred aspect of the present invention, the position data are optically produced.

According to this preferred aspect of the present invention, in the case where the position data are produced using an auto-focusing system, a laser displacement meter or the like and the thus produced position data are stored in the non-volatile memory, the scanner itself does not require auto-focusing capability, and, therefore, it is possible to adjust the focus position of the confocal optical system in a desired manner without need for an auto-focusing system including special devices such as a reflected light detection system, a sensor, a detection circuit and the like.

In a further preferred aspect of the present invention, the metal layer of the distance measuring device is formed by a method selected from a group consisting of sputtering, chemical vapor deposition and evaporation.

In a further preferred aspect of the present invention, the metal layer of the distance measuring device is formed by sputtering.

In a further preferred aspect of the present invention, the metal layer of the distance measuring device is formed of a material selected from a group consisting of chromium, aluminum, gold, nickel-chromium alloy and titanium-nickel-chromium alloy.

In a further preferred aspect of the present invention, the metal layer of the distance measuring device is formed of chromium.

In a further preferred aspect of the present invention, the focus position determination device is constituted as a slide glass plate including a spot containing at least one kind of fluorescent dye formed on the surface thereof.

In a further preferred aspect of the present invention, the spot contains two or more kinds of fluorescent dyes capable of efficiently being stimulated by laser beams having different wavelengths from each other.

Although the focus position of the confocal optical system depends upon the wavelength of the laser beam, i.e., the stimulating ray, according to this preferred aspect of the present invention, since the spot contains two or more kinds of fluorescent dyes capable of efficiently being stimulated by laser beams having different wavelengths from each other, it is possible to produce the focus position data of the confocal optical system for each wavelength of the laser beam and store them in the non-volatile memory and, therefore, possible to adjust the focus position of the confocal optical system in a desired manner when the laser beam having a wavelength capable of most efficiently stimulating a labeling substance, a fluorescent dye, is selected to stimulate a sample(s) and fluorescence emission released from the sample is photoelectrically detected.

In a further preferred aspect of the present invention, the spot contains a fluorescent dye capable of being efficiently stimulated by a laser beam having a wavelength between 470 nm and 490 nm, a fluorescent dye capable of being efficiently stimulated by a laser beam having a wavelength between 530 nm and 540 nm and a fluorescent dye capable of being efficiently stimulated by a laser beam having a wavelength between 630 nm and 650 nm.

Although the focus position of the confocal optical system depends upon the wavelength of the laser beam, i.e., the stimulating ray, according to this preferred aspect of the present invention, the focus position of the confocal optical system can be adjusted in a desired manner when the laser beam having a wavelength capable of most efficiently stimulating a labeling substance, a fluorescent dye, is selected to stimulate a sample(s) and fluorescence emission released from the sample is photoelectrically detected, because the focus position data of the confocal optical system can be produced for a laser beam having a wavelength between 470 nm and 490 nm, a laser beam having a wavelength between 530 nm and 540 nm and having a wavelength between 630 nm and 650 nm using the spot containing a fluorescent dye capable of being efficiently stimulated by a laser beam having a wavelength between 470 nm and 490 nm, a fluorescent dye capable of being efficiently stimulated by a laser beam having a wavelength between 530 nm and 540 nm and a fluorescent dye capable of being efficiently stimulated by a laser beam having a wavelength between 630 nm and 650 nm and stored in the non-volatile memory.

In a further preferred aspect of the present invention, the focus position determination device is formed by providing the metal layer on a support formed of an inorganic material which can release fluorescence emission or photoluminescence emission and is not degraded by the irradiation with the laser beam so as to form an opening through which the support is exposed.

Although a fluorescent dye is sometimes degraded with the lapse of time when being irradiated with a laser beam, whereby the amount of released fluorescence emission is lowered and the focus position of the confocal optical system cannot be determined in a desired manner, according to this preferred aspect of the present invention, since the focus position determination device is formed by providing the metal layer on a support formed of an inorganic material which can release fluorescence emission or photoluminescence emission and is not degraded by the irradiation with the laser beam so as to form an opening through which the support is exposed, it is possible to accurately determine the focus position of the confocal optical system in a desired manner.

In a further preferred aspect of the present invention, the support is formed of a material selected from a group consisting of IV group elements, II–VI group compounds, III–V group compounds and complexes thereof.

In a further preferred aspect of the present invention, the support is formed by a color glass filter formed by doping glass containing a material selected from a group consisting of silica sand, soda ash and limestone as a principal component with a solid solution of CdS—CdSe.

Although a fluorescent dye is sometimes degraded with the lapse of time when being irradiated with a laser beam, whereby the amount of released fluorescence emission is lowered and the focus position of the confocal optical system cannot be determined in a desired manner, according to this preferred aspect of the present invention, since the support is formed by a color glass filter formed by doping glass containing a material selected from a group consisting of silica sand, soda ash and limestone as a principal component with a solid solution of CdS—CdSe and is not degraded by the irradiation with the laser beam, it is possible to accurately determine the focus position of the confocal optical system in a desired manner.

In a further preferred aspect of the present invention, the support is formed by a color glass filter formed by doping glass containing a material selected from a group consisting of silica sand, soda ash and limestone as a principal component with a solid solution of ZnS—CdS.

Although a fluorescent dye is sometimes degraded with the lapse of time when being irradiated with a laser beam, whereby an amount of released fluorescence emission is lowered and the focus position of the confocal optical system cannot be determined in a desired manner, according to this preferred aspect of the present invention, since the support is formed by a color glass filter formed by doping glass containing a material selected from a group consisting of silica sand, soda ash and limestone as a principal component with a solid solution of ZnS—CdS and is not degraded by the irradiation with the laser beam, it is possible to accurately determine the focus position of the confocal optical system in a desired manner.

In a further preferred aspect of the present invention, the support is formed by a laminate of an InGaAsP layer and a GaAs layer and the metal layer is formed on the InGaAsP layer.

Although a fluorescent dye is sometimes degraded with the lapse of time when being irradiated with a laser beam, whereby an amount of released fluorescence emission is lowered and the focus position of the confocal optical system cannot be determined in a desired manner, according to this preferred aspect of the present invention, since the support is formed by a laminate of an InGaAsP layer and a GaAs layer, which are not degraded by the irradiation with the laser beam, and the metal layer is formed on the InGaAsP layer, it is possible to accurately determine the focus position of the confocal optical system in a desired manner.

In a further preferred aspect of the present invention, the metal layer is formed by a method selected from a group consisting of sputtering, chemical vapor deposition and evaporation.

In a further preferred aspect of the present invention, the metal layer is formed by sputtering.

In a further preferred aspect of the present invention, the metal layer is formed of a material selected from a group consisting of chromium, aluminum, gold, nickel-chromium alloy and titanium-nickel-chromium alloy.

In a further preferred aspect of the present invention, the metal layer is formed of chromium.

In a further preferred aspect of the present invention, the drive means is constituted as a stepping motor.

In a further preferred aspect of the present invention, the non-volatile memory is constituted so as to store the focus position data in the form of drive pulses applied to the stepping motor and the control means is constituted so as to correct the number of drive pulses stored in the non-volatile memory, and apply the thus corrected number of drive pulses to the stepping motor, thereby causing it to move the objective lens of the confocal optical system and adjust the position of the objective lens.

In a further preferred aspect of the present invention, the scanner further comprises a data processing apparatus, and the non-volatile memory is constituted so as to store coefficients of an nth order function produced by plotting integrated values of signal intensity of fluorescence emission or photoluminescence emission detected by the light detector and fitting the plotted values with the nth order function by the control means and displacements of measurement positions on the at least one distance measuring device with respect to the reference position, the control means or the data processing apparatus is constituted so as to produce shading correction data for correcting shading of digital data of the at least one sample based on the coefficients of the nth order function and the displacements of measurement positions on the at least one distance measuring device with respect to the reference position stored in the non-volatile memory, and the data processing apparatus is constituted so as to correct the digital data of the at least one sample based on the shading correction data.

According to this preferred aspect of the present invention, it is possible to produce shading correction data as well as the focus position data of the confocal optical system and produce the digital data of at least one sample in which the shading has been corrected, because the non-volatile memory is constituted so as to store coefficients of an nth order function produced by plotting integrated values of signal intensity of fluorescence emission or photoluminescence emission detected by the light detector and fitting the plotted values with the nth order function by the control means and displacements of measurement positions on the at least one distance measuring device with respect to the reference position, the control means or the data processing apparatus is constituted so as to produce shading correction data for correcting shading of digital data of the at least one sample based on the coefficients of the nth order function and the displacements of measurement positions on the at least one distance measuring device with respect to the reference position stored in the non-volatile memory, and the data processing apparatus is constituted so as to correct the digital data of the at least one sample based on the shading correction data.

In a further preferred aspect of the present invention, the scanner further comprises a data processing apparatus, and the non-volatile memory is constituted so as to store shading correction data for correcting shading of digital data of the at least one sample produced based on coefficients of an nth order function produced by plotting integrated values of signal intensity of fluorescence emission or photoluminescence emission detected by the light detector and fitting the plotted values with the nth order function by the control means and displacements of measurement positions on the at least one distance measuring device with respect to the reference position, and the data processing apparatus is constituted so as to correct the digital data of the at least one sample based on the shading correction data.

According to this preferred aspect of the present invention, it is possible to produce shading correction data as well as the focus position data of the confocal optical system and produce the digital data of the sample in which the shading has been corrected, because the non-volatile memory is constituted so as to store shading correction data for correcting shading of digital data of the at least one sample produced based on coefficients of an nth order function produced by plotting integrated values of signal intensity of fluorescence emission or photoluminescence emission detected by the light detector and fitting the plotted values with the nth order function by the control means and displacements of measurement positions on the at least one distance measuring device with respect to the reference position, and the data processing apparatus is constituted so as to correct the digital data of the at least one sample based on the shading correction data.

In a further preferred aspect of the present invention, the scanner further comprises a data processing apparatus provided with a memory, the data processing apparatus is constituted so as to produce shading correction data based on digital data of a shading estimation device produced by setting the shading estimation device in which a mask of metal is formed on a support having a property to release fluorescence emission upon being irradiated with a laser beam and capable being processed while retaining optical flatness, thereby regularly forming a plurality of openings through which the support is exposed in the sample carrier, placing the sample carrier on the sample stage, scanning the shading estimation device with the laser beam emitted from the at least one laser stimulating ray source via the openings to stimulate the support at the plurality of openings, photoelectrically detecting fluorescence emission released from the support via the plurality of openings by the light detector to produce analog data, digitizing the analog data, to store the shading correction data of the shading estimation device in the non-volatile memory or the memory of the data processing apparatus, and to correct digital data of the at least one sample based on the shading correction data stored in the non-volatile memory or the memory of the data processing apparatus.

According to this preferred aspect of the present invention, the scanner further comprises a data processing apparatus provided with a memory, the data processing apparatus is constituted so as to produce shading correction data based on digital data of a shading estimation device produced by setting the shading estimation device in which a mask of metal is formed on a support having a property to release fluorescence emission upon being irradiated with a laser beam and capable of being processed while retaining optical flatness, thereby regularly forming a plurality of openings through which the support is exposed in the sample carrier, placing the sample carrier on the sample stage, scanning the shading estimation device with the laser beam emitted from the at least one laser stimulating ray source via the openings to stimulate the support at the plurality of openings, photoelectrically detecting fluorescence emission released from the support via the plurality of openings by the light detector to produce analog data, digitizing the analog data, to store the shading correction data of the shading estimation device in the non-volatile memory or the memory of the data processing apparatus, and to correct digital data of the at least one sample based on the shading correction data stored in the non-volatile memory or the memory of the data processing apparatus, and, therefore, it is possible to produce the correction data by scanning the shading estimation device obtained by providing the mask of metal on the support capable of being processed while retaining optical flatness, thereby forming the plurality of openings through which the support is exposed with the laser beam to store them in the non-volatile memory or the memory of the data processing apparatus and produce digital data of the at least one sample in which shading has been corrected using the shading correction data in the non-volatile memory or the memory of the data processing apparatus.

In a further preferred aspect of the present invention, digital data of the shading estimation device are produced by integrating signal intensity of digital signals obtained by the photoelectrically detecting fluorescence emission released from the support through every opening.

In a further preferred aspect of the present invention, each of the plurality of openings is constituted as a slit.

In a further preferred aspect of the present invention, each of the plurality of openings is constituted as a pinhole.

In a further preferred aspect of the present invention, the digital data of the shading estimation device are produced by scanning the shading estimation device with the laser beam via the plurality of openings after a focus of the confocal optical system is adjusted to the opening located at the reference position among the plurality of openings regularly formed in the shading estimation device, photoelectrically detecting fluorescence emission released from the support to produce analog data and digitizing the analog data.

According to this preferred aspect of the present invention, since the focus of the confocal optical system is adjusted to the opening located at the reference position in an optimum manner, the signal intensity of digital data produced by stimulating the support at the openings other than the opening located at the reference position and photoelectrically detecting fluorescence emission released from the support is lower than the signal intensity of digital data produced by stimulating the support at the opening located at the reference position and photoelectrically detecting fluorescence emission released from the support. Therefore, the shading of the digital data of the at least one sample can be effectively corrected by producing shading correction data which can correct the digital data so that the signal intensity of digital data produced by stimulating the support at the openings other than the opening located at the reference position and photoelectrically detecting fluorescence emission released from the support becomes equal to the signal intensity of digital data produced by stimulating the support at the opening located at the reference position and photoelectrically detecting fluorescence emission released from the support, correcting the digital data of the at least one sample using the thus produced shading correction data.

In a further preferred aspect of the present invention, the shading correction data are produced for each wavelength of the laser beam and stored in the non-volatile memory or the memory of the data processing apparatus.

Although the focus position of the confocal optical system depends upon the wavelengths of laser beams and the shading generated in digital data changes in accordance with the wavelengths of laser beams, according to this preferred aspect of the present invention, it is possible to correct the shading of digital data of the at least one sample when the laser beam having a wavelength capable of most efficiently stimulating a labeling substance such as a fluorescent substance is selected to stimulate at least one sample and fluorescence emission released from the sample is photoelectrically detected, because the shading correction data are produced for each wavelength of the laser beam and stored in the non-volatile memory or the memory of the data processing apparatus.

In a further preferred aspect of the present invention, the support is formed of a material selected from a group consisting of IV group elements, II–VI group compounds, III–V group compounds and complexes thereof.

In a further preferred aspect of the present invention, the support is formed by a color glass filter formed by doping glass containing a material selected from a group consisting of silica sand, soda ash and limestone as a principal component with a solid solution of CdS—CdSe.

According to this preferred aspect of the present invention, since the color glass filter formed by doping glass containing a material selected from a group consisting of silica sand, soda ash and limestone as a principal component with a solid solution of CdS—CdSe can be processed so as to retain optical flatness and has a property to release fluorescence emission upon being irradiated with a laser beam and a plurality of openings through which the color glass filter is exposed can be formed by providing a mask of metal on the color glass filter, it is possible to produce digital data of the at least one sample in which the shading has been accurately corrected by scanning the color glass filter via the plurality of regularly formed openings, photoelectrically detecting fluorescence emission released from the color glass filter at the plurality of openings to produce shading correction data, storing them in the non-volatile memory or the memory of the data processing apparatus and correcting the digital data of the at least one sample using the shading correction data.

In a further preferred aspect of the present invention, the support is formed by a color glass filter formed by doping glass containing a material selected from a group consisting of silica sand, soda ash and limestone as a principal component with a solid solution of ZnS—CdS.

According to this preferred aspect of the present invention, since the color glass filter formed by doping glass containing a material selected from a group consisting of silica sand, soda ash and limestone as a principal component with a solid solution of ZnS—CdS can be processed so as to retain optical flatness and has a property to release fluorescence emission upon being irradiated with a laser beam and a plurality of openings through which the color glass filter is exposed can be formed by providing a mask of metal on the color glass filter, it is possible to produce digital data of the at least one sample in which the shading has been accurately corrected by scanning the color glass filter via the plurality of regularly formed openings, photoelectrically detecting fluorescence emission released from the color glass filter at the plurality of openings to produce shading correction data, storing them in the non-volatile memory or the memory of the data processing apparatus and correcting the digital data of the at least one sample using the shading correction data stored in the non-volatile memory or the memory of the data processing apparatus.

In a further preferred aspect of the present invention, the support is formed by a laminate of an InGaAsP layer and a GaAs layer and the metal layer is formed on the InGaAsP layer.

According to this preferred aspect of the present invention, since the laminate of an InGaAsP layer and a GaAs layer can be processed so as to retain optical flatness and has a property to release fluorescence emission upon being irradiated with a laser beam and a plurality of openings through which the color glass filter is exposed can be formed by providing a mask of metal on the color glass filter, it is possible to produce digital data of the at least one sample in which the shading has been accurately corrected by scanning the color glass filter via the plurality of regularly formed openings, photoelectrically detecting fluorescence emission released from the color glass filter at the plurality of openings to produce shading correction data, storing them in the non-volatile memory or the memory of the data processing apparatus and correcting the digital data of the at least one sample using the shading correction data stored in the non-volatile memory or the memory of the data processing apparatus.

In a further preferred aspect of the present invention, the mask of metal is formed by a method selected from a group consisting of sputtering, chemical vapor deposition and evaporation.

In a further preferred aspect of the present invention, the mask of metal is formed of a material selected from a group consisting of chromium, aluminum, gold, nickel-chromium alloy and titanium-nickel-chromium alloy.

The above and other objects of the present invention can be also accomplished by a method for producing focus position data of a confocal optical system of a scanner having a confocal optical system comprising steps of setting at least one distance measuring device in a sample carrier for carrying at least one sample, placing the sample carrier on the sample stage, measuring a distance between an objective lens incorporated in the confocal optical system and a reference position on a surface of the at least one distance measuring device set in the sample carrier and a distance between the objective lens and at least one measurement position on a surface of the at least one distance measuring device different from the reference position, thereby producing position data, storing them in a non-volatile memory, setting a focus position determination device including a luminescent material having a property to release fluorescence emission or photoluminescence emission upon being irradiated with the laser beam in the sample carrier so that the luminescent material is located at the reference position, scanning the focus position determination device with the laser beam to stimulate the luminescent material located at the reference position, photoelectrically detecting fluorescence emission or photoluminescence emission released from the luminescent material, changing the position of the objective lens of the confocal optical system with a predetermined pitch, determining a focus position of the confocal optical system, thereby producing the position data, and storing them in the non-volatile memory.

According to this preferred aspect of the present invention, the method for producing focus position data of a confocal optical system of a scanner having a confocal optical system comprises the steps of setting at least one distance measuring device in the sample carrier for carrying at least one sample, placing the sample carrier on the sample stage, measuring a distance between the objective lens incorporated in the confocal optical system and a reference position on a surface of the at least one distance measuring device set in the sample carrier and a distance between the objective lens and at least one measurement position on a surface of the at least one distance measuring device different from the reference position thereby producing position data, storing them in a non-volatile memory, setting focus position determination device including a luminescent material having a property to release fluorescence emission or photoluminescence emission upon being irradiated with the laser beam in the sample carrier so that the luminescent material is located at the reference position, scanning the focus position determination device with the laser beam to stimulate the luminescent material located at the reference position, photoelectrically detecting fluorescence emission or photoluminescence emission released from the luminescent material, changing the position of the objective lens of the confocal optical system with a predetermined pitch, determining a focus position of the confocal optical system, thereby producing the position data, and storing them in the non-volatile memory, and, therefore, the objective lens of the confocal optical system can be moved to adjust the position of the objective lens based on the focus position of the confocal is optical system obtained by correcting the focus position of the confocal optical system read from the non-volatile memory in accordance with the position data read from the non-volatile memory, so that the focus of the confocal optical system can be adjusted in a desired manner without an auto-focusing system provided with special devices such as a reflected light detecting optical system, a sensor, a detection circuit and the like.

In a preferred aspect of the present invention, the position of the objective lens of the confocal optical system at which an integrated value of signal intensity of fluorescence emission or photoluminescence emission detected by the light detector becomes maximum is determined as the focus position of the confocal optical.

In a further preferred aspect of the present invention, the method for producing focus position data of a confocal optical system of a scanner having a confocal optical system comprises steps of measuring the distance between the objective lens incorporated in the confocal optical system and the reference position on the surface of the at least one distance measuring device set in the sample carrier and the distance between the objective lens and the at least one measurement position on the surface of the at least one distance measuring device different from the reference position and calculating a displacement of the at least one measurement position on the surface of the at least one distance measuring device set in the sample carrier different from the reference position with respect to the reference position on the surface of the at least one distance measuring device, thereby producing the position data.

In a further preferred aspect of the present invention, the method for producing focus position data of a confocal optical system of a scanner having a confocal optical system comprises steps of measuring the distance between the objective lens incorporated in the confocal optical system and the reference position on the surface of the at least one distance measuring device set in the sample carrier and the distance between the objective lens and two or more measurement positions different from the reference position on the surface of the at least one distance measuring device, calculating displacements of the two or more measurement positions different from the reference position on the surface of the at least one distance measuring device set in the sample carrier with respect to the reference position on the surface of the at least one distance measuring device, and averaging the displacements of the two or more measurement positions different from the reference position on the surface of the at least one distance measuring device with respect to the reference position, thereby producing the position data.

According to this preferred aspect of the present invention, the focus of the confocal system can be more accurately adjusted because the method for producing focus position data of a confocal optical system of a scanner having a confocal optical system comprises steps of measuring the distance between the objective lens incorporated in the confocal optical system and the reference position on the surface of the at least one distance measuring device set in the sample carrier and the distance between the objective lens and two or more measurement positions different from the reference position on the surface of the at least one distance measuring device, calculating displacements of the two or more measurement positions different from the reference position on the surface of the at least one distance measuring device set in the sample carrier with respect to the reference position on the surface of the at least one distance measuring device, and averaging the displacements of the two or more measurement positions different from the reference position on the surface of the at least one distance measuring device with respect to the reference position, thereby producing the position data.

In a further preferred aspect of the present invention, the method for producing focus position data of a confocal optical system of a scanner having a confocal optical system comprises steps of measuring the distance between the objective lens incorporated in the confocal optical system and the reference position on the surface of the at least one distance measuring device set in the sample carrier and the distance between the objective lens and two or more measurement positions different from the reference position on the surface of the at least one distance measuring device at two or more different temperatures from each other, calculating displacements of the two or more measurement positions different from the reference position on the surface of the at least one distance measuring device set in the sample carrier with respect to the reference position on the surface of the at least one distance measuring device, and storing temperature coefficients of the displacements of the two or more measurement positions different from the reference position on the surface of the at least one distance measuring device with respect to the reference position and an average temperature in the scanner when the focus position data were produced in the non-volatile memory.

According to this preferred aspect of the present invention, the method for producing focus position data of a confocal optical system of a scanner having a confocal optical system comprises steps of measuring the distance between the objective lens incorporated in the confocal optical system and the reference position on the surface of the at least one distance measuring device set in the sample carrier and the distance between the objective lens and two or more measurement positions different from the reference position on the surface of the at least one distance measuring device at two or more different temperatures from each other, calculating displacements of the two or more measurement positions different from the reference position on the surface of the at least one distance measuring device set in the sample carrier with respect to the reference position on the surface of the at least one distance measuring device, and storing temperature coefficients of the displacements of the two or more measurement positions different from the reference position on the surface of the at least one distance measuring device with respect to the reference position and an average temperature in the scanner when the focus position data were produced in the non-volatile memory, and, therefore, it is possible to adjust the focus of the confocal optical system in a desired manner even when temperature in the scanner changes by correcting the focus position data of the confocal optical system read from the non-volatile memory according to difference in temperature between the temperature in the scanner and the average temperature in the scanner when the focus position data of the confocal optical system were produced and in accordance with the temperature coefficients of the displacements of the two or more measurement positions different from the reference position on the surface of the at least one distance measuring device with respect to the reference position stored in the non-volatile memory, and moving the objective lens of the confocal optical system based on the thus corrected focus position data of the confocal optical system.

In a further preferred aspect of the present invention, the sample carrier is constituted so as to carry two or more distance measuring devices and the method for producing focus position data of a confocal optical system of a scanner comprises steps of placing the sample carrier carrying two or more samples on the sample stage, measuring distances between the objective lens incorporated in the confocal optical system and three or more measurement positions different from each other on each of the two or more distance measuring devices, determining one of the measurement positions on one of the two or more distance measuring devices as the reference position, calculating displacements of the measurement positions on each of the two or more distance measuring devices with respect to the reference position, averaging the displacements of the measurement positions on each of the two or more distance measuring devices to produce the position data, and storing them in the non-volatile memory.

According to this preferred aspect of the present invention, the sample carrier is constituted so as to carry two or more distance measuring devices and the method for producing focus position data of a confocal optical system of a scanner comprises steps of placing the sample carrier carrying two or more samples on the sample stage, measuring distances between the objective lens incorporated in the confocal optical system and three or more measurement positions different from each other on each of the two or more distance measuring devices, determining one of the measurement positions on one of the two or more distance measuring devices as the reference position, calculating displacements of the measurement positions on each of the two or more distance measuring devices with respect to the reference position, averaging the displacements of the measurement positions on each of the two or more distance measuring devices to produce the position data, and storing them in the non-volatile memory, and, therefore, it is possible to accurately adjust the focus of the confocal system in a desired manner for each of the plurality of samples set in the sample carrier by correcting the focus position data of the confocal optical system read from the non-volatile memory based on the position data read from the non-volatile memory for each of samples set at positions corresponding to positions of the two or more distance measuring devices set in the sample carrier and moving the objective lens of the confocal optical system in accordance with the thus corrected focus position data of the confocal optical system, thereby adjusting the position of the objective lens.

In a further preferred aspect of the present invention, the method for producing focus position data of a confocal optical system of a scanner having a confocal optical system comprises steps of measuring distances between the objective lens incorporated in the confocal optical system and the three or more measurement positions on each of the two or more distance measuring devices with respect to the reference position determined by one of the measurement positions on one of the two or more distance measuring devices at two or more temperatures different from each other, calculating displacements of the measurement positions on each of the two or more distance measuring devices with respect to the reference position to calculate the temperature coefficients of displacements of the measurement positions with respect to the reference position, and storing the thus calculated temperature coefficients and an average temperature in the scanner when the focus position data were produced in the non-volatile memory.

According to this preferred aspect of the present invention, the method for producing focus position data of a confocal optical system of a scanner having a confocal optical system comprises steps of measuring distances between the objective lens incorporated in the confocal optical system and the three or more measurement positions on each of the two or more distance measuring devices with respect to the reference position determined by one of the measurement positions on one of the two or more distance measuring devices at two or more temperatures different from each other, calculating displacements of the measurement positions on each of the two or more distance measuring devices with respect to the reference position to calculate the temperature coefficients of displacements of the measurement positions with respect to the reference position, and storing the thus calculated temperature coefficients and an average temperature in the scanner when the focus position data were produced in the non-volatile memory, and, therefore, it is possible to accurately adjust the focus of the confocal system for each of the plurality of samples set in the sample carrier even when the temperature in the scanner changes by correcting the focus position data of the confocal optical system read from the non-volatile memory for each of the two or more distance measuring devices according to difference in temperature between the temperature in the scanner and the average temperature in the scanner when the focus position data of the confocal optical system were produced and in accordance with the temperature coefficients of the two or more distance measuring devices read from the non-volatile memory and moving the objective lens of the confocal optical system in accordance with the thus corrected focus position data of the confocal optical system, thereby adjusting the position of the objective lens.

In a further preferred aspect of the present invention, the method for producing focus position data of a confocal optical system of a scanner having a confocal optical system comprises steps of measuring distances between the objective lens incorporated in the confocal optical system and at least two measurement positions different from each other in each main scanning line on each of the two or more distance measuring devices set in the sample carrier, determining one of the measurement positions on one of the two or more distance measuring devices as the reference position, calculating displacements of the measurement positions on each of the two or more distance measuring devices with respect to the reference position, averaging the displacements of the measurement positions on each of the two or more distance measuring devices to produce the position data, and storing the thus produced position data in the non-volatile memory.

In a further preferred aspect of the present invention, the method for producing focus position data of a confocal optical system of a scanner having a confocal optical system comprises steps of measuring distances between the objective lens incorporated in the confocal optical system and the at least two measurement positions in each main scanning line on each of the two or more distance measuring devices with respect to the reference position at two or more temperatures different from each other, determining one of the measurement positions on one of the two or more distance measuring devices as the reference position, calculating displacements of the measurement positions on each of the two or more distance measuring devices with respect to the reference position to produce the temperature coefficients of displacements of the measurement positions with respect to the reference position, and storing an average value of the temperature coefficients of displacements of the measurement positions with respect to the reference position as a temperature coefficient and an average temperature in the scanner when the focus position data were produced in the non-volatile memory.

According to this preferred aspect of the present invention, the method for producing focus position data of a confocal optical system of a scanner having a confocal optical system comprises steps of measuring distances between the objective lens incorporated in the confocal optical system and the at least two measurement positions in each main scanning line on each of the two or more distance measuring devices with respect to the reference position at two or more temperatures different from each other, determining one of the measurement positions on one of the two or more distance measuring devices as the reference position, calculating displacements of the measurement positions on each of the two or more distance measuring devices with respect to the reference position to produce the temperature coefficients of displacements of the measurement positions with respect to the reference position, and storing an average value of the temperature coefficients of displacements of the measurement positions with respect to the reference position as a temperature coefficient and an average temperature in the scanner when the focus position data were produced in the non-volatile memory, and, therefore, it is possible to more accurately adjust the focus of the confocal system for each of the plurality of samples set in the sample carrier even when the temperature in the scanner changes by correcting the focus position data of the confocal optical system read from the non-volatile memory for each of the two or more distance measuring devices according to difference in temperature between the temperature in the scanner and the average temperature in the scanner when the focus position data of the confocal optical system were produced and in accordance with the temperature coefficients of the two or more distance measuring devices read from the non-volatile memory and moving the objective lens of the confocal optical system in accordance with the thus corrected focus position data of the confocal optical system, thereby adjusting the position of the objective lens.

In a further preferred aspect of the present invention, the method for producing focus position data of a confocal optical system of a scanner having a confocal optical system comprises steps of measuring distances between the objective lens incorporated in the confocal optical system and three measurement positions different from each other in each main scanning line on each of the two or more distance measuring devices set in the sample carrier, determining one of the measurement positions on one of the two or more distance measuring devices as the reference position, calculating displacements of the measurement positions on each of the two or more distance measuring devices with respect to the reference position, averaging the displacements of the measurement positions on each of the two or more distance measuring devices to produce the position data, and storing the thus produced position data in the non-volatile memory.

In a further preferred aspect of the present invention, the method for producing focus position data of a confocal optical system of a scanner having a confocal optical system comprises steps of measuring distances between the objective lens incorporated in the confocal optical system and the three measurement positions in each main scanning line on each of the two or more distance measuring devices at two or more temperatures different from each other, determining one of the measurement positions on one of the two or more distance measuring devices as the reference position, calculating displacements of the measurement positions on each of the two or more distance measuring devices with respect to the reference position to produce the temperature coefficients of displacements of the measurement positions with respect to the reference position, and storing an average value of the temperature coefficients of displacements of the measurement positions with respect to the reference position as a temperature coefficient and an average temperature in the scanner when the focus position data were produced in the non-volatile memory.

In a further preferred aspect of the present invention, the method for producing focus position data of a confocal optical system of a scanner having a confocal optical system comprises steps of averaging displacements of the measurement positions with respect to the reference position for every predetermined number of the main scanning lines on each of the two or more distance measuring devices to produce the position data and storing the thus produced position data.

According to this preferred aspect of the present invention, since the method for producing focus position data of a confocal optical system of a scanner having a confocal optical system comprises steps of averaging displacements of the measurement positions with respect to the reference position for every predetermined number of the main scanning lines on each of the two or more distance measuring devices to produce the position data and storing the thus produced position data, the position of the objective lens can be more precisely adjusted and it is therefore possible to more accurately adjust the focus of the confocal system for each of the plurality of samples set in the sample carrier.

In a further preferred aspect of the present invention, the method for producing focus position data of a confocal optical system of a scanner having a confocal optical system comprises steps of measuring distances between the objective lens incorporated in the confocal optical system and three measurement positions in each main scanning line for each predetermined number of main scanning lines on each of the two or more distance measuring devices at two or more temperatures different from each other, determining one of the measurement positions on one of the two or more distance measuring devices as the reference position, calculating displacements of the measurement positions with respect to the reference position for every predetermined number of the main scanning lines on each of the two or more distance measuring devices to produce the temperature coefficients of displacements of the measurement positions with respect to the reference position, and storing an average value of the temperature coefficients of displacements of the measurement positions with respect to the reference position every predetermined number of the main scanning lines on each of the two or more distance measuring devices as a temperature coefficient and an average temperature in the scanner when the focus position data were produced in the non-volatile memory.

According to this preferred aspect of the present invention, the method for producing focus position data of a confocal optical system of a scanner having a confocal optical system comprises steps of measuring distances between the objective lens incorporated in the confocal optical system and three measurement positions in each main scanning line for each predetermined number of main scanning lines on each of the two or more distance measuring devices at two or more temperatures different from each other, determining one of the measurement positions on one of the two or more distance measuring devices as the reference position, calculating displacements of the measurement positions with respect to the reference position for every predetermined number of the main scanning lines on each of the two or more distance measuring devices to produce the temperature coefficients of displacements of the measurement positions with respect to the reference position, and storing an average value of the temperature coefficients of displacements of the measurement positions with respect to the reference position every predetermined number of the main scanning lines on each of the two or more distance measuring devices as a temperature coefficient and an average temperature in the scanner when the focus position data were produced in the non-volatile memory, and, therefore, the position of the objective lens can be more precisely adjusted even when the temperature in the scanner changes by correcting the focus position data of the confocal optical system read from the non-volatile memory for each number of main scanning lines corresponding to the predetermined number of main scanning lines of the samples set at positions in the sample carrier corresponding to positions where the two or more distance measuring devices were set according to difference in temperature between the temperature in the scanner and the average value of temperatures in the scanner when the focus position data of the confocal optical system were produced and in accordance with the temperature coefficients of the predetermined number of main scanning lines on each of the two or more distance measuring devices read from the non-volatile memory, and moving the objective lens of the confocal optical system in accordance with the thus corrected focus position data of the confocal optical system, thereby adjusting the position of the objective lens, and it is therefore possible to more accurately adjust the focus of the confocal system for each of the plurality of samples set in the sample carrier.

In a further preferred aspect of the present invention, the focus position data of the confocal optical system are produced for each wavelength of a laser beam and stored in the non-volatile memory.

Although the focus position of the confocal optical system depends upon the wavelength of the laser beam, i.e., the stimulating ray, according to this preferred aspect of the present invention, the focus position data of the confocal optical system are produced for each wavelength of a laser beam and stored in the non-volatile memory, and, therefore, when the laser beam having a wavelength capable of most efficiently stimulating a labeling substance, a fluorescent dye, is selected to stimulate a sample(s) and fluorescence emission released from the sample is photoelectrically detected, the focus position of the confocal optical system can be adjusted in a desired manner by reading the focus position data of the confocal optical system corresponding to the wavelength of a laser beam emitted from the laser stimulating ray source to be used for scanning the at least one sample among two or more laser stimulating ray sources from the non-volatile memory, and moving the objective lens of the confocal optical system based on the thus read focus position data of the confocal optical system, thereby adjusting the position of the objective lens.

In a further preferred aspect of the present invention, the distance measuring device is provided with a metal layer on the surface thereof and the position data are produced using an electrostatic capacitance displacement meter.

According to this preferred aspect of the present invention, since the distance measuring device is provided with a metal layer on the surface thereof and the position data are produced using an electrostatic capacitance displacement meter, it is possible to produce the position data on the sub-micron order to enable accurate adjustment of the focus position of the confocal optical system.

In a further preferred aspect of the present invention, the position data are optically produced.

According to this preferred aspect of the present invention, in the case where the position data are produced using an auto-focusing system, a laser displacement meter or the like and the thus produced position data are stored in the non-volatile memory, the scanner itself does not require auto-focusing capability, and, therefore, it is possible to adjust the focus position of the confocal optical system in a desired manner without need for an auto-focusing system including special devices such as a reflected light detection system, a sensor, a detection circuit and the like.

In a further preferred aspect of the present invention, the metal layer of the distance measuring device is formed by a method selected from a group consisting of sputtering, chemical vapor deposition and evaporation.

In a further preferred aspect of the present invention, the metal layer of the distance measuring device is formed by sputtering.

In a further preferred aspect of the present invention, the metal layer of the distance measuring device is formed of a material selected from a group consisting of chromium, aluminum, gold, nickel-chromium alloy and titanium-nickel-chromium alloy.

In a further preferred aspect of the present invention, the metal layer of the distance measuring device is formed of chromium.

In a further preferred aspect of the present invention, the focus position determination device is constituted as a slide glass plate including a spot containing at least one kind of fluorescent dye formed on the surface thereof.

In a further preferred aspect of the present invention, the spot contains two or more kinds of fluorescent dyes capable of efficiently being stimulated by laser beams having different wavelengths from each other.

Although the focus position of the confocal optical system depends upon the wavelength of the laser beam, i.e., the stimulating ray, according to this preferred aspect of the present invention, since the spot contains two or more kinds of fluorescent dyes capable of efficiently being stimulated by laser beams having different wavelengths from each other, it is possible to produce the focus position data of the confocal optical system for each wavelength of the laser beam and store them in the non-volatile memory and, therefore, it is possible to adjust the focus position of the confocal optical system in a desired manner when the laser beam having a wavelength capable of most efficiently stimulating a labeling substance, a fluorescent dye, is selected to stimulate a sample(s) and fluorescence emission released from the sample is photoelectrically detected.

In a further preferred aspect of the present invention, the spot contains a fluorescent dye capable of being efficiently stimulated by a laser beam having a wavelength between 470 nm and 490 nm, a fluorescent dye capable of being efficiently stimulated by a laser beam having a wavelength between 530 nm and 540 nm and a fluorescent dye capable of being efficiently stimulated by a laser beam having a wavelength between 630 nm and 650 nm.

Although the focus position of the confocal optical system depends upon the wavelength of the laser beam i.e., the stimulating ray, according to this preferred aspect of the present invention, the focus position of the confocal optical system can be adjusted in a desired manner when the laser beam having a wavelength capable of most efficiently stimulating a typical fluorescent dye is selected to stimulate a sample(s) and fluorescence emission released from the sample is photoelectrically detected, because the focus position data of the confocal optical system can be produced for a laser beam having a wavelength between 470 nm and 490 nm, a laser beam having a wavelength between 530 nm and 540 nm and having a wavelength between 630 nm and 650 nm using the spot containing a fluorescent dye capable of being efficiently stimulated by a laser beam having a wavelength between 470 nm and 490 nm, a fluorescent dye capable of being efficiently stimulated by a laser beam having a wavelength between 530 nm and 540 nm and a fluorescent dye capable of being efficiently stimulated by a laser beam having a wavelength between 630 nm and 650 nm and stored in the non-volatile memory.

In a further preferred aspect of the present invention, the focus position determination device is formed by providing the metal layer on a support formed of an inorganic material which can release fluorescence emission or photoluminescence emission and is not degraded by the irradiation with the laser beam so as to form an opening through which the support is exposed.

Although a fluorescent dye is sometimes degraded with the lapse of time when being irradiated with a laser beam, whereby the amount of released fluorescence emission is lowered and the focus position of the confocal optical system cannot be determined in a desired manner, according to this preferred aspect of the present invention, since the focus position determination device is formed by providing the metal layer on a support formed of an inorganic material which can release fluorescence emission or photoluminescence emission and is not degraded by the irradiation with the laser beam so as to form an opening through which the support is exposed, it is possible to accurately determine the focus position of the confocal optical system in a desired manner.

In a further preferred aspect of the present invention, the support is formed of a material selected from a group consisting of IV group elements, II–VI group compounds, III–V group compounds and complexes thereof.

In a further preferred aspect of the present invention, the support is formed by a color glass filter formed by doping glass containing a material selected from a group consisting of silica sand, soda ash and limestone as a principal component with a solid solution of CdS—CdSe.

Although a fluorescent dye is sometimes degraded with the lapse of time when being irradiated with a laser beam, whereby the amount of released fluorescence emission is lowered and the focus position of the confocal optical system cannot be determined in a desired manner, according to this preferred aspect of the present invention, since the support is formed by a color glass filter formed by doping glass containing a material selected from a group consisting of silica sand, soda ash and limestone as a principal component with a solid solution of CdS—CdSe and is not degraded by the irradiation with the laser beam, it is possible to accurately determine the focus position of the confocal optical system in a desired manner.

In a further preferred aspect of the present invention, the support is formed by a color glass filter formed by doping glass containing a material selected from a group consisting of silica sand, soda ash and limestone as a principal component with a solid solution of ZnS—CdS.

Although a fluorescent dye is sometimes degraded with the lapse of time when being irradiated with a laser beam, whereby the amount of released fluorescence emission is lowered and the focus position of the confocal optical system cannot be determined in a desired manner, according to this preferred aspect of the present invention, since the support is formed by a color glass filter formed by doping glass containing a material selected from a group consisting of silica sand, soda ash and limestone as a principal component with a solid solution of ZnS—CdS and is not degraded by the irradiation with the laser beam, it is possible to accurately determine the focus position of the confocal optical system in a desired manner.

In a further preferred aspect of the present invention, the support is formed by a laminate of an InGaAsP layer and a GaAs layer and the metal layer is formed on the InGaAsP layer.

Although a fluorescent dye is sometimes degraded with the lapse of time when being irradiated with a laser beam, whereby the amount of released fluorescence emission is lowered and the focus position of the confocal optical system cannot be determined in a desired manner, according to this preferred aspect of the present invention, since the support is formed by a laminate of an InGaAsP layer and a GaAs layer which are not degraded by the irradiation with the laser beam and the metal layer is formed on the InGaAsP layer, it is possible to accurately determine the focus position of the confocal optical system in a desired manner.

In a further preferred aspect of the present invention, the metal layer is formed by a method selected from a group consisting of sputtering, chemical vapor deposition and evaporation.

In a further preferred aspect of the present invention, the metal layer is formed by sputtering.

In a further preferred aspect of the present invention, the metal layer is formed of a material selected from a group consisting of chromium, aluminum, gold, nickel-chromium alloy and titanium-nickel-chromium alloy.

In a further preferred aspect of the present invention, the metal layer is formed of chromium.

In a further preferred aspect of the present invention, the objective lens of the confocal optical system is adjusted by a stepping motor.

In a further preferred aspect of the present invention, the focus position data are produced in the form of drive pulses to be applied to the stepping motor and stored in the non-volatile memory, the number of drive pulses stored in the non-volatile memory is corrected to be applied to the stepping motor and the objective lens of the confocal optical system is moved to adjust the position of the objective lens.

In a further preferred aspect of the present invention, the method for producing focus position data of a confocal optical system of a scanner having a confocal optical system further comprises steps of plotting integrated values of signal intensity of fluorescence emission or photoluminescence emission, fitting the plotted values with the nth order function to produce coefficients of the nth order function and storing the coefficients of the nth order function in the non-volatile memory as well as displacements of measurement positions on the at least one distance measuring device with respect to the reference position.

According to this preferred aspect of the present invention, the method for producing focus position data of a confocal optical system of a scanner having a confocal optical system further comprises steps of plotting integrated values of signal intensity of fluorescence emission or photoluminescence emission, fitting the plotted values with the nth order function to produce coefficients of the nth order function and storing the coefficients of the nth order function in the non-volatile memory as well as displacements of measurement positions on the at least one distance measuring device with respect to the reference position, and, therefore, it is possible to produce the shading correction data as well as the focus position data of the confocal optical system and produce the digital data of the at least one sample in which the shading has been corrected by producing shading correction data for correcting shading of digital data of the at least one sample based on the coefficients of the nth order function and the displacements of measurement positions on the at least one distance measuring device with respect to the reference position read from the non-volatile memory and correcting the digital data of the at least one sample based on the shading correction data.

In a further preferred aspect of the present invention, the method for producing focus position data of a confocal optical system of a scanner having a confocal optical system further comprises steps of plotting integrated values of signal intensity of detected fluorescence emission or photoluminescence emission, fitting the plotted values with the nth order function to produce coefficients of the nth order function, producing shading correction data for correcting shading of digital data of the at least one sample based on the coefficients of the nth order function and the displacements of measurement positions on the at least one distance measuring device with respect to the reference position and storing the thus produced shading correction data in the non-volatile memory.

According to this preferred aspect of the present invention, it is possible to produce the shading correction data as well as the focus position data of the confocal optical system and produce the digital data of the sample in which the shading has been corrected, because the method for producing focus position data of a confocal optical system of a scanner having a confocal optical system further comprises steps of plotting integrated values of signal intensity of detected fluorescence emission or photoluminescence emission, fitting the plotted values with the nth order function to produce coefficients of the nth order function, producing shading correction data for correcting shading of digital data of the at least one sample based on the coefficients of the nth order function and the displacements of measurement positions on the at least one distance measuring device with respect to the reference position and storing the thus produced shading correction data in the non-volatile memory.

In a further preferred aspect of the present invention, the method for producing focus position data of a confocal optical system of a scanner having a confocal optical system further comprises steps of setting a shading estimation device in which a mask of metal is formed on a support having a property to release fluorescence emission upon being irradiated with a laser beam and capable of being processed while retaining optical flatness, thereby regularly forming a plurality of openings through which the support is exposed in the sample carrier, placing the sample carrier on the sample stage, scanning the shading estimation device with the laser beam via the openings to stimulate the support at the plurality of openings, photoelectrically detecting fluorescence emission released from the support via the plurality of openings to produce analog data, digitizing the analog data, producing digital data of the shading estimation device based on the thus produced digital data, producing shading correction data based on the digital data of the shading estimation device, and storing the thus produced shading correction data in the non-volatile memory or the memory of the scanner.

According to this preferred aspect of the present invention, it is possible to correct digital data of at least one sample by reading shading correction data stored in the non-volatile memory or the memory of the scanner because the method for producing focus position data of a confocal optical system of a scanner having a confocal optical system further comprises steps of setting a shading estimation device in which a mask of metal is formed on a support having a property to release fluorescence emission upon being irradiated with a laser beam and capable of being processed while retaining optical flatness, thereby regularly forming a plurality of openings through which the support is exposed in the sample carrier, placing the sample carrier on the sample stage, scanning the shading estimation device with the laser beam via the openings to stimulate the support at the plurality of openings, photoelectrically detecting fluorescence emission released from the support via the plurality of openings to produce analog data, digitizing the analog data, producing digital data of the shading estimation device based on the thus produced digital data, producing shading correction data based on the digital data of the shading estimation device, and storing the thus produced shading correction data in the non-volatile memory or the memory of the scanner.

In a further preferred aspect of the present invention, digital data of the shading estimation device are produced by integrating signal intensity of digital signals obtained by the photoelectrically detecting fluorescence emission released from the support through every opening.

In a further preferred aspect of the present invention, each of the plurality of openings is constituted as a slit.

In a further preferred aspect of the present invention, each of the plurality of openings is constituted as a pinhole.

In a further preferred aspect of the present invention, the method for producing focus position data of a confocal optical system of a scanner having a confocal optical system further comprises steps of adjusting a focus of the confocal optical system to the opening located at the reference position among the plurality of openings regularly formed in the shading estimation device, scanning the shading estimation device with the laser beam via the plurality of openings, stimulating the support via the plurality of openings, photoelectrically detecting fluorescence emission released from the support to produce analog data, and digitizing the analog data to produce digital data of the shading estimation device.

According to this preferred aspect of the present invention, since the focus of the confocal optical system is adjusted to the opening located at the reference position in an optimum manner, the signal intensity of digital data produced by stimulating the support at openings other than the opening located at the reference position and photoelectrically detecting fluorescence emission released from the support is lower than the signal intensity of digital data produced by stimulating the support at the opening located at the reference position and photoelectrically detecting fluorescence emission released from the support. Therefore, the shading of the digital data of the at least one sample can be effectively corrected by producing shading correction data which can correct the digital data so that the signal intensity of digital data produced by stimulating the support at openings other than the opening located at the reference position and photoelectrically detecting fluorescence emission released from the support becomes equal to the signal intensity of digital data produced by stimulating the support at the opening located at the reference position and photoelectrically detecting fluorescence emission released from the support, correcting the digital data of the at least one sample using the thus produced shading correction data.

In a further preferred aspect of the present invention, the shading correction data are produced for each wavelength of the laser beam and stored in the non-volatile memory or the memory of the scanner.

Although the focus position of the confocal optical system depends upon the wavelengths of laser beams and the shading generated in digital data changes in accordance with the wavelengths of laser beams, according to this preferred aspect of the present invention, it is possible to correct the shading of digital data of the at least one sample when the laser beam having a wavelength capable of most efficiently stimulating a labeling substance such as a fluorescent substance is selected to stimulate at least one sample and fluorescence emission released from the sample is photoelectrically detected, because the shading correction data are produced for each wavelength of the laser beam and stored in the non-volatile memory or the memory of the scanner.

In a further preferred aspect of the present invention, the support is formed of a material selected from a group consisting of IV group elements, II–VI group compounds, III–V group compounds and the complexes thereof.

In a further preferred aspect of the present invention, the support is formed by a color glass filter formed by doping glass containing a material selected from a group consisting of silica sand, soda ash and limestone as a principal component with a solid solution of CdS—CdSe.

According to this preferred aspect of the present invention, since the color glass filter formed by doping glass containing a material selected from a group consisting of silica sand, soda ash and limestone as a principal component with a solid solution of CdS—CdSe can be processed so as to retain optical flatness and has a property to release fluorescence emission upon being irradiated with a laser beam and a plurality of openings through which the color glass filter is exposed can be formed by providing a mask of metal on the color glass filter, it is possible to produce digital data of the at least one sample in which the shading has been accurately corrected by scanning the color glass filter via the plurality of regularly formed openings, photoelectrically detecting fluorescence emission released from the color glass filter at the plurality of openings to produce shading correction data, storing them in the non-volatile memory or the memory of the scanner and correcting the digital data of the at least one sample using the shading correction data.

In a further preferred aspect of the present invention, the support is formed by a color glass filter formed by doping glass containing a material selected from a group consisting of silica sand, soda ash and limestone as a principal component with a solid solution of ZnS—CdS.

According to this preferred aspect of the present invention, since the color glass filter formed by doping glass containing a material selected from a group consisting of silica sand, soda ash and limestone as a principal component with a solid solution of ZnS—CdS can be processed so as to retain optical flatness and has a property to release fluorescence emission upon being irradiated with a laser beam and a plurality of openings through which the color glass filter is exposed can be formed by providing a mask of metal on the color glass filter, it is possible to produce digital data of the at least one sample in which the shading has been accurately corrected by scanning the color glass filter via the plurality of regularly formed openings, photoelectrically detecting fluorescence emission released from the color glass filter at the plurality of openings to produce shading correction data, storing them in the non-volatile memory or the memory of the scanner and correcting the digital data of the at least one sample using the shading correction data stored in the non-volatile memory or the memory of the scanner.

In a further preferred aspect of the present invention, the support is formed by a laminate of an InGaAsP layer and a GaAs layer and the metal layer is formed on the InGaAsP layer.

According to this preferred aspect of the present invention, since the laminate of an InGaAsP layer and a GaAs layer can be processed so as to retain optical flatness and has a property to release fluorescence emission upon being irradiated with a laser beam and a plurality of openings through which the color glass filter is exposed can be formed by providing a mask of metal on the color glass filter, it is possible to produce digital data of the at least one sample in which the shading has been accurately corrected by scanning the color glass filter via the plurality of regularly formed openings, photoelectrically detecting fluorescence emission released from the color glass filter at the plurality of openings to produce shading correction data, storing them in the non-volatile memory or the memory of the scanner and correcting the digital data of the at least one sample using the shading correction data stored in the non-volatile memory or the memory of the scanner.

In a further preferred aspect of the present invention, the mask of metal is formed by a method selected from a group consisting of sputtering, chemical vapor deposition and evaporation.

In a further preferred aspect of the present invention, the mask of metal is formed of a material selected from a group consisting of chromium, aluminum, gold, nickel-chromium alloy and titanium-nickel-chromium alloy.

The above and other objects of the present invention can be also accomplished by a method for producing digital data of a scanner having a confocal optical system comprising steps of reading from the non-volatile memory position data produced by setting at least one distance measuring device in the sample carrier for carrying at least one sample, placing the sample carrier on the sample stage, and measuring a distance between the objective lens incorporated in the confocal optical system and a reference position on a surface of the at least one distance measuring device set in the sample carrier and a distance between the objective lens and at least one measurement position on a surface of the at least one distance measuring device different from the reference position and stored in a non-volatile memory of a scanner, reading focus position data produced by setting a focus position determination device including a luminescent material having a property to release fluorescence emission or photoluminescence emission upon being irradiated with the laser beam in the sample carrier so that the luminescent material is located at the reference position, scanning the focus position determination device with the laser beam to stimulate the luminescent material located at the reference position, photoelectrically detecting fluorescence emission or photoluminescence emission released from the luminescent material, changing the position of the objective lens of the confocal optical system with a predetermined pitch, and determining a focus position of the confocal optical system and stored in the non-volatile memory, correcting the focus position data of the confocal optical system in accordance with the position data, and adjusting the position of the objective lens of the confocal optical system based on the thus corrected focus position data of the confocal optical system.

According to the present invention, the focus of a confocal optical system can be adjusted in a desired manner without an auto-focusing system provided with special devices such as a reflected light detecting optical system, a sensor, a detection circuit and the like, because the method for producing digital data of a scanner having a confocal optical system comprises the steps of reading position data produced by setting at least one distance measuring device in the sample carrier for carrying at least one sample, placing the sample carrier on the sample stage, and measuring a distance between the objective lens incorporated in the confocal optical system and a reference position on a surface of the at least one distance measuring device set in the sample carrier and a distance between the objective lens and at least one measurement position on a surface of the at least one distance measuring device different from the reference position thereby producing position data and stored in a non-volatile memory of a scanner from the non-volatile memory, reading focus position data produced by setting a focus position determination device including a luminescent material having a property to release fluorescence emission or photoluminescence emission upon being irradiated with the laser beam in the sample carrier so that the luminescent material is located at the reference position, scanning the focus position determination device with the laser beam to stimulate the luminescent material located at the reference position, photoelectrically detecting fluorescence emission or photoluminescence emission released from the luminescent material, changing the position of the objective lens of the confocal optical system with a predetermined pitch, and determining a focus position of the confocal optical system and stored in the non-volatile memory, correcting the focus position data of the confocal optical system in accordance with the position data, and adjusting the position of the objective lens of the confocal optical system based on the thus corrected focus position data of the confocal optical system.

In a preferred aspect of the present invention, the position data are produced by measuring the distance between the objective lens incorporated in the confocal optical system and the reference position on the surface of the at least one distance measuring device set in the sample carrier and the distance between the objective lens and the at least one measurement position on the surface of the at least one distance measuring device different from the reference position and calculating a displacement of the at least one measurement position on the surface of the at least one distance measuring device set in the sample carrier different from the reference position with respect to the reference position on the surface of the at least one distance measuring device, and are stored in the non-volatile memory.

In a further preferred aspect of the present invention, the position data are produced by measuring the distance between the objective lens incorporated in the confocal optical system and the reference position on the surface of the at least one distance measuring device set in the sample carrier and the distance between the objective lens and two or more measurement positions different from the reference position on the surface of the at least one distance measuring device, calculating displacements of the two or more measurement positions different from the reference position on the surface of the at least one distance measuring device set in the sample carrier with respect to the reference position on the surface of the at least one distance measuring device, and averaging the displacements of the two or more measurement positions different from the reference position on the surface of the at least one distance measuring device with respect to the reference position, and are stored in the non-volatile memory.

According to this preferred aspect of the present invention, the focus of the confocal system can be more accurately adjusted because the position data are produced by measuring the distance between the objective lens incorporated in the confocal optical system and the reference position on the surface of the at least one distance measuring device set in the sample carrier and the distance between the objective lens and two or more measurement positions different from the reference position on the surface of the at least one distance measuring device, calculating displacements of the two or more measurement positions different from the reference position on the surface of the at least one distance measuring device set in the sample carrier with respect to the reference position on the surface of the at least one distance measuring device, and averaging the displacements of the two or more measurement positions different from the reference position on the surface of the at least one distance measuring device with respect to the reference position, and are stored in the non-volatile memory.

In a further preferred aspect of the present invention, the method for producing digital data of a scanner having a confocal optical system further comprises steps of reading from the non-volatile memory temperature coefficients of the displacements of the two or more measurement positions different from the reference position on the surface of the at least one distance measuring device with respect to the reference position produced by measuring the distance between the objective lens incorporated in the confocal optical system and the reference position on the surface of the at least one distance measuring device set in the sample carrier and the distance between the objective lens and two or more measurement positions different from the reference position on the surface of the at least one distance measuring device at two or more different temperatures from each other, and calculating displacements of the two or more measurement positions different from the reference position on the surface of the at least one distance measuring device set in the sample carrier with respect to the reference position on the surface of the at least one distance measuring device and stored in the non-volatile memory, reading from the non-volatile memory an average temperature in the scanner when the focus position data were produced stored in the non-volatile memory, correcting the focus position data of the confocal optical system according to difference in temperature between the temperature in the scanner and the average temperature in the scanner when the focus position data of the confocal optical system were produced and in accordance with the temperature coefficients of the displacements of the two or more measurement positions different from the reference position on the surface of the at least one distance measuring device with respect to the reference position, and adjusting the position of the objective lens of the confocal optical system based on the thus corrected focus position data of the confocal optical system.

According to this preferred aspect of the present invention, the focus of the confocal optical system can be adjusted in a desired manner even when temperature in the scanner changes because the method for producing digital data of a scanner having a confocal optical system further comprises steps of reading from the non-volatile memory temperature coefficients of the displacements of the two or more measurement positions different from the reference position on the surface of the at least one distance measuring device with respect to the reference position produced by measuring the distance between the objective lens incorporated in the confocal optical system and the reference position on the surface of the at least one distance measuring device set in the sample carrier and the distance between the objective lens and two or more measurement positions different from the reference position on the surface of the at least one distance measuring device at two or more different temperatures from each other, and calculating displacements of the two or more measurement positions different from the reference position on the surface of the at least one distance measuring device set in the sample carrier with respect to the reference position on the surface of the at least one distance measuring device and stored in the non-volatile memory, reading from the non-volatile memory an average temperature in the scanner when the focus position data were produced stored in the non-volatile memory, correcting the focus position data of the confocal optical system according to difference in temperature between the temperature in the scanner and the average temperature in the scanner when the focus position data of the confocal optical system were produced and in accordance with the temperature coefficients of the displacements of the two or more measurement positions different from the reference position on the surface of the at least one distance measuring device with respect to the reference position, and adjusting the position of the objective lens of the confocal optical system based on the thus corrected focus position data of the confocal optical system.

In a further preferred aspect of the present invention, the sample carrier is constituted so as to carry two or more distance measuring devices, and the method for producing digital data of a scanner having a confocal optical system further comprises steps of reading from the non-volatile memory the position data produced by placing the sample carrier carrying two or more samples on the sample stage, measuring distances between the objective lens incorporated in the confocal optical system and three or more measurement positions different from each other on each of the two or more distance measuring devices, determining one of the measurement positions on one of the two or more distance measuring devices as the reference position, calculating displacements of the measurement positions on each of the two or more distance measuring devices with respect to the reference position, and averaging the displacements of the measurement positions on each of the two or more distance measuring devices and stored in the non-volatile memory, correcting the focus position data of the confocal optical system based on the position data for each of samples set at positions corresponding to positions of the two or more distance measuring devices set in the sample carrier, and moving the objective lens of the confocal optical system in accordance with the thus corrected focus position data of the confocal optical system, thereby adjusting the position of the objective lens.

According to this preferred aspect of the present invention, the focus of the confocal system can be accurately adjusted in a desired manner for each of the plurality of samples set in the sample carrier because the sample carrier is constituted so as to carry two or more distance measuring devices, and the method for producing digital data of a scanner having a confocal optical system further comprises steps of reading from the non-volatile memory the position data produced by placing the sample carrier carrying two or more samples on the sample stage, measuring distances between the objective lens incorporated in the confocal optical system and three or more measurement positions different from each other on each of the two or more distance measuring devices, determining one of the measurement positions on one of the two or more distance measuring devices as the reference position, calculating displacements of the measurement positions on each of the two or more distance measuring devices with respect to the reference position, and averaging the displacements of the measurement positions on each of the two or more distance measuring devices and stored in the non-volatile memory, correcting the focus position data of the confocal optical system based on the position data for each of samples set at positions corresponding to positions of the two or more distance measuring devices set in the sample carrier, and moving the objective lens of the confocal optical system in accordance with the thus corrected focus position data of the confocal optical system, thereby adjusting the position of the objective lens.

In a further preferred aspect of the present invention, the method for producing digital data of a scanner having a confocal optical system further comprises steps of reading from the non-volatile memory the temperature coefficients of displacements of the measurement positions with respect to the reference position produced by measuring distances between the objective lens incorporated in the confocal optical system and the three or more measurement positions on each of the two or more distance measuring devices with respect to the reference position determined by one of the measurement positions on one of the two or more distance measuring devices at two or more temperatures different from each other, and calculating displacements of the measurement positions on each of the two or more distance measuring devices with respect to the reference position and stored in the non-volatile memory, reading from the non-volatile memory the average temperature in the scanner when the focus position data of the confocal optical system were produced stored in the non-volatile memory, correcting the focus position data of the confocal optical system for each of the two or more distance measuring devices according to difference in temperature between the temperature in the scanner and the average temperature in the scanner when the focus position data of the confocal optical system were produced and in accordance with the temperature coefficients of the two or more distance measuring devices stored in the non-volatile memory, and moving the objective lens of the confocal optical system in accordance with the thus corrected focus position data of the confocal optical system, thereby adjusting the position of the objective lens.

According to this preferred aspect of the present invention, the focus of the confocal system can be accurately adjusted for each of the plurality of samples set in the sample carrier even when the temperature in the scanner changes because the method for producing digital data of a scanner having a confocal optical system further comprises steps of reading from the non-volatile memory the temperature coefficients of displacements of the measurement positions with respect to the reference position produced by measuring distances between the objective lens incorporated in the confocal optical system and the three or more measurement positions on each of the two or more distance measuring devices with respect to the reference position determined by one of the measurement positions on one of the two or more distance measuring devices at two or more temperatures different from each other, and calculating displacements of the measurement positions on each of the two or more distance measuring devices with respect to the reference position and stored in the non-volatile memory, reading from the non-volatile memory the average temperature in the scanner when the focus position data of the confocal optical system were produced stored in the non-volatile memory, correcting the focus position data of the confocal optical system for each of the two or more distance measuring devices according to difference in temperature between the temperature in the scanner and the average temperature in the scanner when the focus position data of the confocal optical system were produced and in accordance with the temperature coefficients of the two or more distance measuring devices stored in the non-volatile memory, and moving the objective lens of the confocal optical system in accordance with the thus corrected focus position data of the confocal optical system, thereby adjusting the position of the objective lens.

In a further preferred aspect of the present invention, the method for producing digital data of a scanner having a confocal optical system further comprises steps of reading the position data produced by measuring distances between the objective lens incorporated in the confocal optical system and at least two measurement positions different from each other in each main scanning line on each of the two or more distance measuring devices set in the sample carrier, determining one of the measurement positions on one of the two or more distance measuring devices as the reference position, and calculating displacements of the measurement positions on each of the two or more distance measuring devices with respect to the reference position, averaging the displacements of the measurement positions on each of the two or more distance measuring devices and stored in the non-volatile memory, correcting the focus position data of the confocal optical system read from the non-volatile memory based on the position data for each of the samples set at positions corresponding to positions of the two or more distance measuring devices set in the sample carrier, and moving the objective lens of the confocal optical system in accordance with the thus corrected focus position data of the confocal optical system, thereby adjusting the position of the objective lens.

In a further preferred aspect of the present invention, the method for producing digital data of a scanner having a confocal optical system further comprises steps of reading from the non-volatile memory an average value of the temperature coefficients of displacements of the measurement positions on each of the two or more distance measuring devices with respect to the reference position produced by measuring distances between the objective lens incorporated in the confocal optical system and the at least two measurement positions in each main scanning line on each of the two or more distance measuring devices at two or more temperatures different from each other, determining one of the measurement positions on one of the two or more distance measuring devices as the reference position, calculating displacements of the measurement positions on each of the two or more distance measuring devices with respect to the reference position to produce the temperature coefficients of displacements of the measurement positions with respect to the reference position, and averaging the temperature coefficients and stored in the non-volatile memory, reading from the non-volatile memory the average temperature in the scanner when the focus position data were produced stored in the non-volatile memory, correcting the focus position data of the confocal optical system read from the non-volatile memory for each of the two or more distance measuring devices according to difference in temperature between the temperature in the scanner and the average temperature in the scanner when the focus position data of the confocal optical system were produced and in accordance with the temperature coefficients of the two or more distance measuring devices, and moving the objective lens of the confocal optical system in accordance with the thus corrected focus position data of the confocal optical system, thereby adjusting the position of the objective lens.

According to this preferred aspect of the present invention, the focus of the confocal system can be more accurately adjusted for each of the plurality of samples set in the sample carrier even when the temperature in the scanner changes because the method for producing digital data of a scanner having a confocal optical system further comprises steps of reading from the non-volatile memory an average value of the temperature coefficients of displacements of the measurement positions on each of the two or more distance measuring devices with respect to the reference position produced by measuring distances between the objective lens incorporated in the confocal optical system and the at least two measurement positions in each main scanning line on each of the two or more distance measuring devices at two or more temperatures different from each other, determining one of the measurement positions on one of the two or more distance measuring devices as the reference position, calculating displacements of the measurement positions on each of the two or more distance measuring devices with respect to the reference position to produce the temperature coefficients of displacements of the measurement positions with respect to the reference position, and averaging the temperature coefficients and stored in the non-volatile memory, reading from the non-volatile memory the average temperature in the scanner when the focus position data were produced stored in the non-volatile memory, correcting the focus position data of the confocal optical system read from the non-volatile memory for each of the two or more distance measuring devices according to difference in temperature between the temperature in the scanner and the average temperature in the scanner when the focus position data of the confocal optical system were produced and in accordance with the temperature coefficients of the two or more distance measuring devices, and moving the objective lens of the confocal optical system in accordance with the thus corrected focus position data of the confocal optical system, thereby adjusting the position of the objective lens.

In a further preferred aspect of the present invention, the method for producing digital data of a scanner having a confocal optical system further comprises steps of reading the position data produced by measuring distances between the objective lens incorporated in the confocal optical system and three measurement positions different from each other in each main scanning line on each of the two or more distance measuring devices set in the sample carrier, determining one of the measurement positions on one of the two or more distance measuring devices as the reference position, calculating displacements of the measurement positions on each of the two or more distance measuring devices with respect to the reference position, and averaging the displacements of the measurement positions on each of the two or more distance measuring devices and stored in the non-volatile memory, correcting the focus position data of the confocal optical system read from the non-volatile memory based on the position data for each of the samples set at positions corresponding to positions of the two or more distance measuring devices set in the sample carrier, and moving the objective lens of the confocal optical system in accordance with the thus corrected focus position data of the confocal optical system, thereby adjusting the position of the objective lens.

In a further preferred aspect of the present invention, the method for producing digital data of a scanner having a confocal optical system further comprises steps of reading from the non-volatile memory an average value of the temperature coefficients of displacements of the measurement positions on each of the two or more distance measuring devices with respect to the reference position produced by measuring distances between the objective lens incorporated in the confocal optical system and the three measurement positions in each main scanning line on each of the two or more distance measuring devices at two or more temperatures different from each other, determining one of the measurement positions on one of the two or more distance measuring devices as the reference position, calculating displacements of the measurement positions on each of the two or more distance measuring devices with respect to the reference position to produce the temperature coefficients of displacements of the measurement positions with respect to the reference position, and averaging the temperature coefficients and stored in the non-volatile memory as temperature coefficients of the two or more distance measuring devices, reading from the non-volatile memory the average temperature in the scanner when the focus position data were produced stored in the non-volatile memory, correcting the focus position data of the confocal optical system read from the non-volatile memory for each of the two or more distance measuring devices according to difference in temperature between the temperature in the scanner and the average temperature in the scanner when the focus position data of the confocal optical system were produced and in accordance with the temperature coefficients of the two or more distance measuring devices, and moving the objective lens of the confocal optical system in accordance with the thus corrected focus position data of the confocal optical system, thereby adjusting the position of the objective lens.

In a further preferred aspect of the present invention, the method for producing digital data of a scanner having a confocal optical system further comprises steps of reading from the non-volatile memory the position data produced by averaging displacements of the measurement positions with respect to the reference position for every predetermined number of the main scanning lines on each of the two or more distance measuring devices, correcting the focus position data of the confocal optical system read from the non-volatile memory based on the position data for every predetermined number of the main scanning lines corresponding to the predetermined number of the main scanning lines on each of the samples set at positions in the sample carrier corresponding to positions where the two or more distance measuring devices are set, and moving the objective lens of the confocal optical system in accordance with the thus corrected focus position data of the confocal optical system, thereby adjusting the position of the objective lens.

According to this preferred aspect of the present invention, the position of the objective lens can be more precisely adjusted and the focus of the confocal system can therefore be more accurately adjusted for each of the plurality of samples set in the sample carrier, because the method for producing digital data of a scanner having a confocal optical system further comprises steps of reading from the non-volatile memory the position data produced by averaging displacements of the measurement positions with respect to the reference position for every predetermined number of the main scanning lines on each of the two or more distance measuring devices, correcting the focus position data of the confocal optical system read from the non-volatile memory based on the position data for every predetermined number of the main scanning lines corresponding to the predetermined number of the main scanning lines on each of the samples set at positions in the sample carrier corresponding to positions where the two or more distance measuring devices are set, and moving the objective lens of the confocal optical system in accordance with the thus corrected focus position data of the confocal optical system, thereby adjusting the position of the objective lens.

In a further preferred aspect of the present invention, the method for producing digital data of a scanner having a confocal optical system further comprises steps of reading from the non-volatile memory an average value of the temperature coefficients of displacements of the measurement positions on each of the two or more distance measuring devices with respect to the reference position produced by measuring distances between the objective lens incorporated in the confocal optical system and three measurement positions in each main scanning line for each predetermined number of main scanning lines on each of the two or more distance measuring devices at two or more temperatures different from each other, determining one of the measurement positions on one of the two or more distance measuring devices as the reference position, calculating displacements of the measurement positions with respect to the reference position for every predetermined number of the main scanning lines on each of the two or more distance measuring devices to produce the temperature coefficients of displacements of the measurement positions with respect to the reference position, averaging the temperature coefficients of displacements of the measurement positions with respect to the reference position and stored in the non-volatile memory as temperature coefficients for every predetermined number of the main scanning lines on each of the two or more distance measuring devices, reading from the non-volatile memory the average temperature in the scanner when the focus position data were produced stored in the non-volatile memory, correcting the focus position data of the confocal optical system read from the non-volatile memory according to difference in temperature between the temperature in the scanner and the average temperature in the scanner when the focus position data of the confocal optical system were produced and in accordance with the temperature coefficients for every predetermined number of the main scanning lines on each of the two or more distance measuring devices for every predetermined number of the main scanning lines corresponding to the predetermined number of the main scanning lines on each of the samples set at positions in the sample carrier corresponding to positions where the two or more distance measuring devices are set, and moving the objective lens of the confocal optical system in accordance with the thus corrected focus position data of the confocal optical system, thereby adjusting the position of the objective lens.

According to this preferred aspect of the present invention, the method for producing digital data of a scanner having a confocal optical system further comprises steps of reading from the non-volatile memory an average value of the temperature coefficients of displacements of the measurement positions on each of the two or more distance measuring devices with respect to the reference position produced by measuring distances between the objective lens incorporated in the confocal optical system and three measurement positions in each main scanning line for each predetermined number of main scanning lines on each of the two or more distance measuring devices at two or more temperatures different from each other, determining one of the measurement positions on one of the two or more distance measuring devices as the reference position, calculating displacements of the measurement positions with respect to the reference position for every predetermined number of the main scanning lines on each of the two or more distance measuring devices to produce the temperature coefficients of displacements of the measurement positions with respect to the reference position, averaging the temperature coefficients of displacements of the measurement positions with respect to the reference position and stored in the non-volatile memory as temperature coefficients for every predetermined number of the main scanning lines on each of the two or more distance measuring devices, reading from the non-volatile memory the average temperature in the scanner when the focus position data were produced stored in the non-volatile memory, correcting the focus position data of the confocal optical system read from the non-volatile memory according to difference in temperature between the temperature in the scanner and the average temperature in the scanner when the focus position data of the confocal optical system were produced and in accordance with the temperature coefficients for every predetermined number of the main scanning lines on each of the two or more distance measuring devices for every predetermined number of the main scanning lines corresponding to the predetermined number of the main scanning lines on each of the samples set at positions in the sample carrier corresponding to positions where the two or more distance measuring devices are set, and moving the objective lens of the confocal optical system in accordance with the thus corrected focus position data of the confocal optical system, thereby adjusting the position of the objective lens, and, therefore, the position of the objective lens can be more precisely adjusted even when the temperature in the scanner changes so that it is possible to more accurately adjust the focus of the confocal system for each of the plurality of samples set in the sample carrier.

In a further preferred aspect of the present invention, the objective lens of the confocal optical system is adjusted by a stepping motor.

In a further preferred aspect of the present invention, the method for producing digital data of a scanner having a confocal optical system further comprises steps of reading from the non-volatile memory coefficients of an nth order function produced by plotting integrated values of signal intensity of fluorescence emission or photoluminescence emission and fitting the plotted values with the nth order function and stored in the non-volatile memory, reading from the non-volatile memory displacements of measurement positions on the at least one distance measuring device with respect to the reference position stored in the non-volatile memory, producing shading correction data for correcting shading of digital data of the at least one sample based on the coefficients of the nth order function and the displacements of measurement positions on the at least one distance measuring device with respect to the reference position, and correcting digital data of the at least one sample based on the shading correction data.

According to this preferred aspect of the present invention, it is possible to produce the shading correction data as well as the focus position data of the confocal optical system and produce the digital data of the at least one sample in which the shading has been corrected, because the method for producing digital data of a scanner having a confocal optical system further comprises steps of reading from the non-volatile memory coefficients of an nth order function produced by plotting integrated values of signal intensity of fluorescence emission or photoluminescence emission and fitting the plotted values with the nth order function and stored in the non-volatile memory, reading from the non-volatile memory displacements of measurement positions on the at least one distance measuring device with respect to the reference position stored in the non-volatile memory, producing shading correction data for correcting shading of digital data of the at least one sample based on the coefficients of the nth order function and the displacements of measurement positions on the at least one distance measuring device with respect to the reference position, and correcting digital data of the at least one sample based on the shading correction data.

In a further preferred aspect of the present invention, the method for producing digital data of a scanner having a confocal optical system further comprises steps of setting a shading estimation device in which a mask of metal is formed on a support having a property to release fluorescence emission upon being irradiated with a laser beam and capable of being processed while retaining optical flatness, thereby regularly forming a plurality of openings through which the support is exposed in the sample carrier, placing the sample carrier on the sample stage, scanning the shading estimation device with the laser beam via the openings to stimulate the support at the plurality of openings, photoelectrically detecting fluorescence emission released from the support via the plurality of openings to produce analog data, digitizing the analog data, producing digital data of the shading estimation device based on the thus produced digital data, producing shading correction data based on the digital data of the shading estimation device, storing the thus produced shading correction data in the non-volatile memory or the memory of the scanner, and reading the shading correction data to correct digital data of the at least one samples therewith.

According to this preferred aspect of the present invention, since it is possible to correct digital data of the at least one samples using the shading correction data read from the non-volatile memory or the memory of the scanner because the method for producing digital data of a scanner having a confocal optical system further comprises steps of setting a shading estimation device in which a mask of metal is formed on a support having a property to release fluorescence emission upon being irradiated with a laser beam and capable of being processed while retaining optical flatness, thereby regularly forming a plurality of openings through which the support is exposed in the sample carrier, placing the sample carrier on the sample stage, scanning the shading estimation device with the laser beam via the openings to stimulate the support at the plurality of openings, photoelectrically detecting fluorescence emission released from the support via the plurality of openings to produce analog data, digitizing the analog data, producing digital data of the shading estimation device based on the thus produced digital data, producing shading correction data based on the digital data of the shading estimation device, storing the thus produced shading correction data in the non-volatile memory or the memory of the scanner, and reading the shading correction data to correct digital data of the at least one samples therewith.

In a further preferred aspect of the present invention, each of the plurality of openings is constituted as a slit.

In a further preferred aspect of the present invention, each of the plurality of openings is constituted as a pinhole.

In a further preferred aspect of the present invention, the method for producing digital data of a scanner having a confocal optical system further comprises steps of adjusting a focus of the confocal optical system to the opening located at the reference position among the plurality of openings regularly formed in the shading estimation device, scanning the shading estimation device with the laser beam via the plurality of openings, stimulating the support via the plurality of openings, photoelectrically detecting fluorescence emission released from the support to produce analog data, digitizing the analog data to produce digital data of the shading estimation device, producing the shading correction data based on the digital data of the shading estimation device, and storing the thus produced shading correction data in the non-volatile memory or the memory of the scanner.

According to this preferred aspect of the present invention, since the focus of the confocal optical system is adjusted to the opening located at the reference position in an optimum manner, the signal intensity of digital data produced by stimulating the support at openings other than the opening located at the reference position and photoelectrically detecting fluorescence emission released from the support is lower than the signal intensity of digital data produced by stimulating the support at the opening located at the reference position and photoelectrically detecting fluorescence emission released from the support. Therefore, the shading of the digital data of the at least one sample can be effectively corrected by producing shading correction data which can correct the digital data so that the signal intensity of digital data produced by stimulating the support at openings other than the opening located at the reference position and photoelectrically detecting fluorescence emission released from the support becomes equal to the signal intensity of digital data produced by stimulating the support at the opening located at the reference position and photoelectrically detecting fluorescence emission released from the support, correcting the digital data of the at least one sample using the thus produced shading correction data.

In a further preferred aspect of the present invention, the support is formed of a material selected from a group consisting of IV group elements, II–VI group compounds, III–V group compounds and complexes thereof.

In a further preferred aspect of the present invention, the mask of metal is formed of a material selected from a group consisting of chromium, aluminum, gold, nickel-chromium alloy and titanium-nickel-chromium alloy.

The above and other objects and features of the present invention will become apparent from the following description made with reference to the accompanying drawings.

DESCRIPTION OF THE PREFERRED EMBODIMENT

Figure 1:
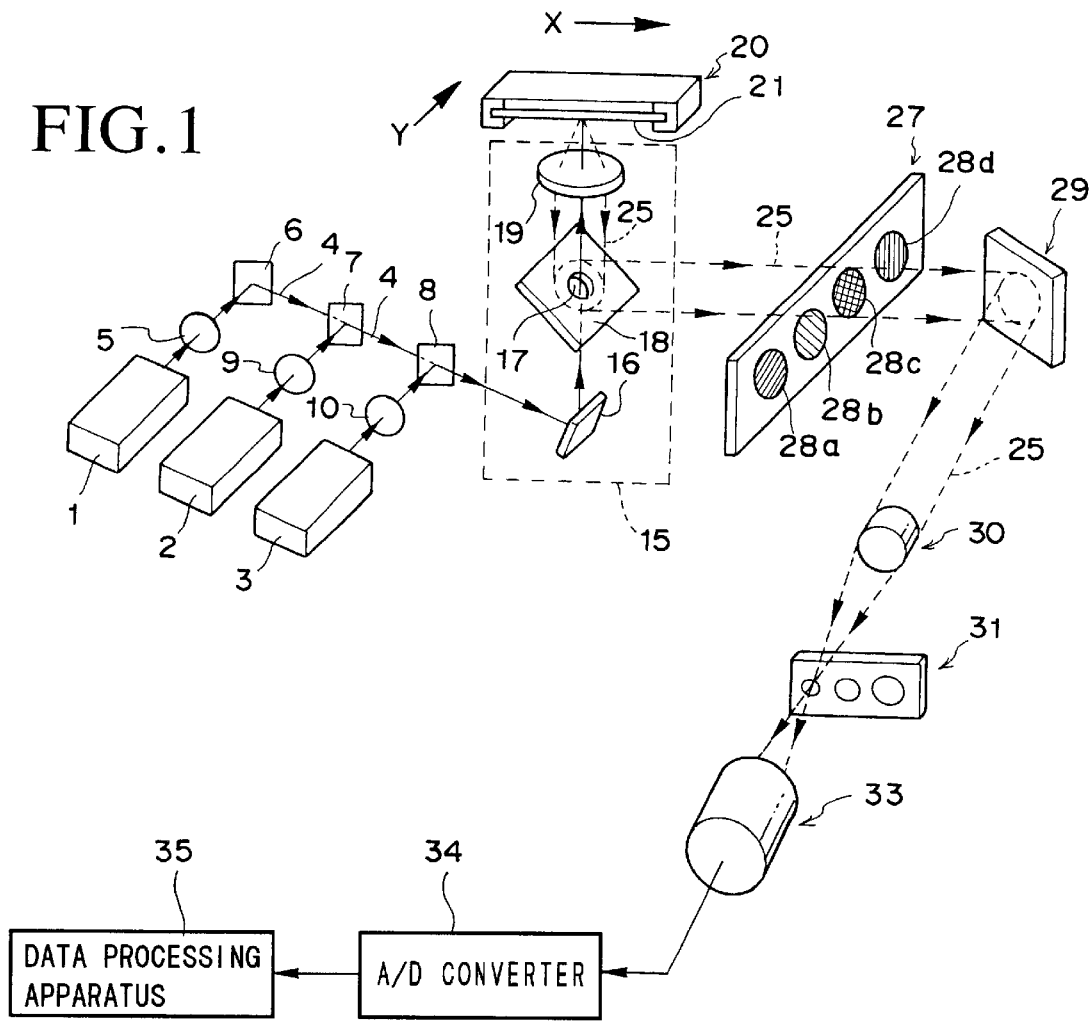
FIG. 1 is a schematic perspective view showing a scanner which is a preferred embodiment of the present invention.

FIG. 1 is a schematic perspective view showing a scanner which is a preferred embodiment of the present invention.

As shown in FIG. 1, a scanner according to this embodiment includes a first laser stimulating ray source 1 for emitting a laser beam having a wavelength of 640 nm, a second laser stimulating ray source 2 for emitting a laser beam having a wavelength of 532 nm and a third laser stimulating ray source 3 for emitting a laser beam having a wavelength of 473 nm. In this embodiment, the first laser stimulating ray source 1 constituted by a semiconductor laser beam source and the second laser stimulating ray source 2 and the third laser stimulating ray source 3 are constituted by a second harmonic generation element.

A laser beam 4 emitted from the first laser stimulating source 1 passes through a collimator lens 5, thereby being made a parallel beam, and is reflected by a mirror 6. A first dichroic mirror 7 for transmitting light having a wavelength of 640 nm but reflecting light having a wavelength of 532 nm and a second dichroic mirror 8 for transmitting light having a wavelength equal to and longer than 532 nm but reflecting light having a wavelength of 473 nm are provided in an optical path of the laser beam 4 emitted from the first laser stimulating source 1 and reflected by the mirror 6. The laser beam 4 emitted from the first laser stimulating ray source 1 passes through the first dichroic mirror 7 and the second dichroic mirror 8 and enters an optical unit 15.

On the other hand, the laser beam 4 emitted from the second laser stimulating ray source 2 passes through a collimator lens 9, thereby being made a parallel beam, and is reflected by the first dichroic mirror 7, thereby changing its direction by 90 degrees. The laser beam 4 then passes through the second dichroic mirror 8 and enters the optical unit 15.

Further, the laser beam 4 emitted from the third laser stimulating ray source 3 passes through a collimator lens 10, thereby being made a parallel beam, and is reflected by the second dichroic mirror 8, thereby changing its direction by 90 degrees.

The optical unit 15 includes a mirror 16, a perforated mirror 18 whose center portion is formed with a hole 17 and a lens 19. The laser beam 4 entering the optical unit 15 is reflected by the mirror 16 and passes through the hole 17 formed in the perforated mirror 18 and the lens 19, thereby entering a sample carrier 21 set on a sample stage 20. The sample stage 20 is constituted so as to be movable by a scanning mechanism (not shown in FIG. 1) in the X direction and the Y direction in FIG. 1.

The scanner according to this embodiment is constituted so as to produce image data for biochemical analysis by scanning a micro-array including a slide glass plate on which a number of spots of a specimen selectively labeled with a fluorescent dye are formed as a substrate with a laser beam 4 to stimulate the fluorescent dye and photoelectrically detecting fluorescence emission released from the fluorescent dye and to also produce image data for biochemical analysis by scanning a fluorescence sample including a transfer support containing denatured DNA fragments selectively labeled with a fluorescent dye as a substrate with a laser beam 4 to stimulate the fluorescent dye and photoelectrically detecting fluorescence emission released from the fluorescent dye. The image reading apparatus according to this embodiment is further constituted so as to produce image data for biochemical analysis by scanning a stimulable phosphor layer of a stimulable phosphor sheet in which locational information of a radioactive labeling substance are recorded by closely contacting a substrate such as a membrane filter having a number of spots of a specimen selectively labeled with a radioactive labeling substance and the stimulable phosphor sheet formed with the stimulable phosphor layer containing a stimulable phosphor to expose the stimulable phosphor layer with the radioactive labeling substance with a laser beam 4 to excite the stimulable phosphor and photoelectrically detecting stimulated emission released from the stimulable phosphor.

When the laser beam 4 is impinged on the sample 22 from the optical unit 15, a fluorescent substance is excited by the laser beam 4 to release fluorescence emission in the case where the sample 22 is a micro-array or a fluorescence sample. On the other hand, in the case where the sample 22 is a stimulable phosphor sheet, stimulable phosphors contained in the stimulable phosphor sheet are excited by the laser beam 4 to release stimulated emission.

The fluorescence emission or the stimulated emission 25 released from the sample 22 is made into a parallel beam by the lens 19 of the optical unit 15 and reflected by the perforated mirror 18, thereby entering one of four filters 28a, 28b, 28c and 28d of a filter unit 27.

The filter unit 27 is constituted to be laterally movable in FIG. 1 by a motor (not shown) so that a predetermined one of the filters 28a, 28b, 28c and 28d is located in the optical path of the fluorescence emission or the stimulated emission 25 depending upon the kind of the laser stimulating ray source to be used.

The filter 28a is used for reading fluorescence emission released from fluorescent substance contained in the sample 22 upon being excited using the first laser stimulating ray source 1 and has a property to cut off light having a wavelength of 640 nm but transmit light having a wavelength longer than 640 nm.

The filter 28b is used for reading fluorescence emission released from fluorescent substance contained in the sample 22 upon being excited using the second laser stimulating ray source 2 and has a property to cut off light having a wavelength of 532 nm but transmit light having a wavelength longer than 532 nm.

The filter 28c is used for reading fluorescence emission released from fluorescent substance contained in the sample 22 upon being excited using the third laser stimulating ray source 3 and has a property to cut off light having a wavelength of 473 nm but transmit light having a wavelength longer than 473 nm.

The filter 28d is used in the case where the sample 22 is a stimulable phosphor sheet for reading stimulated emission released from stimulable phosphor contained in the stimulable phosphor sheet upon being excited using the first laser stimulating ray source 1 and has a property to transmit only light having a wavelength corresponding to that of stimulated emission emitted from stimulable phosphor but cut off light having a wavelength of 640 nm.

Therefore, in accordance with the kind of a stimulating ray source to be used, namely, depending upon whether the image to be read is a fluorescent image or an image regarding locational information of a radioactively labeling substance and the kind of fluorescent substance labeling a specimen, one of these filters 28a, 28b, 28c, 28d is selectively used, thereby cutting light of wavelengths which cause noise.

After fluorescence emission or stimulated emission 25 passes through one of the filters 28a, 28b, 28c, 28d, whereby light of a predetermined wavelength region is cut, the fluorescence emission or the stimulated emission 25 advances to a mirror 29 and is reflected thereby to be condensed by a lens 30.

The lens 19 and the lens 30 constitute a confocal optical system. The reason for employing a confocal optical system is to enable fluorescence emission emitted from a minute spot formed on a slide glass plate to be read with a high S/N ratio when the sample 22 is a micro-array including the slide glass plate 23 as a substrate.

A confocal switching member 31 is provided at the focal point of the lens 30.

Figure 2:
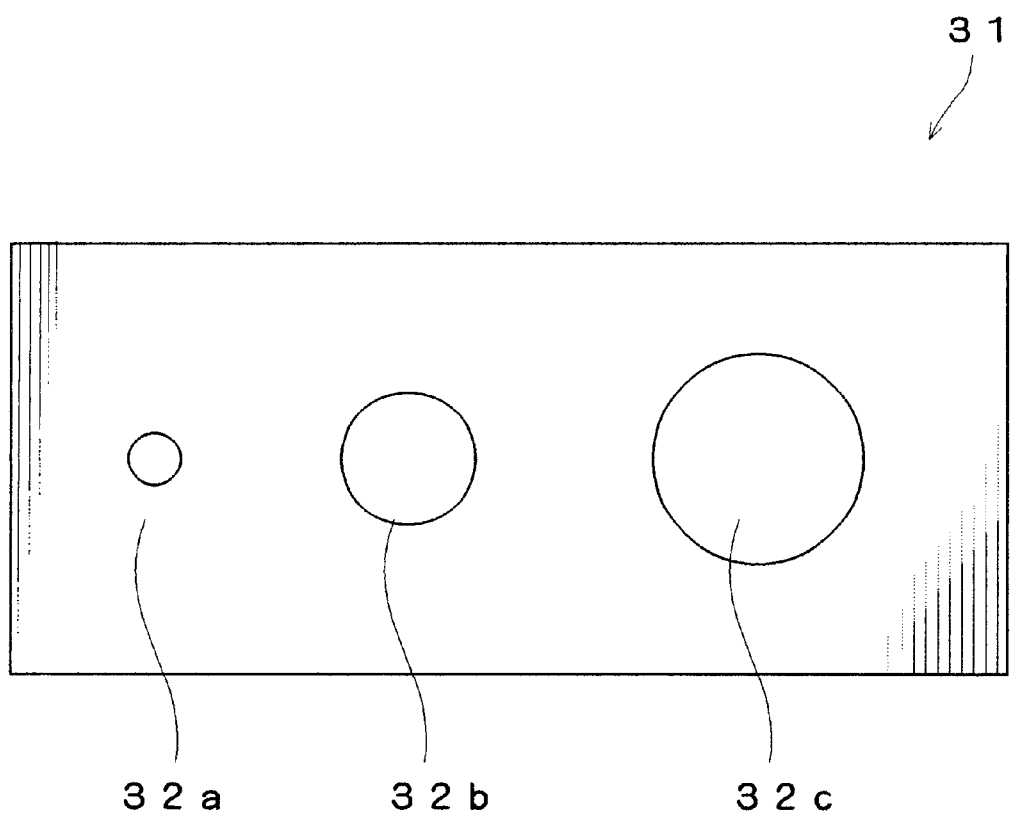
FIG. 2 is a schematic front view showing a confocal switching member.

FIG. 2 is a schematic front view showing the confocal switching member 31.

As shown in FIG. 2, the confocal switching member 31 is formed plate-like and with three pinholes 32a, 32b, 32c.

The pinhole 32a having the smallest diameter is located in a light path of fluorescence emission emitted from the micro-array when the sample is a micro-array including a slide glass plate as a substrate and the pinhole 32c having the largest diameter is located in a light path of fluorescence emission emitted from a transfer support when the sample is a fluorescence sample including a transfer support as a substrate.

Further, the pinhole 32b having an intermediate diameter is located in a light path of a stimulated emission released from a stimulable phosphor layer when the sample is a stimulable phosphor sheet.

In this manner, the confocal switching member 31 is provided at the focal point of the lens 30 and the pinhole 32a having the smallest diameter is located in the light path of fluorescence emission when the sample 22 is a micro-array including a slide glass plate as a substrate. This is because when the sample 22 is a micro-array including a slide glass plate 23 as a substrate, fluorescence emission is emitted from the surface of the slide glass plate when the fluorescent dye is excited with the laser beam 4 and the depth of the light emitting points in the slide glass plate is substantially constant, so that it is preferable to use a confocal optical system to focus an image on the pinhole 32a having the smallest diameter for improving the S/N ratio.

On the other hand, the pinhole 32c is located in the light path of fluorescence emission when the sample 22 is a fluorescence sample including a transfer support as a substrate. This is because when the sample 22 is a fluorescence sample including a transfer support as a substrate, the positions of the light emitting points fluctuate in the depth direction when the fluorescent dye is excited with the laser beam 4 because the fluorescent substance is distributed in the depth direction of the transfer support, so that it is impossible to focus an image on a pinhole having a small diameter even when a confocal optical system is used, and a fluorescent light emitted from the specimen is cut if a pinhole having a small diameter is used, whereby signals having a sufficient intensity cannot be obtained and, therefore, it is necessary to use the pinhole 32c having the largest diameter.

Further, in the case where the sample 22 is a stimulable phosphor sheet, the pinhole 32b having an intermediate diameter is located in a light path of a stimulated emission. This is because when the sample 22 is a stimulable phosphor sheet, the positions of the light emitting points fluctuate in the depth direction when a stimulable phosphor contained in the stimulable phosphor layer is excited with the laser beam 4 because the light emitting points of a stimulated emission are distributed in the depth direction of the stimulable phosphor layer, so that it is impossible to focus an image on a pinhole having a small diameter even when a confocal optical system is used, and the stimulated emission emitted from the specimen is cut if a pinhole having a small diameter is used, whereby signals having a sufficient intensity cannot be obtained by photoelectrically detecting the stimulated emission but the distribution of the light emitting points in the depth direction and the fluctuation in positions of the light emitting points in the depth direction are no so great as those for reading a fluorescent image carried in the transfer support or the gel support and, therefore, it is preferable to employ the pinhole 32b having an intermediate diameter.

The fluorescence emission or stimulated emission 25 passing through the confocal switching member 31 is photoelectrically detected by a photomultiplier 33, thereby producing analog data.

The analog image data produced by the photomultiplier 33 are converted by an A/D converter 34 into digital image data and the digital image data are forwarded to a data processing apparatus 35.

Figure 3:
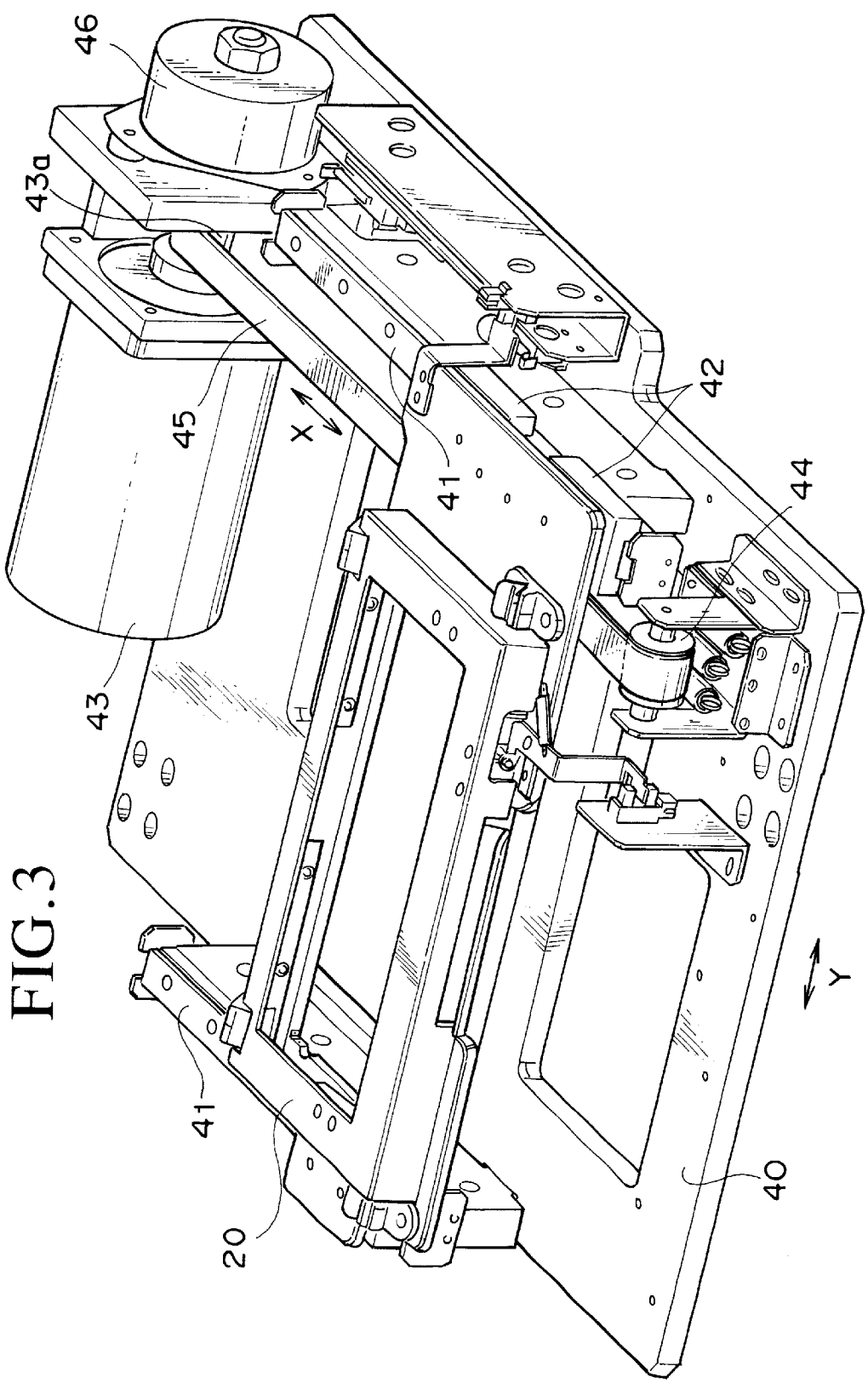
FIG. 3 is a schematic perspective view showing the details of a main scanning mechanism that is part of a scanning mechanism of a sample stage.

FIG. 3 is a schematic perspective view showing the details of a main scanning mechanism that is part of a scanning mechanism of a sample stage.

Figure 4:
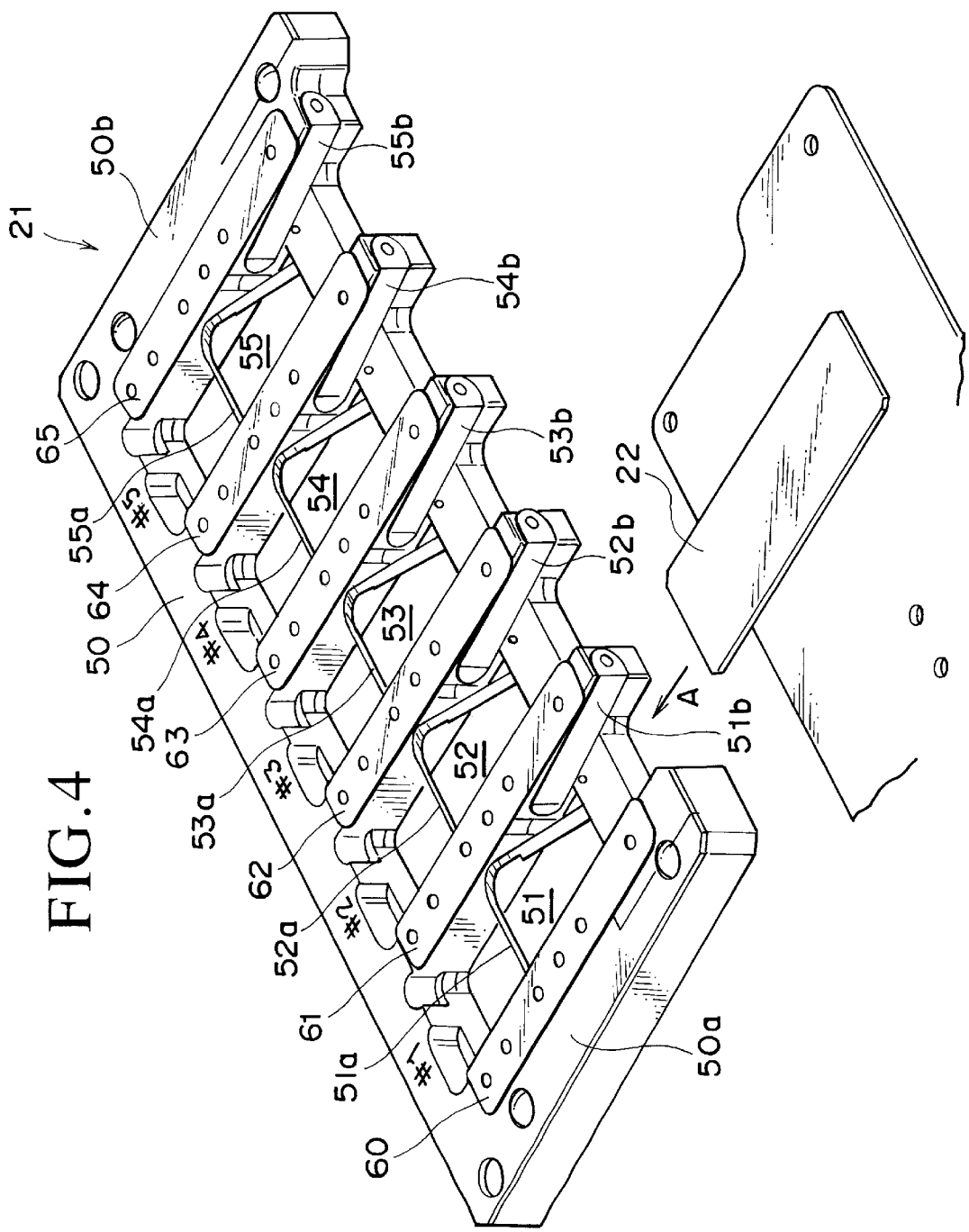
FIG. 4 is a schematic perspective view showing a sample carrier to be set on a sample stage of a scanner which is a preferred embodiment of the present invention.

As shown in FIG. 3, a pair of guide rails 41, 41 are fixed on the movable base plate 40 movable in a sub-scanning direction indicated by the arrow Y in FIG. 4 by a sub-scanning motor (not shown) and the sample stage 20 is fixed to three side members 42, 42 (only two shown in FIG. 3.) slidably mounted on the pair of guide rails 41, 41.

As shown in FIG. 3, a main scanning motor 43 is fixed on the movable base plate 40. A timing belt 45 wound around a pulley 44 is wound around the output shaft 43a of the main scanning motor 43 and a rotary encoder 46 is secured to the output shaft 43a of the main scanning motor 43.

Therefore, the sample stage 20 can be reciprocated along the pair of guide rails 41, 41 in the main scanning direction indicated by the arrow X in FIG. 3 by driving the main scanning motor 43 and the sample stage 20 can be two-dimensionally moved by further moving the movable base plate 40 in the sub-scanning direction by the sub-scanning motor (not shown), thereby enabling the whole surface of the sample 22 set on the sample stage 20 to be scanned with the laser beam 4.

The position of the sample stage 20 can be monitored by the rotary encoder 46.

FIG. 4 is a schematic perspective view showing the sample carrier 21 to be set on the sample stage 20 of an image reading apparatus of a digital image data producing system which is a preferred embodiment of the present invention and in FIG. 4, the sample carrier 21 is viewed from the backside, namely, from the side thereof to be placed on the sample stage 20.

As shown in FIG. 4, the sample carrier 21 includes a frame member 50 formed by processing a single plate member and the frame member 50 is formed with five openings into which the sample 22 can be set, namely, a first opening 51, a second opening 52, a third opening 53, a fourth opening 54 and a fifth opening 55.

Rectangular plate members 60, 61, 62, 63, 64, 65 are respectively mounted on the surface of the frame member 50 so that portions thereof 20 on the side of the first opening 51, the second opening 52, the third opening 53, the fourth opening 54 and the fifth opening 55 are located along the longitudinal directions of the first opening 51, the second opening 52, the third opening 53, the fourth opening 54 and the fifth opening 55 and project above the first opening 51, the second opening 52, the third opening 53, the fourth opening 54 and the fifth opening 55.

As shown in FIG. 4, L-shaped leaf springs 51a, 52a, 53a, 54a, 55a are respectively mounted in the first opening 51, the second opening 52, the third opening 53, the fourth opening 54 and the fifth opening 55 so as to produce a spring force thereof toward the rear side of the sample carrier 21. Leaf springs 51b, 52b, 53b, 54b, 55b are further mounted on the inner wall portions of the first opening 51, the second opening 52, the third opening 53, the fourth opening 54 and the fifth opening 55 respectively for aligning the sample set in the first opening 51, the second opening 52, the third opening 53, the fourth opening 54 and the fifth opening 55 along opposite inner wall portions.

The sample carrier 21 is constituted to be set on the sample stage so that the opposite side portions 50a, 50b of the frame member 50 are placed on the sample stage 20.

When micro-arrays, the samples 22, each including a slide glass plate as a substrate are to be set in the sample carrier 21, the samples 22 are inserted into the first opening 51, the second opening 52, the third opening 53, the fourth opening 54 and the fifth opening 55 in the direction indicated by the arrow A in FIG. 4.

Since the leaf springs 51b, 52b, 53b, 54b, 55b are further mounted on the inner wall portions of the first opening 51, the second opening 52, the third opening 53, the fourth opening 54 and the fifth opening 55 respectively, the samples 22 are aligned along the opposite inner wall portions in the first opening 51, the second opening 52, the third opening 53, the fourth opening 54 and the fifth opening 55.

At the same time, the bend portions of the L-shaped leaf springs 51a, 52a, 53a, 54a, 55a abut against the samples 22 inserted in the first opening 51, the second opening 52, the third opening 53, the fourth opening 54 and the fifth opening 55 and the samples 22 are biased by the spring force of the leaf springs 51a, 52a, 53a, 54a, 55a onto the surfaces of the plate members 60, 61, 62, 63, 64, 65 mounted so that portions thereof on the side of the first opening 51, the second opening 52, the third opening 53, the fourth opening 54 and the fifth opening 55 are located along the longitudinal directions of the first opening 51, the second opening 52, the third opening 53, the fourth opening 54 and the fifth opening 55 and project above the first opening 51, the second opening 52, the third opening 53, the fourth opening 54 and the fifth opening 55, thereby being held in the sample carrier 21.

In the sample carrier 21 shown in FIG. 4, the plate members 60, 61, 62, 63, 64, 65 are mounted on the surface of the frame member 50 so that portions thereof on the side of the first opening 51, the second opening 52, the third opening 53, the fourth opening 54 and the fifth opening 55 are located along the longitudinal directions of the first opening 51, the second opening 52, the third opening 53, the fourth opening 54 and the fifth opening 55 and project above the first opening 51, the second opening 52, the third opening 53, the fourth opening 54 and the fifth opening 55 and the samples 22 are biased by the spring force of the leaf springs 51a, 52a, 53a, 54a, 55a onto the surfaces of the plate members 60, 61, 62, 63, 64, 65, thereby being held in the sample carrier 21.

On the other hand, the sample carrier 21 is set on the sample stage so that the opposite side portions 50a, 50b of the frame member 50 formed by processing a single plate member are placed on the sample stage 20.

Therefore, since the surfaces of the plate members 60, 61, 62, 63, 64, 65 on which the samples 22 are supported and the surface of the sample stage 20 on which the sample carrier 21 is supported are always located in the same plane, five samples 22 can be set on the sample stage 20 with a constant positional relationship between themselves and the sample stage 20 without need for troublesome adjustment of the position of the sample carrier 21.

Further, since five samples 22 can be set on the sample stage 20 with a constant positional relationship between themselves and the sample stage 20 merely by mounting the plate members 60, 61, 62, 63, 64, 65 on the surface of the frame member 50 formed by processing a single plate member, the cost of the sample carrier 21 can be markedly reduced.

Figure 5:
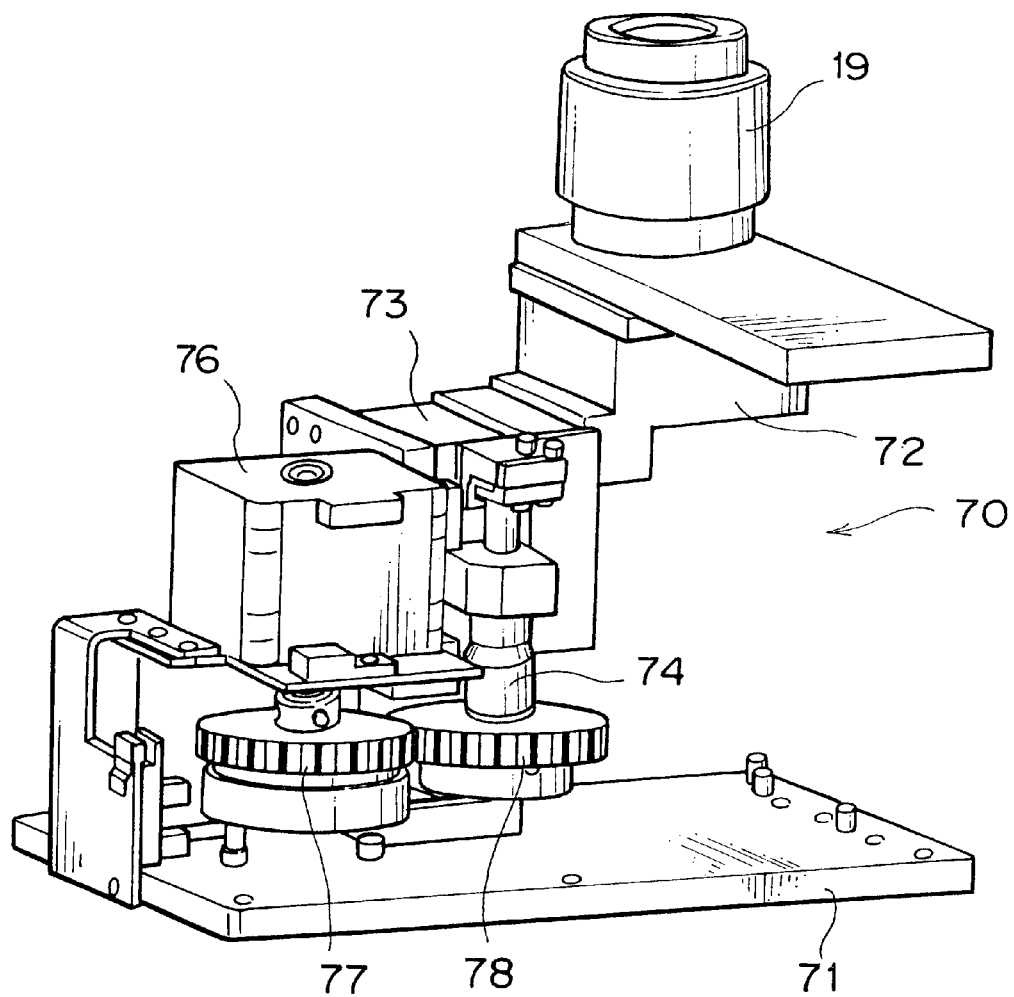
FIG. 5 is a schematic perspective view showing a lens height position adjusting apparatus for adjusting a height position of a lens provided in an optical head.
Figure 6:
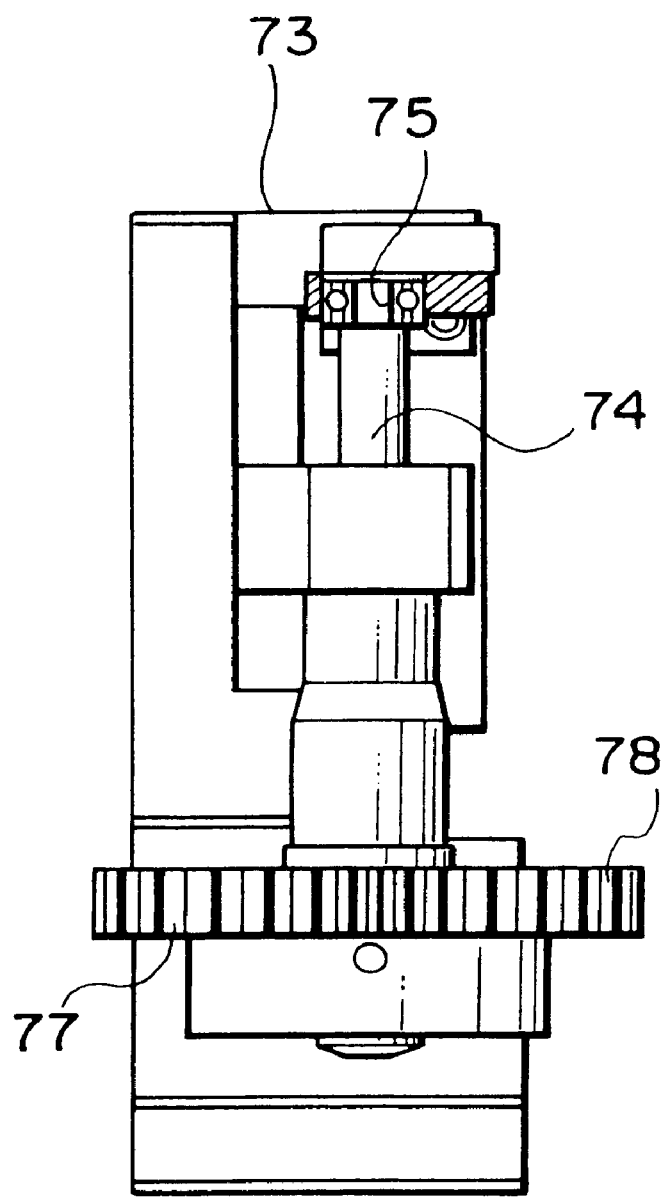
FIG. 6 is a schematic partially cut-out side view of a micrometer head and a moving direction regulating member.

FIG. 5 is a schematic perspective view showing a lens height position adjusting apparatus for adjusting the height position of the lens 19 provided in an optical head 15 and FIG. 6 is a schematic partially cut-out side view of a micrometer head and a moving direction regulating member.

As shown in FIG. 5, a lens height position adjusting apparatus 70 includes a lens base provided on a base plate 71 fixed to the main body of the scanner and adapted for supporting the lens 19 and the lens base is mounted on a moving direction regulating member 73 whose movement is restricted only in the vertical direction.

As shown in FIGS. 5 and 6, the lens height position adjusting apparatus 70 further includes a micrometer head 74 and the micrometer head 74 abuts against a ball bearing 75 provided in the moving direction regulating member 73.

The lens height position adjusting apparatus 70 further includes a stepping motor 76 and the rotation of the stepping motor 76 is transmitted to the micrometer head 74 via a gear 77 and a gear 78. In this embodiment, when the stepping motor 76 is rotated by one revolution, the micrometer head 74 is moved vertically by 500 micrometers.

According to the thus constituted lens height position adjusting apparatus 70 shown in FIGS. 5 and 6, since the base 71 to which the lens 19 is secured is mounted on the moving direction regulating member 73 whose movement is restricted only in the vertical direction, the micrometer head 74 abuts against the ball bearing 75 provided in the moving direction regulating member 73 and the moving direction regulating member 73 is moved vertically directly by the micrometer head 74, it is possible to precisely adjust the height position of the lens 19.

Further, since the micrometer head 74 abuts against the ball bearing 75 provided in the moving direction regulating member 73, even if the height position of the lens 19 is frequently and repeatedly adjusted, it is possible to effectively prevent the portion against which the micrometer abuts from being worn.

Figure 7:
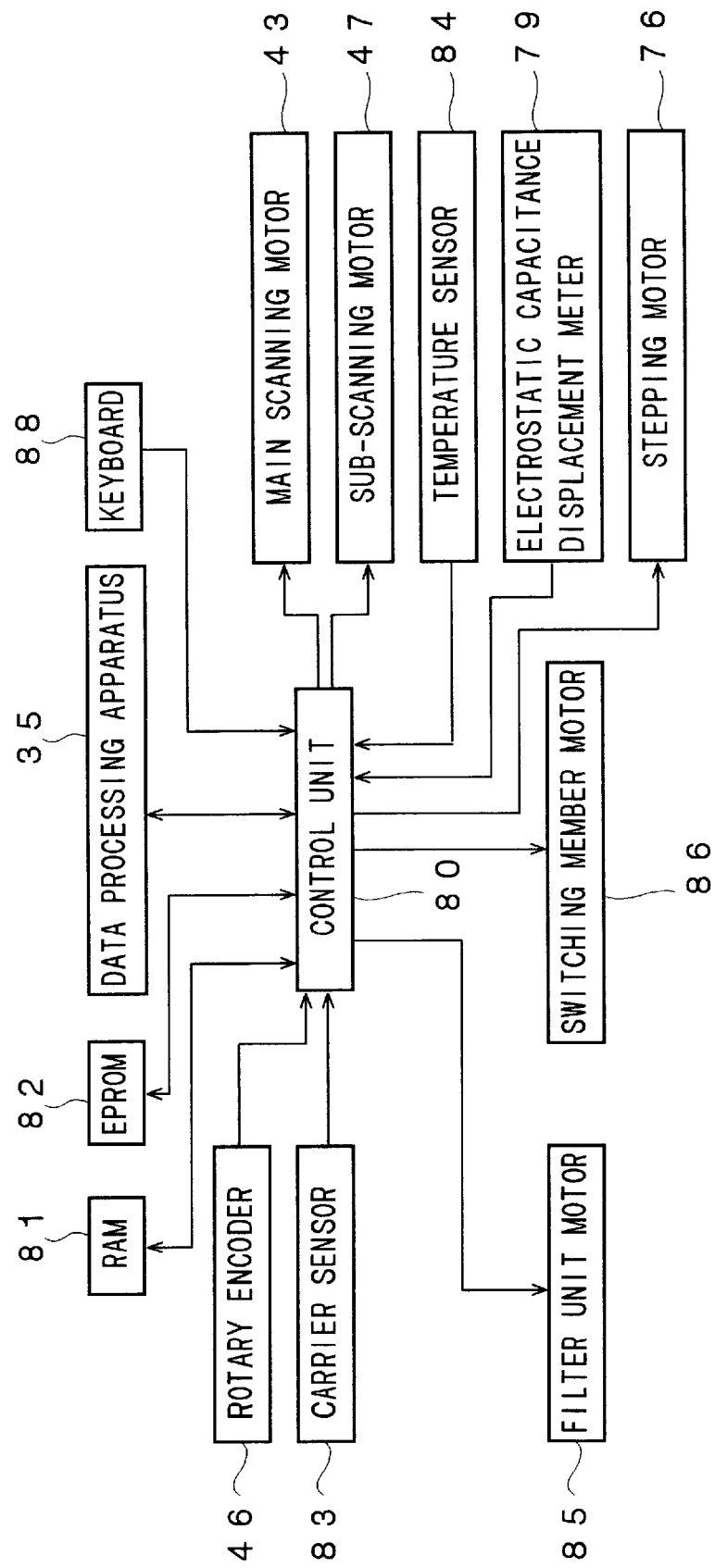
FIG. 7 is a block diagram of a detection system, a drive system, an input system and a control system of a scanner which is a preferred embodiment of the present invention.

FIG. 7 is a block diagram of a detection system, a drive system, an input system and a control system of the scanner which is a preferred embodiment of the present invention.

As shown in FIG. 7, the control system of the scanner includes a control unit 80, a RAM 81, an EPROM 82 and the data processing apparatus 35.

As shown in FIG. 7, the detection system of the scanner includes the rotary encoder 46, a carrier sensor 83 for detecting the kind of a sample carrier 21 carrying the sample 22 set on the sample stage, a temperature sensor 84 and an electrostatic capacitance displacement meter 79 described in detail later.

As shown in FIG. 7, the drive system of the scanner includes a filter unit motor 85 for moving the filter unit 27, a switching member motor 86 for moving the confocal switching member 31, the main scanning motor 43 for reciprocating the sample stage 20 in the main scanning direction, a sub-scanning motor 47 for intermittently moving the sample stage 20 in the sub-scanning direction, and the stepping motor 76 for moving the lens 19 of the optical head 15 along the optical path of fluorescence emission or stimulated emission.

As shown in FIG. 7, the input system of the scanner includes a keyboard 88.

In the thus constituted scanner, distance data representing distance between the micro-array including a slide glass plate as a substrate to be set in the sample carrier 21 and the lens 19 of the optical head 15 are first produced and stored in the EPROM 82.

Figure 8:
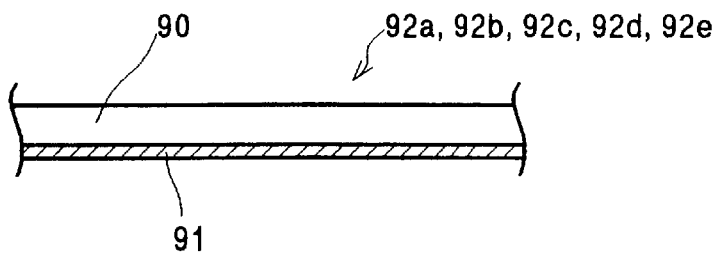
FIG. 8 is a schematic longitudinal cross-sectional view of a distance measuring device used for producing distance data representing distance between a micro-array and a lens of an optical head.
Figure 9:
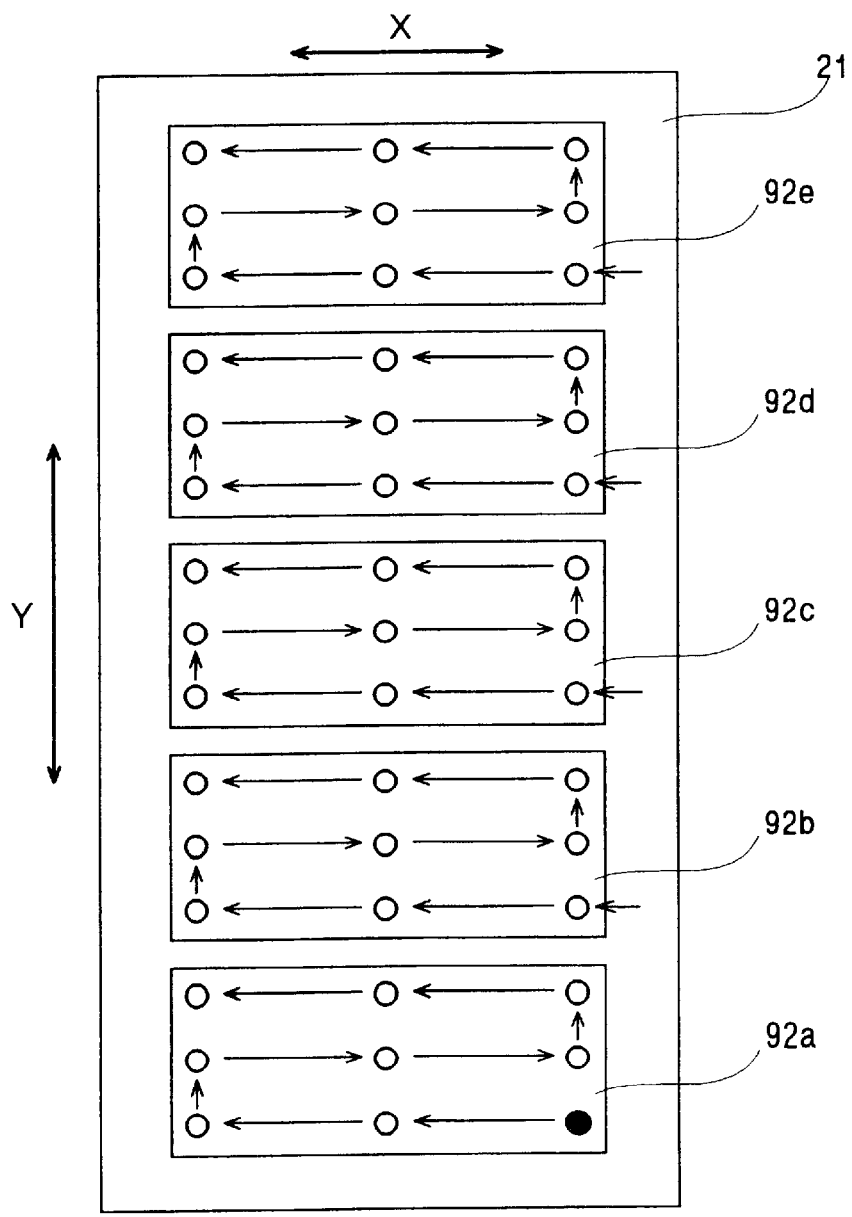
FIG. 9 is a schematic plan view showing a sample carrier when distance data representing distance between a micro-array and a lens of an optical head are produced.

FIG. 8 is a schematic longitudinal cross-sectional view of a distance measuring device used for producing distance data representing distance between the micro-array and the lens 19 of the optical head 15 and FIG. 9 is a schematic plan view showing the sample carrier 21 when distance data representing distance between the micro-array and the lens 19 of the optical head 15 are produced.

As shown in FIG. 8, each of distance measuring devices 92a, 92b, 92c, 92d, 92e used for producing distance data representing distance between the micro-array and the lens 19 of the optical head 15 is constituted as a slide glass plate 90 formed with a chromium layer 91 formed by sputtering on the whole surface thereof. When distance data representing distance between the micro-array and the lens 19 of the optical head 15 are to be produced, the distance measuring device 92a is set in a first opening 51, which is a first sample position in the sample carrier 21, the distance measuring device 92b is set in a second opening 52 which is a second sample position in the sample carrier 21, the distance measuring device 92c is set in a third opening 53 which is a third sample position in the sample carrier 21, the distance measuring device 92d is set in a fourth opening 54, which is a fourth sample position in the sample carrier 21, and the distance measuring device 92e is set in a fifth opening 55 in the sample carrier so that the chromium layers 91 are located on the side of the lens 19 of the optical head 15.

Figure 10:
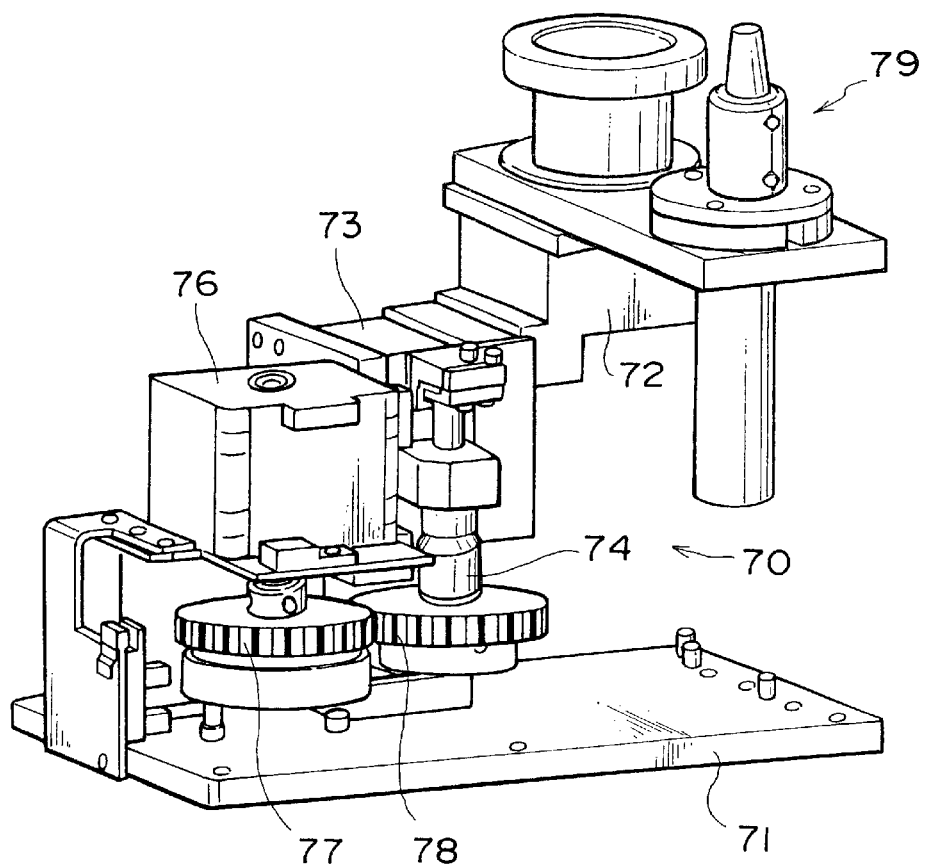
FIG. 10 is a schematic perspective view showing a lens height position adjusting apparatus for adjusting the height position of a lens provided in an optical head when distance data representing distance between a micro-array and a lens of an optical head are produced.

FIG. 10 is a schematic perspective view showing the lens height position adjusting apparatus for adjusting the height position of the lens 19 provided in the optical head 15 when distance data representing distance between the micro-array and the lens 19 of the optical head 15 are produced.

As shown in FIG. 10, when distance data representing distance between the micro-array and the lens 19 of the optical head 15 are to be produced, the lens 19 is removed from the lens base 72 and the electrostatic capacitance displacement meter 79 is mounted on the upper surface of the lens base 72.

When the electrostatic capacitance displacement meter 79 is mounted on the upper surface of the lens base 72, a distance measurement instruction signal is input by the operator together with a temperature setting signal through the keyboard 88. In this embodiment, the temperature in the scanner is set to 15° C. and distance data representing the distance between the micro-arrays set in the first opening 51 to the fifth opening 55 and the lens 19 of the optical head 15 are produced.

The distance measurement instruction signal and the temperature setting signal are input to the control unit 80 and when the control unit 80 confirms that the temperature in the scanner has become 15° C. based on a temperature detection signal received from the temperature sensor 84, the control unit 80 outputs drive signals to the main scanning motor 43 and the sub-scanning motor 47, thereby causing them to move the sample stage 20 in the main scanning direction and the sub-scanning direction so that the tip end portion of the electrostatic capacitance displacement meter 79 is moved along the surface of the chromium layer 91 as indicated by arrows in FIG. 9.

The electrostatic capacitance displacement meter 79 is moved along the surfaces of the chromium layers 91 formed on the distance measuring devices 92a, 92b, 92c, 92d, 92e set in the five openings 51, 52, 53, 54, 55 in the sample carrier 21 as indicated by arrows in FIG. 9 with a small clearance held between the tip end portion thereof and the surfaces of the chromium layers 91, and displacements of the positions of measurement points indicated by white circles on the distance measuring devices 92a, 92b, 92c, 92d, 92e in FIG. 9 with respect to a reference point indicated by a black circle on the distance measuring device 92a set in the first opening 51, which is the first sample position, in FIG. 9 are measured by the electrostatic capacitance displacement meter 79 and output to the control unit 80.

The control unit 80 stores the displacements of the positions of the measurement points indicated by the white circles on the distance measuring devices 92a, 92b, 92c, 92d, 92e in FIG. 9 with respect to the reference point indicated by the black circle in FIG. 9 input from the electrostatic capacitance displacement meter 79 in the RAM 81.

When the displacements of the positions of measurement points indicated by white circles on the distance measuring devices 92a, 92b, 92c, 92d, 92e in FIG. 9 with respect to the reference point indicated by the black circle in FIG. 9 are measured by the electrostatic capacitance displacement meter 79 and stored in the RAM 81 in this manner, the operator uses the keyboard 88 to input a temperature setting signal for setting the temperature in the scanner to 25° C. together with a distance measurement instruction signal for measuring the displacement in the position of the reference point on the distance measuring device 92a set in the first opening 51, which is the first sample position at 25° C., with respect to the position of the reference point on the distance measuring device 92a at 15° C. and the displacements of the positions of the measurement points on the distance measuring devices 92a, 92b, 92c, 92d, 92e at 25° C. with respect to the position of the reference point on the distance measuring device 92a at 15° C.

The distance measurement instruction signal and the temperature setting signal are input to the control unit 80 and when the control unit 80 confirms that the temperature in the scanner has become 25° C. based on a temperature detection signal received from the temperature sensor 84, the control unit 80 outputs drive signals to the main scanning motor 43 and the sub-scanning motor 47, thereby causing them to move the sample stage 20 in the main scanning direction and the sub-scanning direction so that the tip end portion 79a of the electrostatic capacitance displacement meter 79 is moved along the surface of the chromium layer 91 as indicated by arrows in FIG. 9.

As a result, the displacement in the position of the reference point on the distance measuring device 92a set in the first opening 51, which is the first sample position, at 25° C. with respect to the position of the reference point on the distance measuring device 92a at 15° C. and the displacements of the positions of the measurement points indicated by the white circles on the distance measuring devices 92a, 92b, 92c, 92d, 92e at 25° C. with respect to the position of the reference point on the distance measuring device 92a at 15° C. are measured by the electrostatic capacitance displacement meter 79 and output to the control unit 80.

The control unit 80 stores the displacement in the position of the reference point on the distance measuring device 92a at 25° C. with respect to the position of the reference point on the distance measuring device 92a at 15° C. and the displacements of the positions of the measurement points indicated by the white circles on the distance measuring devices 92a, 92b, 92c, 92d, 92e at 25° C. with respect to the position of the reference point on the distance measuring device 92a at 15° C. input from the electrostatic capacitance displacement meter 79 in the RAM 81.

When the displacement in the position of the reference point indicated by the black circle in FIG. 9 on the distance measuring device 92a at 25° C. with respect to the position of the reference point on the distance measuring device 92a at 15° C. and the displacements of the positions of the measurement points indicated by white circles on the distance measuring devices 92a, 92b, 92c, 92d, 92e at 25° C. with respect to the position of the reference point on the distance measuring device 92a at 15° C. are stored in the RAM 81 under the condition that the temperature in the scanner is set to 25° C. in this manner, the operator uses the keyboard 88 to input a temperature setting signal for setting the temperature in the scanner to 35° C. together with a distance measurement instruction signal instructing for measuring the displacement in the position of the reference point on the distance measuring device 92a set in the first opening 51, which is the first sample position, at 35° C. with respect to the position of the reference point on the distance measuring device 92a at 15° C. and the displacements of the positions of the measurement points indicated by the white circles on the distance measuring devices 92a, 92b, 92c, 92d, 92e at 35° C. with respect to the position of the reference point on the distance measuring device 92a at 15° C.

The distance measurement instruction signal and the temperature setting signal are input to the control unit 80 and when the control unit 80 confirms that the temperature in the scanner has become 35° C. based on a temperature detection signal received from the temperature sensor 84, the control unit 80 outputs drive signals to the main scanning motor 43 and the sub-scanning motor 47, thereby causing them to move the sample stage 20 in the main scanning direction and the sub-scanning direction so that the tip end portion 79a of the electrostatic capacitance displacement meter 79 is moved along the surface of the chromium layer 91 as indicated by arrows in FIG. 9.

As a result, the displacement in the position of the reference point on the distance measuring device 92a set in the first opening 51, which is the first sample position, at 35° C. with respect to the position of the reference point on the distance measuring device 92a at 15° C. and the displacements of the positions of the measurement points indicated by the white circles on the distance measuring devices 92a, 92b, 92c, 92d, 92e at 35° C. with respect to the position of the reference point on the distance measuring device 92a at 15° C. are measured by the electrostatic capacitance displacement meter 79 and output to the control unit 80.

The control unit 80 stores the displacement in the position of the reference point on the distance measuring device 92a at 35° C. with respect to the position of the reference point on the distance measuring device 92a at 15° C. and the displacements of the positions of the measurement points indicated by the white circles on the distance measuring devices 92a, 92b, 92c, 92d, 92e at 35° C. with respect to the position of the reference point on the distance measuring device 92a at 15° C. input from the electrostatic capacitance displacement meter 79 in the RAM 81.

When, based on the results of measurement by the electrostatic capacitance displacement meter 79, the displacement in the position of the reference point indicated by the black circle on the distance measuring device 92a in FIG. 9 at 25° C. and 35° C. with respect to the position of the reference point on the distance measuring device 92a at 15° C. and the displacements of the positions of the measurement points indicated by the white circles on the distance measuring devices 92a, 92b, 92c, 92d, 92e at 15° C., 25° C. and 35° C. with respect to the position of the reference point on the distance measuring device 92a at 15° C. are stored in the RAM 81, the control unit 80 first reads from the RAM 81 the displacement in the position of the reference point indicated by the black circle on the distance measuring device 92a in FIG. 9 at 25° C. and 35° C. with respect to the position of the reference point on the distance measuring device 92a at 15° C., and the displacements of the positions of the measurement points indicated by the white circles on the distance measuring devices 92a, 92b, 92c, 92d, 92e at 35° C. with respect to the position of the reference point on the distance measuring device 92a at is 15° C. and linearly regresses changes in the displacements of the positions of the measurement points on the distance measuring devices 92a, 92b, 92c, 92d, 92e with respect to the temperature in the scanner by the least square method, thereby calculating a temperature coefficient for each measurement point.

The control unit 80 then calculates the average value of the temperature coefficients of all measurement points on the distance measuring device 92a and determines the calculated average value of the temperature coefficients as a temperature coefficient when the sample 22 is set in the first opening 51, which is the first sample position, namely, a temperature coefficient of the first sample position in the sample carrier 21, and stores it in the EPROM 82.

Similarly, the control unit 80 calculates the average value of the temperature coefficients of all measurement points on the distance measuring device 92b and determines the calculated average value of the temperature coefficients as a temperature coefficient when the sample 22 is set in the second opening 52, which is the second sample position, namely, a temperature coefficient of the second sample position in the sample carrier 21, calculates the average value of the temperature coefficients of all measurement points on the distance measuring device 92c and determines the calculated average value of the temperature coefficients as a temperature coefficient when the sample 22 is set in the third opening 53, which is the third sample position, namely, a temperature coefficient of the third sample position in the sample carrier 21, calculates the average value of the temperature coefficients of all measurement points on the distance measuring device 92d and determines the calculated average value of the temperature coefficients as a temperature coefficient when the sample 22 is set in the fourth opening 54, which is the fourth sample position, namely, a temperature coefficient of the fourth sample position in the sample carrier 21, and calculates the average value of the temperature coefficients of all measurement points on the distance measuring device 92e and determines the calculated average value of the temperature coefficients as a temperature coefficient when the sample 22 is set in the fifth opening 55, which is the fifth sample position, namely, a temperature coefficient of the fifth sample position in the sample carrier 21. The control unit 80 then stores the thus calculated temperature coefficients in the EPROM 82.

The control unit 80 further calculates the average value of the displacements in the positions of the nine measurement points on the distance measuring device 92a set in the first opening 51, which is the first sample position in the sample carrier 21 when the temperature in the scanner is set to 25° C. with respect to the reference point at 15° C. and determines the calculated average value of the displacements as a distance correction value of the positions of the nine measurement points when the sample 22 is set in the first opening 51, which is the first sample position in the sample carrier 21, namely, a distance correction value ΔD1 of the first sample position, and stores it in the EPROM 82.

Similarly, the control unit 80 determines the average value of the displacements in the positions of the nine measurement points on the distance measuring device 92b when the temperature in the scanner is set to 25° C. with respect to the reference point at 15° C. as a distance correction value of the positions of the nine measurement points when the sample 22 is set in the second opening 52, which is the second sample position in the sample carrier 21, namely, a distance correction value ΔD2 of the second sample position, determines the average value of the displacements in the positions of the nine measurement points on the distance measuring device 92c when the temperature in the scanner is set to 25° C. with respect to the reference point at 15° C. as a distance correction value of the positions of the nine measurement points when the sample 22 is set in the third opening 53, which is the third sample position in the sample carrier 21, namely, a distance correction value ΔD3 of the third sample position, determines the average value of the displacements in the positions of the nine measurement points on the distance measuring device 92d when the temperature in the scanner is set to 25° C. with respect to the reference point at 15° C. as a distance correction value of the positions of the nine measurement points when the sample 22 is set in the fourth opening 54, which is the fourth sample position in the sample carrier 21, namely, a distance correction value ΔD4 of the fourth sample position, determines the average value of the displacements in the positions of the nine measurement points on the distance measuring device 92e when the temperature in the scanner is set to 25° C. with respect to the reference point at 15° C. as a distance correction value of the positions of the nine measurement points when the sample 22 is set in the fifth opening 55, which is the fifth sample position in the sample carrier 21, namely, a distance correction value ΔD5 of the fifth sample position, and stores the thus determined distance correction values in the EPROM 82.

The control unit 80 further reads from the RAM 81 displacements in the positions of the nine measurement points on the distance measuring device 92a set in the first opening 51, which is the first sample position in the sample carrier 21, with respect to the reference point at 15° C. and stores them as first measurement point displacement data V1 in the EPROM 82.

Similarly, the control unit 80 determines displacements in the positions of the nine measurement points on the distance measuring device 92b with respect to the reference point at 15° C. stored in the RAM 81 as second measurement point displacement data V2, determines displacements in the positions of the nine measurement points on the distance measuring device 92c with respect to the reference point at 15° C. stored in the RAM 81 as third measurement point displacement data V3, determines displacements in the positions of the nine measurement points on the distance measuring device 92d with respect to the reference point at 15° C. stored in the RAM 81 as fourth measurement point displacement data V4, determines displacements in the positions of the nine measurement points on the distance measuring device 92e with respect to the reference point at 15° C. stored in the RAM 81 as fifth measurement point displacement data V5, and stores the thus determined measurement point displacement data in the EPROM 82.

When the temperature coefficient K1 of the first sample position to the temperature coefficient K5 of the fifth sample position, the distance correction value ΔD1 of the first sample position to the distance correction value ΔD5 of the fifth sample position and the measurement point displacement data V1 of the first sample position to the measurement point displacement data V5 of the fifth sample position are stored in the EPROM 82 in this manner, the operator removes the distance measuring devices 92a, 92b, 92c, 92d, 92e from the openings 51, 52, 53, 54, 55 in the sample carrier 21.

The operator then sets in the first opening 51 in the sample carrier 21 a focus position determination device having a spot containing Fluor-X (registered trademark), Cy3 (registered trademark) and Cy5 (registered trademark) formed at a reference position on the slide glass plate corresponding to the reference point indicated by the black circle in FIG. 9 on the distance measuring device 92a.

Figure 11:
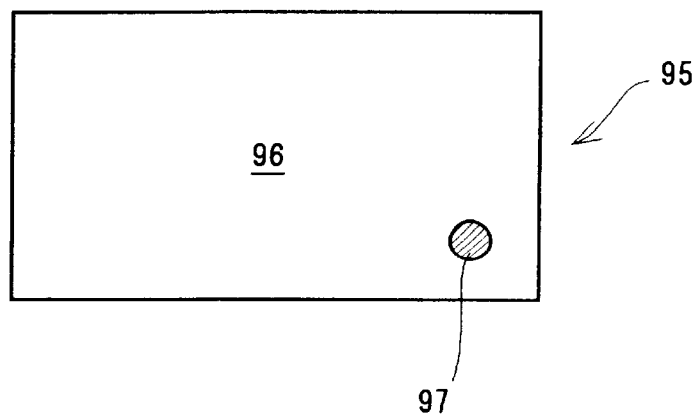
FIG. 11 is a schematic front view showing a focus position determination device.

FIG. 11 is a schematic front view showing the focus position determination device.

As shown in FIG. 11, the focus position determination device 95 is constituted as a slide glass plate 96, and a spot 97 containing Fluor-X (registered trademark), Cy3 (registered trademark) and Cy5 (registered trademark) is formed on the slide glass plate 96. The spot 97 is formed to be located at a reference position on the slide glass plate 96 corresponding to the reference point indicated by the black circle in FIG. 9 on the distance measuring device 92a when the focus position determination device 95 is set in the first opening 51 in the sample carrier 21.

When the sample carrier 21 having the focus position determination device 95 set in the first opening 51 is placed on the sample stage 20 and the operator then inputs a focus position determination signal through the keyboard 88, the focus position determination signal is sent to the control unit 80.

Upon receiving the focus position determination signal, the control unit 80 detects the position of the lens 19 of the optical head 15 and stores the detected position of the lens 19 as a zero position in the RAM 81.

The control unit 80 further outputs a drive signal to the switching member motor 86 and causes it to move the confocal switching member 31 so that the pinhole 32a having the smallest diameter is located in the optical path.

The control unit 80 then outputs a drive signal to the filter unit motor 85, thereby causing it to move the filter unit 27 so that the filter 28a having a property to cut off a light component having a wavelength of 640 nm and transmit light components having wavelengths longer than 640 nm is located in the optical path and further turns on the first laser stimulating ray source 1.

As a result, a laser beam 4 having a wavelength of 640 nm is emitted from the first laser stimulating ray source 1. The laser beam 4 passes through a collimator lens 5, thereby being made a parallel beam, and advances to the mirror 6 to be reflected thereby. The laser beam 4 reflected by the mirror 6 passes through the first dichroic mirror 7 and the second dichroic mirror 8 and enters the optical head 15.

The laser beam 4 entering the optical unit 15 is reflected by the mirror 16, passes through the hole 17 formed in the perforated mirror 18 and through the lens 19 to impinge on the focus position determination device 95.

Since the sample stage 20 is moved by the main scanning motor 43 in the main scanning direction indicated by the arrow X in FIG. 3 with a pixel pitch substantially equal to the diameter of the laser beam 4 and is moved by the sub-scanning motor 47 in the sub-scanning direction indicated by the arrow Y in FIG. 3, the whole surface of the focus position determination device 95 with the laser beam 4 having a wavelength of 640 nm.

When being irradiated with the laser beam 4, Cy5 contained in the spot 97 of the focus position determination device 95 is stimulated by the laser beam 4, thereby releasing fluorescence emission 25.

The fluorescence emission 25 released from Cy5 contained in the spot 97 passes through the lens 19, thereby being made a parallel beam, and is reflected by the perforated mirror 18, thereby entering the filter unit 27.

Since the filter unit 27 has been moved so that the filter 28a is located in the optical path, the fluorescence emission enters the filter 28a.

Since the wavelength of fluorescence emission 25 is longer than that of the laser beam 4, i.e., the stimulating ray, the laser beam 4 is cut off by the filter 28a and only fluorescence emission 25 released from the spot 97 passes through the filter 28a.

The fluorescence emission transmitted through the filter 28a is reflected by the mirror 29, condensed by the lens 30 onto the pinhole 32a having the smallest diameter and photoelectrically detected by the photomultiplier 33, thereby producing analog data.

The analog data produced by the photomultiplier 33 are converted to digital data by the A/D converter 34 and the digital data are forwarded to the data processing apparatus 35.

Figure 12:
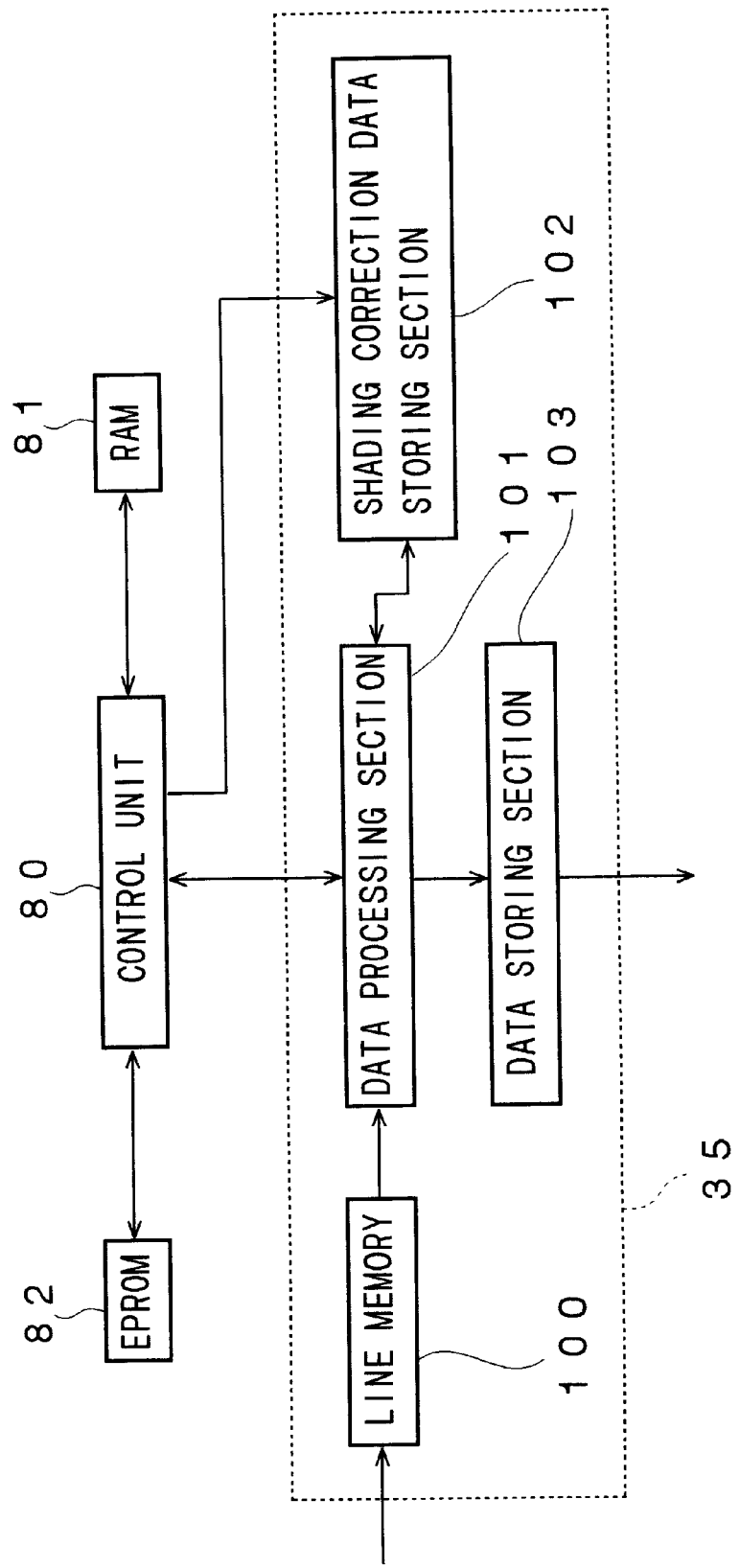
FIG. 12 is a block diagram of a data processing apparatus.

FIG. 12 is a block diagram of a data processing apparatus.

As shown in FIG. 12, the data processing apparatus 35 includes a line memory 100, a data processing section 101, a shading correction data storing section 102 for storing shading correction data and a data storing section 103 for storing digital data on which shading correction has been effected.

Digital data converted by the A/D converter 34 and output to the data processing apparatus 35 are stored in the line memory 100.

When the whole surface of the focus position determination device 95 has been scanned with the laser beam 4 having a wavelength of 640 nm, fluorescence emission 25 released from Cy5 contained in the spot 97 has been photoelectrically detected by the photomultiplier 33 and digital data converted by the A/D converter 34 have been stored in the line memory 100, the control unit 80 turns off the first laser stimulating ray source 1 and outputs a data processing signal to the data processing section 101, thereby causing it to read the digital data from the line memory 100.

The data processing section 101 integrates the signal intensity of the digital data read from the line memory 100 and outputs an integrated value of the signal intensity of fluorescence emission 25 to the control unit 80.

The control unit 80 stores the integrated value of signal intensity of fluorescence emission 25 input from the data processing section 101 of the data processing apparatus 35 so as to be related to the position of the lens 19 of the optical head 15, namely, as drive pulses applied to the stepping motor 76 in order to move the lens 19 of the optical head 15. At this time, since no drive pulse has yet been applied to the stepping motor 76, the zero position is stored in the RAM 81 together with the integrated value of signal intensity of fluorescence emission 25.

When the integrated value of signal intensity of fluorescence emission 25 has been input from the data processing section 101 of the data processing apparatus 35 and stored in the RAM 81, the control unit 80 outputs a drive pulse signal to the stepping motor 76, thereby moving the lens 19 of the optical head 15 along the optical path of fluorescence emission by 10 microns with respect to the sample stage 20 and again turns on the first laser stimulating ray source 1.

When the whole surface of the focus position determination device 95 has been scanned with the laser beam 4 having a wavelength of 640 nm, fluorescence emission 25 released from Cy5 contained in the spot 97 has been photoelectrically detected by the photomultiplier 33 and digital data converted by the A/D converter 34 have been stored in the line memory 100, the control unit 80 turns off the first laser stimulating ray source 1 and outputs a data processing signal to the data processing section 101, thereby causing it to read the digital data from the line memory 100.

The data processing section 101 integrates the signal intensity of the digital data read from the line memory 100 and outputs an integrated value of the signal intensity of fluorescence emission 25 to the control unit 80.

The control unit 80 stores the integrated value of signal intensity of fluorescence emission 25 input from the data processing section 101 of the data processing apparatus 35 so as to be related to the position of the lens 19 of the optical head 15, namely, as drive pulses applied to the stepping motor 76 in order to move the lens 19 of the optical head 15.

When the integrated value of signal intensity of fluorescence emission 25 has been input from the data processing section 101 of the data processing apparatus 35 and stored in the RAM 81, the control unit 80 outputs a drive pulse signal to the stepping motor 76, thereby moving the lens 19 of the optical head 15 along the optical path of fluorescence emission by 10 microns with respect to the sample stage 20 and again turns on the first laser stimulating ray source 1.

After the cycle including the steps of stimulating Cy5 contained in the spot 97 with the laser beam 4 having a wavelength of 640 nm, detecting fluorescence emission, producing digital data, calculating an integrated value of signal intensity of fluorescence emission 25 and storing the integrated value in the RAM 81 has been repeated a predetermined number of times, the control unit 80 calculates, based on the integrated value of signal intensity of fluorescence emission 25 stored in the RAM 81 and the positions of the lens 19 of the optical head 15, the position of the lens 19 where the maximum value of the integrated value of signal intensity of fluorescence emission 25 was produced in the form of the number of drive pulses applied to the stepping motor 76 in order to move the lens 19 of the optical head 15 from the zero position to the position where the maximum value of the integrated value of signal intensity of fluorescence emission 25 was produced and stores it in the EPROM 82 as the focus position data $P_{640}$ of the confocal optical system when the first laser stimulating ray source 1 is used, namely, when the laser beam 4 having a wavelength of 640 nm is used. At the same time, the control unit 80 stores the respective positions of the lens 19 of the optical head 15 and the corresponding integrated values of signal intensity of fluorescence emission 25 in the EPROM 82.

When in this manner the focus position data $P_{640}$ of the confocal optical system when the first laser stimulating ray source 1 is used has been determined and stored in the EPROM 82 in the form of the number of drive pulses to be applied to the stepping motor 76, the control unit 80 outputs a drive signal to the stepping motor 76, thereby causing it to return the sample stage 20 to the original position thereof and stores the position as the zero position in the RAM 81.

With the confocal optical system held so that the pinhole 32a having the smallest diameter is located in the optical path, the control unit 80 then outputs a drive signal to the stepping motor 76, thereby causing it to move the filter unit 27 so that the filter 28b having a property to cut off a light component having a wavelength of 532 nm and transmit light components having wavelengths longer than 532 nm is located in the optical path.

The laser beam 4 emitted from the second laser stimulating ray source 2 passes through a collimator lens 9, thereby being made a parallel beam, and is reflected by the first dichroic mirror 7.

The laser beam 4 reflected by the first dichroic mirror 7 passes through the second dichroic mirror 8 and enters the optical unit 15.

The laser beam 4 entering the optical unit 15 is reflected by the mirror 16, passes through the hole 17 formed in the perforated mirror 18 and through the lens 19 to impinge on the focus position determination device 95.

Since the sample stage 20 is moved by the main scanning motor 43 in the main scanning direction indicated by the arrow X in FIG. 3 with a pixel pitch substantially equal to the diameter of the laser beam 4 and is moved by the sub-scanning motor 47 in the sub-scanning direction indicated by the arrow Y in FIG. 3, the whole surface of the focus position determination device 95 with the laser beam 4 having a wavelength of 532 nm.

When being irradiated with the laser beam 4, Cy3 contained in the spot 97 of the focus position determination device 95 is stimulated by the laser beam 4, thereby releasing fluorescence emission 25.

The fluorescence emission 25 released from Cy3 contained in the spot 97 passes through the lens 19, thereby being made a parallel beam, and is reflected by the perforated mirror 18, thereby entering the filter unit 27.

Since the filter unit 27 has been moved so that the filter 28b is located in the optical path, the fluorescence emission enters the filter 28b having a property to cut off light having a wavelength of 532 nm but transmit light having a wavelength longer than 532 nm.

Since the wavelength of fluorescence emission 25 is longer than that of the laser beam 4, i.e., the stimulating ray, the laser beam 4 is cut off by the filter 28b and only fluorescence emission 25 released from the spot 97 passes through the filter 28b.

The fluorescence emission transmitted through the filter 28b is reflected by the mirror 29, condensed by the lens 30 onto the pinhole 32a having the smallest diameter and photoelectrically detected by the photomultiplier 33, thereby producing analog data.

The analog data produced by the photomultiplier 33 are converted to digital data by the A/D converter 34 and the digital data are forwarded to the data processing apparatus 35.

Digital data converted by the A/D converter 34 and output to the data processing apparatus 35 are stored in the line memory 100.

When the whole surface of the focus position determination device 95 has been scanned with the laser beam 4 having a wavelength of 532 nm, fluorescence emission 25 released from Cy3 contained in the spot 97 has been photoelectrically detected by the photomultiplier 33 and digital data converted by the A/D converter 34 have been stored in the line memory 100, the control unit 80 turns off the second laser stimulating ray source 2 and outputs a data processing signal to the data processing section 101, thereby causing it to read the digital data from the line memory 100.

The data processing section 101 integrates the signal intensity of the digital data read from the line memory 100 and outputs an integrated value of the signal intensity of fluorescence emission 25 to the control unit 80.

The control unit 80 stores the integrated value of signal intensity of fluorescence emission 25 input from the data processing section 101 of the data processing apparatus 35 so as to be related to the position of the lens 19 of the optical head 15, namely, drive pulses applied to the stepping motor 76 in order to move the lens 19 of the optical head 15. At this time, since no drive pulse has not yet been applied to the stepping motor 76, the zero position is stored in the RAM 81 together with the integrated value of signal intensity of fluorescence emission 25.

When the integrated value of signal intensity of fluorescence emission 25 has been input from the data processing section 101 of the data processing apparatus 35 and stored in the RAM 81, the control unit 80 outputs a drive pulse signal to the stepping motor 76, thereby moving the lens 19 of the optical head 15 along the optical path of fluorescence emission by 10 microns with respect to the sample stage 20 and again turns on the second laser stimulating ray source 2.

In this manner, similarly to the case where the first laser stimulating ray source 1 was used, after the cycle including the steps of stimulating Cy3 contained in the spot 97 with the laser beam 4 having a wavelength of 532 nm, detecting fluorescence emission, producing digital data, calculating an integrated value of signal intensity of fluorescence emission 25 and storing the integrated value in the RAM 81 has been repeated a predetermined number of times, the control unit 80 calculates, based on the integrated value of signal intensity of fluorescence emission 25 stored in the RAM 81 and the positions of the lens 19 of the optical head 15, the position of the lens 19 where the maximum value of the integrated value of signal intensity of fluorescence emission 25 was produced in the form of the number of drive pulses applied to the stepping motor 76 in order to move the lens 19 of the optical head 15 from the zero position to the position where the maximum value of the integrated value of signal intensity of fluorescence emission 25 was produced and stores it in the EPROM 82 as the focus position data $P_{532}$ of the confocal optical system when the second laser stimulating ray source 2 is used, namely, when the laser beam 4 having a wavelength of 532 nm is used. At the same time, the control unit 80 stores the respective positions of the lens 19 of the optical head 15 and the corresponding integrated values of signal intensity of fluorescence emission 25 in the EPROM 82.

When the focus position data $P_{532}$ of the confocal optical system when the second laser stimulating ray source 2 is used has been determined and stored in the EPROM 82 in the form of the number of drive pulses to be applied to the stepping motor 76, the control unit 80 outputs a drive signal to the stepping motor 76, thereby causing it to return the sample stage 20 to the original position thereof and stores the position as the zero position in the RAM 81.

With the confocal optical system held so that the pinhole 32a having the smallest diameter is located in the optical path, the control unit 80 then outputs a drive signal to the stepping motor 76, thereby causing it to move the filter unit 27 so that the filter 28c having a property to cut off a light component having a wavelength of 473 nm and transmit light components having wavelengths longer than 473 nm is located in the optical path.

A laser beam 4 emitted from the third laser stimulating ray source 3 is reflected by the second dichroic mirror 8, thereby entering the optical head 15.

The laser beam 4 entering the optical unit 15 is reflected by the mirror 16, passes through the hole 17 formed in the perforated mirror 18 and through the lens 19 to impinge on the focus position determination device 95.

Since the sample stage 20 is moved by the main scanning motor 43 in the main scanning direction indicated by the arrow X in FIG. 3 with a pixel pitch substantially equal to the diameter of the laser beam 4 and is moved by the sub-scanning motor 47 in the sub-scanning direction indicated by the arrow Y in FIG. 3, the whole surface of the focus position determination device 95 with the laser beam 4 having a wavelength of 473 nm.

When being irradiated with the laser beam 4, Fluor-X contained in the spot 97 of the focus position determination device 95 is stimulated by the laser beam 4, thereby releasing fluorescence emission 25.

The fluorescence emission 25 released from Fluor-X contained in the spot 97 passes through the lens 19, thereby being made a parallel beam, and is reflected by the perforated mirror 18, thereby entering the filter unit 27.

Since the filter unit 27 has been moved so that the filter 28c is located in the optical path, the fluorescence emission enters the filter 28c having a property to cut off light having a wavelength of 473 nm but transmit light having a wavelength longer than 473 nm.

Since the wavelength of fluorescence emission 25 is longer than that of the laser beam 4, i.e., the stimulating ray, the laser beam 4 is cut off by the filter 28c and only fluorescence emission 25 released from the spot 97 passes through the filter 28c.

The fluorescence emission transmitted through the filter 28a is reflected by the mirror 29, condensed by the lens 30 onto the pinhole 32a having the smallest diameter and photoelectrically detected by the photomultiplier 33, thereby producing analog data.

The analog data produced by the photomultiplier 33 are converted to digital data by the A/D converter 34 and the digital data are forwarded to the data processing apparatus 35.

Digital data converted by the A/D converter 34 and output to the data processing apparatus 35 are stored in the line memory 100.

When the whole surface of the focus position determination device 95 has been scanned with the laser beam 4 having a wavelength of 532 nm, fluorescence emission 25 released from Fluor-X contained in the spot 97 has been photoelectrically detected by the photomultiplier 33 and digital data converted by the A/D converter 34 have been stored in the line memory 100, the control unit 80 turns off the first laser stimulating ray source 1 and outputs a data processing signal to the data processing section 101, thereby causing it to read the digital data from the line memory 100.

The data processing section 101 integrates the signal intensity of the digital data read from the line memory 100 and outputs an integrated value of the signal intensity of fluorescence emission 25 to the control unit 80.

The control unit 80 stores the integrated value of signal intensity of fluorescence emission 25 input from the data processing section 101 of the data processing apparatus 35 so as to be related to the position of the lens 19 of the optical head 15, namely, drive pulses applied to the stepping motor 76 in order to move the lens 19 of the optical head 15. At this time, since no drive pulse has yet been applied to the stepping motor 76, the zero position is stored in the RAM 81 together with the integrated value of signal intensity of fluorescence emission 25.

When the integrated value of signal intensity of fluorescence emission 25 has been input from the data processing section 101 of the data processing apparatus 35 and stored in the RAM 81, the control unit 80 outputs a drive pulse signal to the stepping motor 76, thereby moving the lens 19 of the optical head 15 along the optical path of fluorescence emission by 10 microns with respect to the sample stage 20 and again turns on the third laser stimulating ray source 3.

In this manner, similarly to the case where the first laser stimulating ray source 1 was used, after the cycle including the steps of stimulating Fluor-X contained in the spot 97 with the laser beam 4 having a wavelength of 473 nm, detecting fluorescence emission, producing digital data, calculating an integrated value of signal intensity of fluorescence emission 25 and storing the integrated value in the RAM 81 has been repeated a predetermined number of times, the control unit 80 calculates, based on the integrated value of signal intensity of fluorescence emission 25 stored in the RAM 81 and the positions of the lens 19 of the optical head 15, the position of the lens 19 where the maximum value of the integrated value of signal intensity of fluorescence emission 25 was produced in the form of the number of drive pulses applied to the stepping motor 76 in order to move the lens 19 of the optical head 15 from the zero position to the position where the maximum value of the integrated value of signal intensity of fluorescence emission 25 was produced and stores it in the EPROM 82 as the focus position data $P_{473}$ of the confocal optical system when the third laser stimulating ray source 3 is used, namely, when the laser beam 4 having a wavelength of 473 nm is used. At the same time, the control unit 80 stores the respective positions of the lens 19 of the optical head 15 and the corresponding integrated values of signal intensity of fluorescence emission 25 in the EPROM 82.

Figure 13:
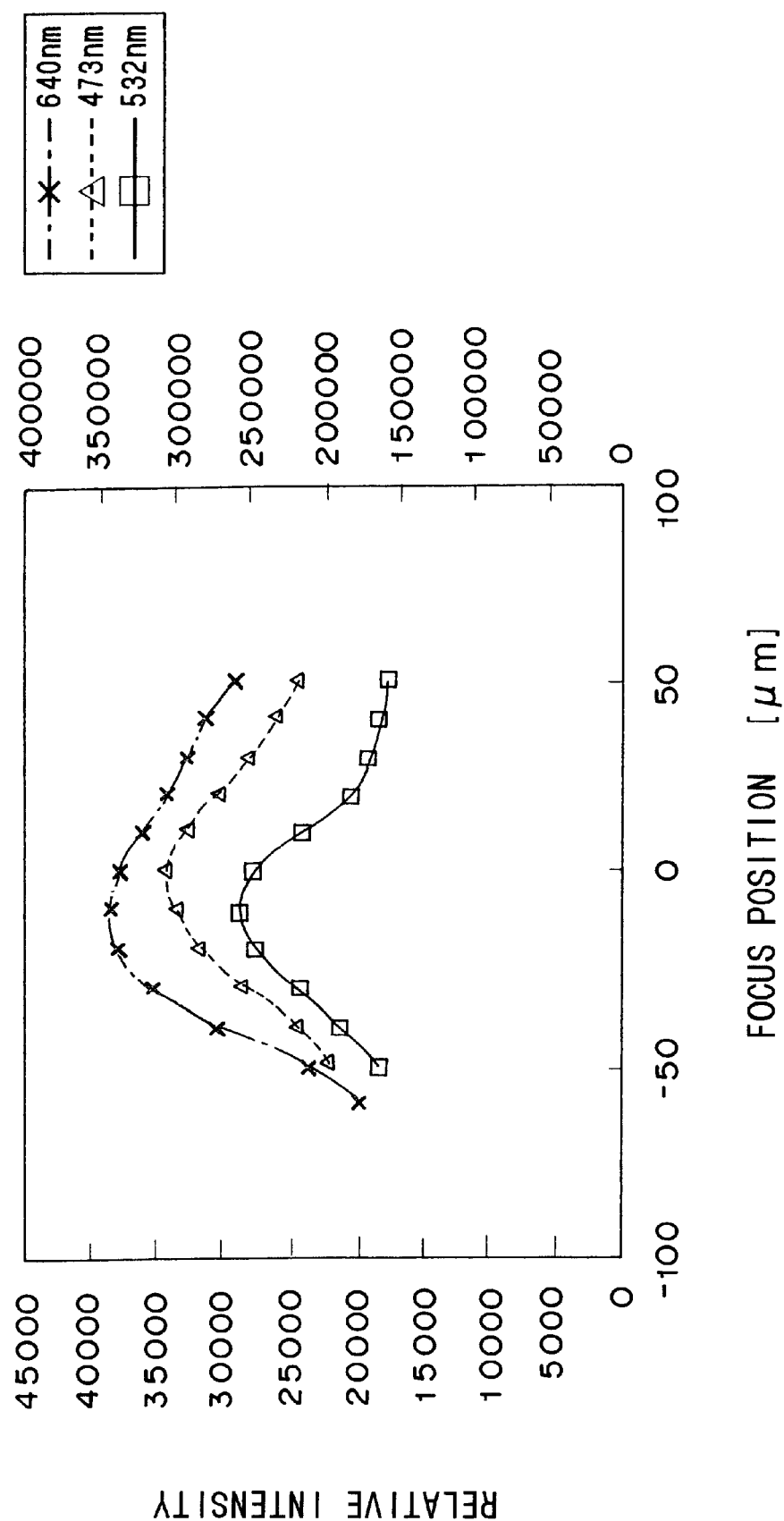
FIG. 13 is a graph obtained by plotting integrated values of signal intensity of digital data produced by scanning a focus position determination device with a laser beam having a wavelength of 640 nm, a laser beam having a wavelength of 532 nm and a laser beam having a wavelength of 473 nm.

FIG. 13 is a graph obtained by plotting the integrated values of signal intensity of digital data produced by scanning the focus position determination device 95 with the laser beam 4 having a wavelength of 640 nm, the laser beam 4 having a wavelength of 532 nm and the laser beam 4 having a wavelength of 473 nm at different positions of the lens 19 of the optical head 15 set by operating the stepping motor 76, photoelectrically detecting fluorescence emission released from Cy5, Cy3 and Fluor-X contained in the spot 97 by the photomultiplier 33 to produce analog data, and digitizing the analog data by the A/D converter 34.

In FIG. 13, the plotted data indicated by X represent the integrated values of signal intensity of digital data produced by stimulating Cy5 contained in the spot 97 with the laser beam 4 having a wavelength of 640 nm, the plotted data indicated by Δ represent the integrated values of signal intensity of digital data produced by stimulating Cy3 contained in the spot 97 with the laser beam 4 having a wavelength of 532 nm, and the plotted data indicated by □ represent the integrated values of signal intensity of digital data produced by stimulating Fluor-X contained in the spot 97 with the laser beam 4 having a wavelength of 473 nm. Since the focus position depends upon the wavelength of the laser beams 4, plotted data are obtained for each wavelength of the laser beams 4.

Since fluorescence emission 25 released from the fluorescent dye contained in the spot 97 can be most efficiently condensed when the spot 97 formed at the reference position on the focus position determination device 95 is located at the focal point of the lens 19, as shown in FIG. 13, the plotted data of the integrated values of signal intensity of fluorescence emission 25 detected by the photomultiplier 33 when the respective laser beams 4 are used have peaks when the spot 97 formed at the reference position on the focus position determination device 95 is located at the focal point of the lens 19.

Therefore, it is possible to determine the focus position of the confocal optical system by detecting the positions of the lens 19 corresponding to the positions of the peaks of the plotted data of the integrated values of signal intensity of fluorescence emission 25 based on the plotted data of the integrated values of signal intensity of fluorescence emission 25.

When in this manner the focus positions of the confocal optical system when the laser beam 4 having a wavelength of 640 nm, the laser beam 4 having a wavelength of 532 nm and the laser beam 4 having a wavelength of 473 nm are used have been determined and focus position data have been stored in the EPROM 82, the control unit 80 effects fitting on the curves X, Δ, □ shown in FIG. 13 and obtained by plotting the integrated values of signal intensity of digital data produced by irradiating the focus position determination device 95 with the laser beam 4 having a wavelength of 640 nm, the laser beam 4 having a wavelength of 532 nm and the laser beam 4 having a wavelength of 473 nm with an nth order function and stores the coefficient of the nth order function for each wavelength in the EPROM 82.

The control unit 80 further stores the focus position data for the laser beam 4 having a wavelength of 640 nm, the laser beam 4 having a wavelength of 532 nm and the laser beam 4 having a wavelength of 473 nm in the EPROM 82 and calculates an average value T0 of the temperature in the scanner when the coefficients of the nth order function are obtained based on temperature detection signals received from the temperature sensor 84 to store them in the EPROM 82.

The control unit 80 then reads the measurement point displacement data V1 of the first sample position to the measurement point displacement data V5 of the fifth sample position, the coefficient of the nth order function for each wavelength and the average value T0 of the temperature in the scanner stored in the EPROM 82, produces two-dimensional shading correction data of the first sample position to two-dimensional shading correction data of the fifth sample position for each wavelength of 640 nm, 532 nm and 473 nm at 15° C., 25° C. and 35° C. by two-dimensional interpolation, and stores the correction data in the shading correction data storing section 102 in the data processing apparatus 35.

The scanner in which the aforesaid various data have been determined and stored in the EPROM 82 produces data for biochemical analysis by scanning a micro-array including a slide glass plate on which a number of spots of a specimen selectively labeled with a fluorescent dye are formed as a substrate with a laser beam 4 to stimulate the fluorescent dye and photoelectrically detecting fluorescence emission released from the fluorescent dye in the following manner.

When the sample carrier 21 carrying five micro-arrays which are the samples is first placed on the sample stage 20 and set, the kind of the sample carrier 21 is detected by the carrier sensor 83 and a carrier detection signal is output to the control unit 80.

When the control unit 80 receives the carrier detection signal from the carrier sensor 83, it outputs a drive signal to the switching member motor 86 based on the carrier detection signal and causes it to move the confocal switching member 31 so that the pinhole 32a having the smallest diameter is located in the optical path.

The kind of a labeling substance, a fluorescent dye, is further input by the operator through the keyboard 88 and a labeling substance specifying signal is output from the keyboard 88 to the control unit 80.

When Cy5 (registered trademark), for example, is input as the kind of a fluorescent substance, the control unit 80 outputs a drive signal to the filter unit motor 85 in accordance with an instruction signal input through the keyboard 88, thereby causing it to move the filter unit 27 so that the filter 28a having a property to cut off a light component having a wavelength of 640 nm and transmit light components having wavelengths longer than 640 nm is located in the optical path.

At the same time, the control unit 80 reads from the EPROM 82 the focus position data $P_{640}$ of the confocal optical system when the first laser stimulating ray source 1 is used, the temperature coefficient K1 of the first sample position, the distance correction value ΔD1 of the first sample position, the focus position data of the confocal optical system for the laser beam 4 having a wavelength of 640 nm and the average value T0 of the temperature in the scanner when the focus position data of the confocal optical system and the coefficient of the nth order function were obtained, determines the number of drive pulses P to be applied to the stepping motor 76 in accordance with the following formula (1) using the temperature T in the scanner detected by and received from the temperature sensor 84, outputs a drive signal to the stepping motor 76 to move the lens 19 of the optical head 15 to a predetermined position and holds it at the position:

$$P = P_\lambda + A \times \{\Delta Di + Ki \times (T - T0)\} \quad (1).$$

In the formula (1), A designates a conversion coefficient between drive pulses and a distance, λ designates the wavelength of a laser beam 4 used for stimulating a labeling substance and i designates an integer from 1 to 5 and indicates the position of one of openings 51, 52, 53, 54, 55. When a micro-array 22 set in the first opening 51 in the sample carrier 21 is scanned with a laser beam 4 having a wavelength of 640 nm, $P_\lambda = P_{640}$, ΔDi=ΔD1 and Ki=K1.

The control unit 80 then outputs a drive signal to the first laser stimulating ray source 1 to turn it on.

The laser beam 4 emitted from the first laser stimulating ray source 1 passes through a collimator lens 5, thereby being made a parallel beam, and advances to the mirror 6 to be reflected thereby. The laser beam 4 reflected by the mirror 6 passes through the first dichroic mirror 7 and the second dichroic mirror 8 and enters the optical head 15.

The laser beam 4 entering the optical unit 15 is reflected by the mirror 16, passes through the hole 17 formed in the perforated mirror 18 and through the lens 19 to impinge on the sample 22, the micro-array set in the first opening 51, which is the first sample position in the sample carrier 21.

Since the sample stage 20 is moved by the main scanning motor 43 in the main scanning direction indicated by the arrow X in FIG. 3 with a pixel pitch substantially equal to the diameter of the laser beam 4 and is moved by the sub-scanning motor 47 in the sub-scanning direction indicated by the arrow Y in FIG. 3, the whole surface of the micro-array set in the first opening 51, which is the first sample position in the sample carrier 21, is scanned with the laser beam 4.

When being irradiated with the laser beam 4, Cy5 labeling the probe DNA is stimulated by the laser beam 4, thereby releasing fluorescence emission 25. In the case where a slide glass plate is used as a substrate of the micro-array, since the fluorescent dye is distributed on only the surface of the slide glass plate, fluorescence emission 25 is released from only the surface of the slide glass plate.

The fluorescence emission 25 released from the slide glass plate passes through the lens 19, thereby being made a parallel beam, and is reflected by the perforated mirror 18, thereby entering the filter unit 27.

Since the lens 19 of the optical head 15 is held based on the focus position data of the confocal optical system for the first laser stimulating ray source 1 stored in EPROM 82 so that the focal point of the lens 19 is located on the surface of the sample 22, fluorescence emission 25 released from the fluorescent dye distributed on the surface of the slide glass plate can be most efficiently condensed.

Since the filter unit 27 has been moved so that the filter 28a is located in the optical path, the fluorescence emission enters the filter 28a, thereby cutting light having a wavelength of 640 nm and transmitting only light having a wavelength longer than 640 nm.

The fluorescence emission transmitted through the filter 28a is reflected by the mirror 29 and focused by the lens 30.

Since the confocal switching member 31 has been moved prior to the irradiation with the laser beam 4 so that the pinhole 32a having the smallest diameter is located in the optical path, the fluorescence emission is focused onto the pinhole 32a and is photoelectrically detected by the photomultiplier 33, thereby producing analog data.

Fluorescence emission 25 released from the fluorescent dye on the surface of the slide glass plate is led to the photomultiplier 33 using a confocal optical system to be photoelectrically detected in this manner and, therefore, noise in the data can be minimized.

The analog data produced by the photomultiplier 33 are converted to digital data by the A/D converter 34 and the digital data are forwarded to the data processing apparatus 35 to be stored in the line memory 100.

When the whole surface of the micro-array 22 set in the first opening 51, which is the first sample position in the sample carrier 21, placed on the sample stage 20, has been scanned with the laser beam 4 having a wavelength of 640 nm and emitted from the first laser stimulating ray source 1 and digital data of Cy5 contained in the micro-array 22 have been stored in the line memory 100, the digital data of Cy5 contained in the micro-array 22 stored in the line memory 100 are read by the data processing section 101 and a temperature detection signal received from the temperature sensor 84 is output to the data processing section 101 of the data processing apparatus 35.

Although the focus position of the confocal optical system, namely, the position of the lens 19 of the optical head 15 is set based on the distance correction value $\Delta D1$ of the first sample position, which is an average value of displacements in positions of the nine measurement points on the distance measuring device 92a set in the first opening 51, which is the first sample position in the sample carrier 21, when the temperature in the scanner is set to 25° C. with respect to the position of the reference position at 15° C., since the displacements in the positions of the nine measurement points on the distance measuring device 92a set in the first opening 51, which is the first sample position in the sample carrier 21, with respect to the position of the reference position at 15° C. are not the same, the digital data of Cy5 contained in the micro-array 22 set in the first opening 51 in the sample carrier 21 inevitably contain shading.

Therefore, the data processing section 101 reads shading correction data of the first sample position produced when the first laser stimulating ray source 1 for emitting a laser beam 4 having a wavelength of 640 nm was used at 15° C., 25° C., and 35° C. and stored in the shading correction data storing section 102 and corrects them based on the temperature T in the scanner detected by the temperature sensor 84, thereby producing shading correction data of the first sample position corresponding to the temperature t in the scanner.

Based on the thus produced shading correction data of the first sample position at the temperature T in the scanner, the data processing section 101 corrects the shading of the digital data of Cy5 contained in the micro-array 22 set in the first opening 51, which is the first sample position in the sample carrier 21, read from the line memory 100 and stores the thus corrected digital data in the data storing section 103.

When in this manner the whole surface of the micro-array set in the first opening 51, which is the first sample position in the sample carrier 21, has been scanned with the laser beam 4 having a wavelength of 640 nm, fluorescence emission 25 released from Cy5 contained in the micro-array has been photoelectrically detected by the photomultiplier 33 to produce analog data, the analog data are converted by the A/D converter 34 to digital data, shading correction is effected on the digital data by the data processing section 101 and the thus corrected digital data are stored in the data storing section 103, the control unit 80 starts irradiating the micro-array set in the second opening 52, which is the second sample position in the sample carrier 21, with the laser beam 4 having a wavelength of 640 nm.

Prior to the irradiation of the micro-array set in the second opening 52, which is the second sample position, with the laser beam 4 having a wavelength of 640 nm, the control unit 80 first reads the temperature coefficient K2 of the second sample position and the distance correction value $\Delta D2$ of the second sample position stored in the EPROM 82, determines the number of drive pulses P to be applied to the stepping motor 76 in accordance with the following formula, outputs a drive signal to the stepping motor 76 to move the lens 19 of the optical head 15 to a predetermined position and holds it at the position:

$P=P_{640}+A\times\{\Delta D2+K2\times(T-T0)\}$.

The control unit 80 then outputs a drive signal to the first laser stimulating ray source 1 to turn it on. Similarly to the case where digital data were produced based on the micro-array set in the in the first opening 51, which is the first sample position in the sample carrier 21, the surface of the micro-array set in the second opening 52, which is the second sample position in the sample carrier 21, is scanned with the laser beam 4 having a wavelength of 640 nm, fluorescence emission 25 released from Cy5 contained in the micro-array is photoelectrically detected by the photomultiplier 33 to produce analog data, the analog data are converted by the A/D converter 34 to digital data and the thus produced digital data are stored in the line memory 100.

The data processing section 101 then reads shading correction data of the second sample position produced when the first laser stimulating ray source 1 for emitting a laser beam 4 having a wavelength of 640 nm was used at 15° C., 25° C., and 35° C. and stored in the shading correction data storing section 102 and corrects them based on the temperature T in the scanner detected by the temperature sensor 84, thereby producing shading correction data of the second sample position corresponding to the temperature T in the scanner.

Based on the thus produced shading correction data of the second sample position at the temperature T in the scanner, the data processing section 101 corrects the shading of the digital data of Cy5 contained in the micro-array 22 set in the second opening 52, which is the second sample position in the sample carrier 21, read from the line memory 100 and stores the thus corrected digital data in the data storing section 103.

For the micro-array set in the third opening 53, which is the third sample position in the sample carrier 21, the control unit 80 determines the number of drive pulses P to be applied to the stepping motor 76 in accordance with the following formula, outputs a drive signal to the stepping motor 76 to move the lens 19 of the optical head 15 to a predetermined position, holds it at the position, produces digital data of Cy5 contained in the micro-array to store them in the line memory 100 similarly to the case where the digital data were produced based on the micro-array set in the first opening 51, which is the first sample position in the sample carrier 21, reads shading correction data of the third sample position produced when the first laser stimulating ray source 1 for emitting a laser beam 4 having a wavelength of 640 nm was used at 15° C., 25° C., and 35° C. and stored in the shading correction data storing section 102, corrects them based on the temperature T in the scanner detected by the temperature sensor 84 to produce shading correction data of the third sample position corresponding to the temperature T in the scanner, corrects the shading of the digital data of Cy5 contained in the micro-array 22 stored in the line memory 100 based on the thus produced shading correction data of the third sample position at the temperature T in the scanner, and stores the thus corrected digital data in the data storing section 103:

$$P = P_{640} + A \times \{\Delta D3 + K3 \times (T-T0)\}.$$

Further, for the micro-array set in the fourth opening 54, which is the fourth sample position in the sample carrier 21, the control unit 80 determines the number of drive pulses P to be applied to the stepping motor 76 in accordance with the following formula, outputs a drive signal to the stepping motor 76 to move the lens 19 of the optical head 15 to a predetermined position, holds it at the position, produces digital data of Cy5 contained in the micro-array to store them in the line memory 100 similarly to the case where the digital data was produced based on the micro-array set in the first opening 51, which is the first sample position in the sample carrier 21, reads shading correction data of the fourth sample position produced when the first laser stimulating ray source 1 for emitting a laser beam 4 having a wavelength of 640 nm was used at 15° C., 25° C., and 35° C. and stored in the shading correction data storing section 102, corrects them based on the temperature T in the scanner detected by the temperature sensor 84 to produce shading correction data of the fourth sample position corresponding to the temperature T in the scanner, corrects the shading of the digital data of Cy5 contained in the micro-array 22 stored in the line memory 100 based on the thus produced shading correction data of the fourth sample position at the temperature T in the scanner, and stores the thus corrected digital data in the data storing section 103:

$$P = P_{640} + A \times \{\Delta D4 + K4 \times (T-T0)\}.$$

Moreover, for the micro-array set in the fifth opening 55, which is the fifth sample position in the sample carrier 21, the control unit 80 determines the number of drive pulses P to be applied to the stepping motor 76 in accordance with the following formula, outputs a drive signal to the stepping motor 76 to move the lens 19 of the optical head 15 to a predetermined position, holds it at the position, produces digital data of Cy5 contained in the micro-array to store them in the line memory 100 similarly to the case where the digital data was produced based on the micro-array set in the first opening 51, which is the first sample position in the sample carrier 21, reads shading correction data of the fifth sample position produced when the first laser stimulating ray source 1 for emitting a laser beam 4 having a wavelength of 640 nm was used at 15° C., 25° C., and 35° C. and stored in the shading correction data storing section 102, corrects them based on the temperature T in the scanner detected by the temperature sensor 84 to produce shading correction data of the fifth sample position corresponding to the temperature T in the scanner, corrects the shading of the digital data of Cy5 contained in the micro-array 22 stored in the line memory 100 based on the thus produced shading correction data of the fifth sample position at the temperature T in the scanner, and stores the thus corrected digital data in the data storing section 103:

$$P = P_{640} + A \times \{\Delta D5 + K5 \times (T-T0)\}.$$

In this manner, digital data of Cy5 contained in the micro-arrays set in the sample carrier 21 stored in the data storing section 103 of the data processing apparatus 35 are read and subjected to desired data processing as occasion demands in accordance with the instructions of the operator and a visible image is displayed on the screen of a display means (not shown) such as a CRT based on the digital data of Cy5 or data analysis is performed based on the digital data of Cy5.

On the other hand, when five micro-arrays each including a slide glass on which a number of spots of a specimen selectively labeled with Cy3 (registered trademark) are formed as a substrate are set in the first opening 51 to the fifth opening 55 in the sample carrier 21, an instruction signal specifying that a labeling substance is Cy3 and a start signal are input by the operator through the keyboard 88 and the signals are sent to the control unit 80.

When Cy3 is input as the kind of a fluorescent substance, the control unit 80 outputs a drive signal to the filter unit motor 85 in accordance with the instruction signal input through the keyboard 88, thereby causing it to move the filter unit 27 so that the filter 28b having a property to cut off a light component having a wavelength of 532 nm and transmit light components having wavelengths longer than 532 nm is located in the optical path.

At the same time, the control unit 80 reads from the EPROM 82 the focus position data $P_{532}$ of the confocal optical system when the second laser stimulating ray source 2 is used, the temperature coefficient K1 of the first sample position, the distance correction value $\Delta D1$ of the first sample position, the focus position data of the confocal optical system for the laser beam 4 having a wavelength of 532 nm and the average value T0 of the temperature in the scanner when the focus position data of the confocal optical system and the coefficient of the nth order function were obtained, determines the number of drive pulses P to be applied to the stepping motor 76 in accordance with the following formula (1) using a temperature T in the scanner detected by and received from the temperature sensor 84, outputs a drive signal to the stepping motor 76 to move the lens 19 of the optical head 15 to a predetermined position and holds it at the position:

$$P = P_\lambda + A \times \{\Delta Di + Ki \times (T-T0)\} \qquad (1).$$

In the formula (1), A designates a conversion coefficient between drive pulses and a distance, $\lambda$ designates the wavelength of a laser beam 4 used for stimulating a labeling substance and i designates an integer from 1 to 5 and indicates the position of one of openings 51, 52, 53, 54, 55. When a micro-array 22 set in the first opening 51 in the sample carrier 21 is scanned with a laser beam 4 having a wavelength of 532 nm, $P_\lambda = P_{532}$, $\Delta Di = \Delta D1$ and $Ki = K1$.

The control unit 80 then outputs a drive signal to the second laser stimulating ray source 2 to turn it on.

The laser beam 4 emitted from the second laser stimulating ray source 2 passes through a collimator lens 9, thereby being made a parallel beam, and advances to the first dichroic mirror 7 to be reflected thereby.

The laser beam 4 reflected by the first dichroic mirror 7 passes through the second dichroic mirror 8 and enters the optical head 15.

The laser beam 4 entering the optical unit 15 is reflected by the mirror 16, passes through the hole 17 formed in the perforated mirror 18 and through the lens 19 to impinge on the sample 22, the micro-array set in the first opening 51, which is the first sample position in the sample carrier 21.

Since the sample stage 20 is moved by the main scanning motor 43 in the main scanning direction indicated by the arrow X in FIG. 3 with a pixel pitch substantially equal to the diameter of the laser beam 4 and is moved by the sub-scanning motor 47 in the sub-scanning direction indicated by the arrow Y in FIG. 3, the whole surface of the micro-array set in the first opening 51, which is the first sample position in the sample carrier 21, is scanned with the laser beam 4.

When being irradiated with the laser beam 4, Cy3 labeling the probe DNA is stimulated by the laser beam 4, thereby releasing fluorescence emission 25. In the case where a slide glass plate is used as a substrate of the micro-array, since the fluorescent dye is distributed on only the surface of the slide glass plate, fluorescence emission 25 is released from only the surface of the slide glass plate.

The fluorescence emission 25 released from the slide glass plate passes through the lens 19, thereby being made a parallel beam, and is reflected by the perforated mirror 18, thereby entering the filter unit 27.

Since the lens 19 of the optical head 15 is held based on the focus position data of the confocal optical system for the second laser stimulating ray source 2 stored in EPROM 82 so that the focal point of the lens 19 is located on the surface of the sample 22, fluorescence emission 25 released from the fluorescent dye distributed on the surface of the slide glass plate can be most efficiently condensed.

Since the filter unit 27 has been moved so that the filter 28b is located in the optical path, the fluorescence emission enters the filter 28b, thereby cutting light having a wavelength of 532 nm and transmitting only light having a wavelength longer than 532 nm.

The fluorescence emission transmitted through the filter 28b is reflected by the mirror 29 and focused by the lens 30.

Since the confocal switching member 31 has been moved prior to the irradiation with the laser beam 4 so that the pinhole 32a having the smallest diameter is located in the optical path, the fluorescence emission 25 is focused onto the pinhole 32a and is photoelectrically detected by the photomultiplier 33, thereby producing analog data.

Fluorescence emission 25 released from the fluorescent dye on the surface of the slide glass plate is led to the photomultiplier 33 using a confocal optical system to be photoelectrically detected in this manner and, therefore, noise in the data can be minimized.

The analog data produced by the photomultiplier 33 are converted to digital data by the A/D converter 34 and the digital data are forwarded to the data processing apparatus 35 to be stored in the line memory 100.

When the whole surface of the micro-array 22 set in the first opening 51, which is the first sample position in the sample carrier 21, placed on the sample stage 20, has been scanned with the laser beam 4 having a wavelength of 532 nm and emitted from the second laser stimulating ray source 2 and digital data of Cy3 contained in the micro-array 22 have been stored in the line memory 100, the digital data of Cy3 contained in the micro-array 22 stored in the line memory 100 are read by the data processing section 101 and a temperature detection signal received from the temperature sensor 84 is output to the data processing section 101 of the data processing apparatus 35.

Although the focus position of the confocal optical system, namely, the position of the lens 19 of the optical head 15 is set based on the distance correction value ΔD1 of the first sample position which is an average value of displacements in positions of the nine measurement points on the distance measuring device 92a set in the first opening 51, which is the first sample position in the sample carrier 21, when the temperature in the scanner is set to 25° C. with respect to the position of the reference position at 15° C., since the displacements in the positions of the nine measurement points on the distance measuring device 92a set in the first opening 51, which is the first sample position in the sample carrier 21, with respect to the position of the reference position at 15° C. are not the same, the digital data of Cy3 contained in the micro-array 22 set in the first opening 51 in the sample carrier 21 inevitably contain shading.

Therefore, the data processing section 101 reads shading correction data of the first sample position produced when the second laser stimulating ray source 2 for emitting a laser beam 4 having a wavelength of 532 nm was used at 15° C., 25° C., and 35° C. and stored in the shading correction data storing section 102 and corrects them based on the temperature T in the scanner detected by the temperature sensor 84, thereby producing shading correction data of the first sample position corresponding to the temperature T in the scanner.

Further, based on the thus produced shading correction data of the first sample position at the temperature T in the scanner, the data processing section 101 corrects the shading of the digital data of Cy3 contained in the micro-array 22 set in the first opening 51, which is the first sample position in the sample carrier 21, read from the line memory 100 and stores the thus corrected digital data in the data storing section 103.

When in this manner the whole surface of the micro-array set in the first opening 51, which is the first sample position in the sample carrier 21, has been scanned with the laser beam 4 having a wavelength of 532 nm, fluorescence emission 25 released from Cy3 contained in the micro-array has been photoelectrically detected by the photomultiplier 33 to produce analog data, the analog data have been converted by the A/D converter 34 to digital data, shading correction has been effected on the digital data by the data processing section 101 and the thus corrected digital data have been stored in the data storing section 103, the control unit 80 starts irradiating the micro-array set in the second opening 52, which is the second sample position in the sample carrier 21, with the laser beam 4 having a wavelength of 532 nm.

Prior to the irradiation of the micro-array set in the second opening 52, which is the second sample position, with the laser beam 4 having a wavelength of 532 nm, the control unit 80 first reads the temperature coefficient K2 of the second sample position and the distance correction value ΔD2 of the second sample position stored in the EPROM 82, determines the number of drive pulses P to be applied to the stepping motor 76 in accordance with the following formula, outputs a drive signal to the stepping motor 76 to move the lens 19 of the optical head 15 to a predetermined position and holds it at the position:

$$P=P_{532}+A\times\{\Delta D2+K2\times(T-T0)\}.$$

The control unit 80 then outputs a drive signal to the second laser stimulating ray source 2 to turn it on. Similarly to the case where digital data were produced based on the micro-array set in the in the first opening 51, which is the first sample position in the sample carrier 21, the surface of the micro-array set in the second opening 52, which is the second sample position in the sample carrier 21, is scanned with the laser beam 4 having a wavelength of 532 nm, fluorescence emission 25 released from Cy3 contained in the micro-array is photoelectrically detected by the photomultiplier 33 to produce analog data, the analog data are converted by the A/D converter 34 to digital data and the thus produced digital data are stored in the line memory 100.

The data processing section 101 then reads shading correction data of the second sample position produced when the second laser stimulating ray source 2 for emitting a laser beam 4 having a wavelength of 532 nm was used at 15° C., 25° C., and 35° C. and stored in the shading correction data storing section 102 and corrects them based on the temperature T in the scanner detected by the temperature sensor 84, thereby producing shading correction data of the second sample position corresponding to the temperature T in the scanner.

Further, based on the thus produced shading correction data of the second sample position at the temperature T in the scanner, the data processing section 101 corrects the shading of the digital data of Cy3 contained in the micro-array 22 set in the second opening 52, which is the second sample position in the sample carrier 21, read from the line memory 100 and stores the thus corrected digital data in the data storing section 103.

For the micro-array set in the third opening 53, which is the third sample position in the sample carrier 21, the control unit 80 determines the number of drive pulses P to be applied to the stepping motor 76 in accordance with the following formula, outputs a drive signal to the stepping motor 76 to move the lens 19 of the optical head 15 to a predetermined position, holds it at the position, produces digital data of Cy3 contained in the micro-array to store them in the line memory 100 similarly to the case where the digital data were produced based on the micro-array set in the first opening 51, which is the first sample position in the sample carrier 21, reads shading correction data of the third sample position produced when the second laser stimulating ray source 2 for emitting a laser beam 4 having a wavelength of 532 nm was used at 15° C., 25° C., and 35° C. and stored in the shading correction data storing section 102, corrects them based on the temperature T in the scanner detected by the temperature sensor 84 to produce shading correction data of the third sample position corresponding to the temperature T in the scanner, corrects the shading of the digital data of Cy3 contained in the micro-array 22 stored in the line memory 100 based on the thus produced shading correction data of the third sample position at the temperature T in the scanner, and stores the thus corrected digital data in the data storing section 103:

$$P=P_{532}+A\times\{\Delta D3+K3\times(T-T0)\}.$$

Further, for the micro-array set in the fourth opening 54, which is the fourth sample position in the sample carrier 21, the control unit 80 determines the number of drive pulses P to be applied to the stepping motor 76 in accordance with the following formula, outputs a drive signal to the stepping motor 76 to move the lens 19 of the optical head 15 to a predetermined position, holds it at the position, produces digital data of Cy3 contained in the micro-array to store them in the line memory 100 similarly to the case where the digital data were produced based on the micro-array set in the first opening 51, which is the first sample position in the sample carrier 21, reads shading correction data of the fourth sample position produced when the second laser stimulating ray source 2 for emitting a laser beam 4 having a wavelength of 532 nm was used at 15° C., 25° C., and 35° C. and stored in the shading correction data storing section 102, corrects them based on the temperature T in the scanner detected by the temperature sensor 84 to produce shading correction data of the fourth sample position corresponding to the temperature T in the scanner, corrects the shading of the digital data of Cy3 contained in the micro-array 22 stored in the line memory 100 based on the thus produced shading correction data of the fourth sample position at the temperature T in the scanner, and stores the thus corrected digital data in the data storing section 103:

$$P=P_{532}+A\times\{\Delta D4+K4\times(T-T0)\}.$$

Moreover, for the micro-array set in the fifth opening 55, which is the fifth sample position in the sample carrier 21, the control unit 80 determines the number of drive pulses P to be applied to the stepping motor 76 in accordance with the following formula, outputs a drive signal to the stepping motor 76 to move the lens 19 of the optical head 15 to a predetermined position, holds it at the position, produces digital data of Cy3 contained in the micro-array to store them in the line memory 100 similarly to the case where the digital data were produced based on the micro-array set in the first opening 51, which is the first sample position in the sample carrier 21, reads shading correction data of the fifth sample position produced when the second laser stimulating ray source 2 for emitting a laser beam 4 having a wavelength of 532 nm was used at 15° C., 25° C., and 35° C. and stored in the shading correction data storing section 102, corrects them based on the temperature T in the scanner detected by the temperature sensor 84 to produce shading correction data of the fifth sample position corresponding to the temperature T in the scanner, corrects the shading of the digital data of Cy3 contained in the micro-array 22 stored in the line memory 100 based on the thus produced shading correction data of the fifth sample position at the temperature T in the scanner, and stores the thus corrected digital data in the data storing section 103:

$$P=P_{532}+A\times\{\Delta D5+K5\times(T-T0)\}.$$

In this manner, digital data of Cy3 contained in the micro-arrays set in the sample carrier 21 stored in the data storing section 103 of the data processing apparatus 35 are read and subjected to desired data processing as occasion demands in accordance with the instructions of the operator and a visible image is displayed on the screen of a display means (not shown) such as a CRT based on the digital data of Cy3 or data analysis is performed based on the digital data of Cy3.

On the other hand, when five micro-arrays each including a slide glass on which a number of spots of a specimen selectively labeled with Fluor-X (registered trademark) are formed as a substrate are set in the first opening 51 to the fifth opening 55 in the sample carrier 21, an instruction signal specifying that the labeling substance is Fluor-X and a start signal are input by the operator through the keyboard 88 and the signals are sent to the control unit 80.

When Fluor-X is input as the kind of a fluorescent substance, the control unit 80 outputs a drive signal to the filter unit motor 85 in accordance with the instruction signal input through the keyboard 88, thereby causing it to move the filter unit 27 so that the filter 28c having a property to cut off a light component having a wavelength of 473 nm and transmit light components having wavelengths longer than 473 nm is located in the optical path.

At the same time, the control unit 80 reads from the EPROM 82 the focus position data $P_{473}$ of the confocal optical system when the third laser stimulating ray source 3 is used, the temperature coefficient K1 of the first sample position, the distance correction value ΔD1 of the first sample position, the focus position data of the confocal optical system for the laser beam 4 having a wavelength of 473 nm and the average value T0 of the temperature in the scanner when the focus position data of the confocal optical system and the coefficient of the nth order function were obtained, determines the number of drive pulses P to be applied to the stepping motor 76 in accordance with the following formula (1) using a temperature T in the scanner detected by and received from the temperature sensor 84, outputs a drive signal to the stepping motor 76 to move the lens 19 of the optical head 15 to a predetermined position and holds it at the position:

$$P=P_\lambda+A\times\{\Delta Di+Ki\times(T-T0)\} \quad (1).$$

In the formula (1), A designates a conversion coefficient between drive pulses and a distance, λ designates the wavelength of a laser beam 4 used for stimulating a labeling substance and i designates an integer from 1 to 5 and indicates the position of one of openings 51, 52, 53, 54, 55. When a micro-array 22 set in the first opening 51 in the sample carrier 21 is scanned with a laser beam 4 having a wavelength of 473 nm, $P_\lambda=P_{473}$, ΔDi=ΔD1 and Ki=K1.

The control unit 80 then outputs a drive signal to the third laser stimulating ray source 3 to turn it on.

The laser beam 4 emitted from the third laser stimulating ray source 3 passes through a collimator lens 10, thereby being made a parallel beam, and is reflected by the second dichroic mirror 8, thereby entering the optical head 15.

The laser beam 4 entering the optical unit 15 is reflected by the mirror 16, passes through the hole 17 formed in the perforated mirror 18 and through the lens 19 to impinge on the sample 22, the micro-array set in the first opening 51, which is the first sample position in the sample carrier 21.

Since the sample stage 20 is moved by the main scanning motor 43 in the main scanning direction indicated by the arrow X in FIG. 3 with a pixel pitch substantially equal to the diameter of the laser beam 4 and is moved by the sub-scanning motor 47 in the sub-scanning direction indicated by the arrow Y in FIG. 3, the whole surface of the micro-array set in the first opening 51, which is the first sample position in the sample carrier 21, is scanned with the laser beam 4.

When being irradiated with the laser beam 4, Fluor-X labeling the probe DNA is stimulated by the laser beam 4, thereby releasing fluorescence emission 25. In the case where a slide glass plate is used as a substrate of the micro-array, since the fluorescent dye is distributed on only the surface of the slide glass plate, fluorescence emission 25 is released from only the surface of the slide glass plate.

The fluorescence emission 25 released from the slide glass plate passes through the lens 19, thereby being made a parallel beam, and is reflected by the perforated mirror 18, thereby entering the filter unit 27.

Since the lens 19 of the optical head 15 is held based on the focus position data of the confocal optical system for the third laser stimulating ray source 3 stored in EPROM 82 so that the focal point of the lens 19 is located on the surface of the sample 22, fluorescence emission 25 released from the fluorescent dye distributed on the surface of the slide glass plate can be most efficiently condensed.

Since the filter unit 27 has been moved so that the filter 28c is located in the optical path, the fluorescence emission enters the filter 28c, thereby cutting light having a wavelength of 473 nm and transmitting only light having a wavelength longer than 473 nm.

The fluorescence emission transmitted through the filter 28b is reflected by the mirror 29 and focused by the lens 30.

Since the confocal switching member 31 has been moved prior to the irradiation with the laser beam 4 so that the pinhole 32a having the smallest diameter is located in the optical path, the fluorescence emission 25 is focused onto the pinhole 32a and is photoelectrically detected by the photomultiplier 33, thereby producing analog data.

Fluorescence emission 25 released from the fluorescent dye on the surface of the slide glass plate is led to the photomultiplier 33 using a confocal optical system to be photoelectrically detected in this manner and, therefore, noise in the data can be minimized.

The analog data produced by the photomultiplier 33 are converted to digital data by the A/D converter 34 and the digital data are forwarded to the data processing apparatus 35 to be stored in the line memory 100.

When the whole surface of the micro-array 22 set in the first opening 51, which is the first sample position in the sample carrier 21, placed on the sample stage 20, has been scanned with the laser beam 4 having a wavelength of 473 nm and emitted from the third laser stimulating ray source 3 and digital data of Fluor-X contained in the micro-array 22 have been stored in the line memory 100, the digital data of Fluor-X contained in the micro-array 22 stored in the line memory 100 are read by the data processing section 101 and a temperature detection signal received from the temperature sensor 84 is output to the data processing section 101 of the data processing apparatus 35.

Although the focus position of the confocal optical system, namely, the position of the lens 19 of the optical head 15 is set based on the distance correction value ΔD1 of the first sample position, which is an average value of displacements in positions of the nine measurement points on the distance measuring device 92a set in the first opening 51, which is the first sample position in the sample carrier 21, when the temperature in the scanner is set to 25° C. with respect to the position of the reference position at 15° C., since the displacements in the positions of the nine measurement points on the distance measuring device 92a set in the first opening 51, which is the first sample position in the sample carrier 21, with respect to the position of the reference position at 15° C. are not the same, the digital data of Cy3 contained in the micro-array 22 set in the first opening 51 in the sample carrier 21 inevitably contain shading.

Therefore, the data processing section 101 reads shading correction data of the first sample position produced when the third laser stimulating ray source 3 for emitting a laser beam 4 having a wavelength of 473 nm was used at 15° C., 25° C., and 35° C. and stored in the shading correction data storing section 102 and corrects them based on the temperature T in the scanner detected by the temperature sensor 84, thereby producing shading correction data of the first sample position corresponding to the temperature T in the scanner.

Further, based on the thus produced shading correction data of the first sample position at the temperature T in the scanner, the data processing section 101 corrects the shading of the digital data of Fluor-X contained in the micro-array 22 set in the first opening 51, which is the first sample position in the sample carrier 21, read from the line memory 100 and stores the thus corrected digital data in the data storing section 103.

When in this manner the whole surface of the micro-array set in the first opening 51, which is the first sample position in the sample carrier 21, has been scanned with the laser beam 4 having a wavelength of 473 nm, fluorescence emission 25 released from Fluor-X contained in the micro-array has been photoelectrically detected by the photomultiplier 33 to produce analog data, the analog data have been converted by the A/D converter 34 to digital data, shading correction has been effected on the digital data by the data processing section 101 and the thus corrected digital data have been stored in the data storing section 103, the control unit 80 starts irradiating the micro-array set in the second opening 52, which is the second sample position in the sample carrier 21, with the laser beam 4 having a wavelength of 473 nm.

Prior to the irradiation of the micro-array set in the second opening 52, which is the second sample position, with the laser beam 4 having a wavelength of 473 nm, the control unit 80 first reads the temperature coefficient K2 of the second sample position and the distance correction value ΔD2 of the second sample position stored in the EPROM 82, determines the number of drive pulses P to be applied to the stepping motor 76 in accordance with the following formula, outputs a drive signal to the stepping motor 76 to move the lens 19 of the optical head 15 to a predetermined position and holds it at the position:

$$P=P_{473}+A\times\{\Delta D2+K2\times(T-T0)\}.$$

The control unit 80 then outputs a drive signal to the third laser stimulating ray source 3 to turn it on. Similarly to the case where digital data were produced based on the micro-array set in the in the first opening 51, which is the first sample position in the sample carrier 21, the surface of the micro-array set in the second opening 52, which is the second sample position in the sample carrier 21, is scanned with the laser beam 4 having a wavelength of 473 nm, fluorescence emission 25 released from Fluor-X contained in the micro-array is photoelectrically detected by the photomultiplier 33 to produce analog data, the analog data are converted by the A/D converter 34 to digital data and the thus produced digital data are stored in the line memory 100.

The data processing section 101 then reads shading correction data of the second sample position produced when the third laser stimulating ray source 3 for emitting a laser beam 4 having a wavelength of 473 nm was used at 15° C., 25° C., and 35° C. and stored in the shading correction data storing section 102 and corrects them based on the temperature T in the scanner detected by the temperature sensor 84, thereby producing shading correction data of the second sample position corresponding to the temperature T in the scanner.

Further, based on the thus produced shading correction data of the second sample position at the temperature T in the scanner, the data processing section 101 corrects the shading of the digital data of Fluor-X contained in the micro-array 22 set in the second opening 52, which is the second sample position in the sample carrier 21, read from the line memory 100 and stores the thus corrected digital data in the data storing section 103.

For the micro-array set in the third opening 53, which is the third sample position in the sample carrier 21, the control unit 80 determines the number of drive pulses P to be applied to the stepping motor 76 in accordance with the following formula, outputs a drive signal to the stepping motor 76 to move the lens 19 of the optical head 15 to a predetermined position, holds it at the position, produces digital data of Fluor-X contained in the micro-array to store them in the line memory 100 similarly to the case where the digital data were produced based on the micro-array set in the first opening 51, which is the first sample position in the sample carrier 21, reads shading correction data of the third sample position produced when the third laser stimulating ray source 3 for emitting a laser beam 4 having a wavelength of 473 nm was used at 15° C., 25° C., and 35° C. and stored in the shading correction data storing section 102, corrects them based on the temperature T in the scanner detected by the temperature sensor 84 to produce shading correction data of the third sample position corresponding to the temperature T in the scanner, corrects the shading of the digital data of Fluor-X contained in the micro-array 22 stored in the line memory 100 based on the thus produced shading correction data of the third sample position at the temperature T in the scanner, and stores the thus corrected digital data in the data storing section 103:

$$P=P_{473}+A\times\{\Delta D3+K3\times(T-T0)\}.$$

Further, for the micro-array set in the fourth opening 54, which is the fourth sample position in the sample carrier 21, the control unit 80 determines the number of drive pulses P to be applied to the stepping motor 76 in accordance with the following formula, outputs a drive signal to the stepping motor 76 to move the lens 19 of the optical head 15 to a predetermined position, holds it at the position, produces digital data of Fluor-X contained in the micro-array to store them in the line memory 100 similarly to the case where the digital data were produced based on the micro-array set in the first opening 51, which is the first sample position in the sample carrier 21, reads shading correction data of the fourth sample position produced when the third laser stimulating ray source 3 for emitting a laser beam 4 having a wavelength of 473 nm was used at 15° C., 25° C., and 35° C. and stored in the shading correction data storing section 102, corrects them based on the temperature T in the scanner detected by the temperature sensor 84 to produce shading correction data of the fourth sample position corresponding to the temperature T in the scanner, corrects the shading of the digital data of Fluor-X contained in the micro-array 22 stored in the line memory 100 based on the thus produced shading correction data of the fourth sample position at the temperature T in the scanner, and stores the thus corrected digital data in the data storing section 103:

$$P=P_{473}+A\times\{\Delta D4+K4\times(T-T0)\}.$$

Moreover, for the micro-array set in the fifth opening 55, which is the fifth sample position in the sample carrier 21, the control unit 80 determines the number of drive pulses P to be applied to the stepping motor 76 in accordance with the following formula, outputs a drive signal to the stepping motor 76 to move the lens 19 of the optical head 15 to a predetermined position, holds it at the position, produces digital data of Fluor-X contained in the micro-array to store them in the line memory 100 similarly to the case where the digital data were produced based on the micro-array set in the first opening 51, which is the first sample position in the sample carrier 21, reads shading correction data of the fifth sample position produced when the third laser stimulating ray source 3 for emitting a laser beam 4 having a wavelength of 473 nm was used at 15° C., 25° C., and 35° C. and stored in the shading correction data storing section 102, corrects them based on the temperature T in the scanner detected by the temperature sensor 84 to produce shading correction data of the fifth sample position corresponding to the temperature T in the scanner, corrects the shading of the digital data of Fluor-X contained in the micro-array 22 stored in the line memory 100 based on the thus produced shading correction data of the fifth sample position at the temperature T in the scanner, and stores the thus corrected digital data in the data storing section 103

$$P=P_{473}+A\times\{\Delta D5+K5\times(T-T0)\}.$$

In this manner, digital data of Fluor-X contained in the micro-arrays set in the sample carrier 21 stored in the data storing section 103 of the data processing apparatus 35 are read and subjected to desired data processing as occasion demands in accordance with the instructions of the operator and a visible image is displayed on the screen of a display means (not shown) such as a CRT based on the digital data of Fluor-X or data analysis is performed based on the digital data of Fluor-X.

On the other hand, in the case where data for biochemical analysis are to be produced by scanning a fluorescence sample including a transfer support containing denatured DNA fragments selectively labeled with a fluorescent dye as a substrate with a laser beam 4 to stimulate the fluorescent dye and photoelectrically detecting fluorescence emission released from the fluorescent dye, a sample carrier 21 carrying a fluorescence sample 22 including a transfer support containing denatured DNA fragments selectively labeled with a fluorescent dye is set on the sample stage 20.

When the sample carrier 21 carrying the fluorescence sample 22 is set on the sample stage 20, the kind of the sample carrier 21 is detected by the carrier sensor 83 and a carrier detection signal is output to the control unit 80.

When the control unit 80 receives the carrier detection signal from the carrier sensor 83, it outputs a drive signal to the switching member motor 86 based on the carrier detection signal and causes it to move the confocal switching member 31 so that the pinhole 32c having the largest diameter is located in the optical path.

When the kind of a labeling substance, an instruction signal specifying the fluorescent substance and a start signal are input by the operator through the keyboard 88, the signals are sent from the keyboard 88 to the control unit 80.

When the specimen is labeled with Rhodamine (registered trademark), for example, since Rhodamine can be most effectively stimulated by a laser beam having a wavelength of 532 nm, the control unit 80 selects the second laser stimulating ray source 2 and the filter 28b and also outputs a drive signal to the filter unit motor 85, thereby causing it to move the filter unit 27 so that the filter 28b having a property to cut off a light component having a wavelength of 532 nm and transmit light components having wavelengths longer than 532 nm is located in the optical path. At the same time, the control unit 80 reads the focus position data $P_{532}$ of the confocal optical system when the second laser stimulating ray source 2 is used, the temperature coefficient K1 of the first sample position to the temperature coefficient K5 of the fifth sample position, the distance correction value $\Delta D1$ of the first sample position to the distance correction value $\Delta D5$ of the fifth sample position, the focus position data of the confocal optical system for the laser beam 4 having a wavelength of 532 nm and the average value T0 of the temperature in the scanner when the focus position data of the confocal optical system and the coefficient of the nth order function were obtained.

The control unit 80 calculates an average value $K_{AV}$ of the temperature coefficient K1 of the first sample position to the temperature coefficient K5 of the fifth sample position and an average value $\Delta D_{AV}$ of the distance correction value $\Delta D1$ of the first sample position to the distance correction value $\Delta D5$ of the fifth sample position. The control unit 80 then determines the number of drive pulses P to be applied to the stepping motor 76 in accordance with the following formula (2) using a temperature T in the scanner detected by and received from the temperature sensor 84, outputs a drive signal to the stepping motor 76 to move the lens 19 of the optical head 15 to a predetermined position and holds it at the position:

$$P=P_{532}+A\times\{\Delta D_{AV}+K_{AV}\times(T-T0)\} \qquad (2).$$

The control unit 80 then outputs a drive signal to the second laser stimulating ray source 2 to turn it on.

The laser beam 4 emitted from the second laser stimulating ray source 2 passes through a collimator lens 9, thereby being made a parallel beam, and advances to the first dichroic mirror 7 to be reflected thereby.

The laser beam 4 reflected by the first dichroic mirror 7 passes through the second dichroic mirror 8 and enters the optical head 15.

The laser beam 4 entering the optical unit 15 is reflected by the mirror 16, passes through the hole 17 formed in the perforated mirror 18 and through the lens 19 to impinge on the fluorescence sample 22 set in the sample carrier 21.

Since the sample stage 20 is moved by the main scanning motor 43 in the main scanning direction indicated by the arrow X in FIG. 3 with a pixel pitch substantially equal to the diameter of the laser beam 4 and is moved by the sub-scanning motor 47 in the sub-scanning direction indicated by the arrow Y in FIG. 3, the whole surface of the fluorescence sample 22 set in the sample carrier 21 is scanned with the laser beam 4.

When being irradiated with the laser beam 4, a fluorescent dye labeling the specimen, Rhodamine, for example, is stimulated by the laser beam 4, thereby releasing fluorescence emission 25. In the case where a transfer support is used as a substrate of the fluorescence sample 22, since a fluorescent dye is distributed in the depth direction of the transfer support, fluorescence emission 25 is released from a predetermined region in the depth direction of the transfer support and the positions of the light emitting points fluctuate in the depth direction.

The fluorescence emission 25 released from the fluorescence sample 22 using the transfer support as a substrate passes through the lens 19, thereby being made a parallel beam, and is reflected by the perforated mirror 18, thereby entering the filter unit 27.

Since the lens 19 of the optical head 15 is held based on the focus position data of the confocal optical system for the second laser stimulating ray source 2 stored in EPROM 82 so that the focal point of the lens 19 is located on the surface of the sample 22, fluorescence emission 25 released from the fluorescent dye contained in the transfer support can be most efficiently condensed.

Since the filter unit 27 has been moved so that the filter 28b is located in the optical path, the fluorescence emission enters the filter 28b, thereby cutting light having a wavelength of 532 nm and transmitting only light having a wavelength longer than 532 nm.

The fluorescence emission transmitted through the filter 28b is reflected by the mirror 29 and condensed by the lens 30. However, since the fluorescence emission 25 is released from a predetermined region in the depth direction of the transfer support, the fluorescence emission is not focused.

Since the confocal switching member 31 has been moved prior to the irradiation with the laser beam 4 so that the pinhole 32c having the largest diameter is located in the optical path, the fluorescence emission 25 passes through the pinhole 32c and is photoelectrically detected by the photomultiplier 33, thereby producing analog image data. Therefore, even though a confocal optical system is employed for detecting fluorescence emission 25 released from the fluorescent dye on the surface of the micro-array using the slide glass plate as a substrate with a high S/N ratio, the fluorescence emission 25 released from a predetermined region in the depth direction of the transfer support can nevertheless be detected with high signal intensity.

The analog data produced by the photomultiplier 33 are converted to digital data by the A/D converter 34 and the digital data are forwarded to the data processing apparatus 35 to be stored in the line memory 100.

Although the focus position of the confocal optical system, namely, the position of the lens 19 of the optical head 15 is determined by correcting the focus position data $P_{532}$ of the confocal optical system determined with respect to the reference position of the distance measuring device 92a set in the first opening 51, which is the first sample position in the sample carrier 21, when the second laser stimulating ray source 2 for emitting the laser beam 4 having a wavelength of 532 nm is used, using the average value $K_{AV}$ of the temperature coefficient K1 of the first sample position to the temperature coefficient K5 of the fifth sample position and the average value $\Delta D_{AV}$ of the distance correction value $\Delta D1$ of the first sample position to the distance correction value $\Delta D5$ of the fifth sample position, since the distance between the fluorescence sample 22 and the lens 19 of the optical head 15 when the sample stage 20 is scanned with the laser beam 4 is not constant, the thus produced digital data of the fluorescence sample 22 inevitably contain shading.

Therefore, the data processing section 101 reads shading correction data of the first sample position to the fifth sample position produced when the second laser stimulating ray source 2 for emitting a laser beam 4 having a wavelength of 532 nm was used at 15° C., 25° C., and 35° C. and stored in the shading correction data storing section 102 and corrects them based on the temperature T in the scanner detected by the temperature sensor 84, thereby producing shading correction data of the fluorescence sample corresponding to the temperature T in the scanner.

Further, based on the thus produced shading correction data of the fluorescence sample at the temperature T in the scanner, the data processing section 101 corrects the shading of the digital data of the fluorescence sample read from the line memory 100 and stores the thus corrected digital data in the data storing section 103.

To the contrary, in the case where data for biochemical analysis are to be produced by scanning a stimulable phosphor layer of a stimulable phosphor sheet in which locational information of a radioactive labeling substance are recorded by closely contacting a substrate such as a membrane filter having a number of spots of a specimen selectively labeled with a radioactive labeling substance and the stimulable phosphor sheet formed with the stimulable phosphor layer containing a stimulable phosphor to expose the stimulable phosphor layer with the radioactive labeling substance with a laser beam 4 to excite the stimulable phosphor and photoelectrically detecting stimulated emission released from the stimulable phosphor, a sample carrier 21 carrying a stimulable phosphor sheet formed with a stimulable phosphor layer is set on the sample stage 20.

When the sample carrier 21 carrying the stimulable phosphor sheet formed with the stimulable phosphor layer is set on the sample stage 20, the kind of the sample carrier 21 is detected by the carrier sensor 83 and a carrier detection signal is output to the control unit 80.

When the control unit 70 receives the carrier detection signal from the carrier sensor 83, it outputs a drive signal to the switching member motor 86 based on the carrier detection signal and causes it to move the confocal switching member 31 so that the pinhole 32b having an intermediate diameter is located in the optical path.

The control unit 80 further outputs a drive signal to the filter unit motor 85 in accordance with the carrier detection signal, thereby causing it to move the filter unit 27 so that the filter 28d having a property to transmit only a light component having a wavelength of the stimulated emission and to cut off a light component having a wavelength of 640 nm is located in the optical path and reads the focus position data $P_{640}$ of the confocal optical system when the first laser stimulating ray source 1 is used, the temperature coefficient K1 of the first sample position to the temperature coefficient K5 of the fifth sample position, the distance correction value $\Delta D1$ of the first sample position to the distance correction value $\Delta D5$ of the fifth sample position, the focus position data of the confocal optical system for the laser beam 4 having a wavelength of 640 nm and the average value T0 of the temperature in the scanner when the focus position data of the confocal optical system and the coefficient of the nth order function were obtained.

The control unit 80 calculates an average value $K_{AV}$ of the temperature coefficient K1 of the first sample position to the temperature coefficient K5 of the fifth sample position and an average value $\Delta D_{AV}$ of the distance correction value $\Delta D1$ of the first sample position to the distance correction value $\Delta D5$ of the fifth sample position. The control unit 80 then determines the number of drive pulses P to be applied to the stepping motor 76 in accordance with the following formula (3) using a temperature T in the scanner detected by and received from the temperature sensor 84, outputs a drive signal to the stepping motor 76 to move the lens 19 of the optical head 15 to a predetermined position and holds it at the position:

$$P=P_{640}+A\times\{\Delta D_{AV}+K_{AV}\times(T-T0)\} \tag{3}$$

The control unit 50 then outputs a drive signal to the first laser stimulating ray source 1, thereby turning it on.

A laser beam 4 emitted from the first laser stimulating ray source 1 passes through a collimator lens 5, thereby being made a parallel beam, and is reflected by the mirror 6. The laser beam 4 reflected by the mirror 6 passes through the first dichroic mirror 7 and the second dichroic mirror 8 and enters the optical head 15.

The laser beam 4 entering the optical unit 15 is reflected by the mirror 16, passes through the hole 17 formed in the perforated mirror 18 and through the lens 19 to impinge on the sample 22, the stimulable phosphor sheet, which is a sample 22 set on the sample stage 20.

Since the sample stage 20 is moved by the main scanning motor 43 in the main scanning direction indicated by the arrow X in FIG. 3 with a pixel pitch substantially equal to the diameter of the laser beam 4 and is moved by the sub-scanning motor 47 in the sub-scanning direction indicated by the arrow Y in FIG. 3, the whole surface of the stimulable phosphor layer of the stimulable phosphor sheet, which is a sample 22 set in the sample carrier 21, is scanned with the laser beam 4.

When being irradiated with the laser beam 4, a stimulable phosphor contained in the stimulable phosphor layer is excited by the laser beam 4, thereby releasing stimulated emission 25. In the stimulable phosphor sheet, since a stimulable phosphor is contained in the stimulable phosphor layer and is distributed in the depth direction of the stimulable phosphor layer to some extent, stimulated emission is released from a predetermined region in the depth direction of the stimulable phosphor layer and the positions of the light emitting points fluctuate in the depth direction. However, since the stimulable phosphor layer is thin, the distribution of the light emitting points in the depth direction is not so great as that when reading a fluorescent image carried in the transfer support.

The stimulated emission 25 released from the stimulable phosphor layer passes through the lens 19, thereby being made a parallel beam, and is reflected by the perforated mirror 18, thereby entering the filter unit 27.

Since the lens 19 of the optical head 15 is held based on the focus position data of the confocal optical system for the first laser stimulating ray source 1 stored in EPROM 82 so that the focal point of the lens 19 is located on the surface of the sample 22, stimulated emission 25 released from the stimulable phosphor contained in the stimulable phosphor layer can be most efficiently condensed.

Since the filter unit 27 has been moved so that the filter 28d is located in the optical path, the stimulated emission enters the filter 28d, thereby cutting light having a wavelength of 640 nm and transmitting only light having a wavelength of the stimulated emission released from the stimulable phosphor.

The stimulated emission 25 transmitted through the filter 28d is reflected by the mirror 29 and condensed by the lens 30. However, since the stimulated emission is released from a predetermined region in the depth direction of the stimulable phosphor layer, it is not focused.

Since the confocal switching member 31 has been moved prior to the irradiation with the laser beam 4 so that the pinhole 32b having an intermediate diameter is located in the optical path, the stimulated emission 25 passes through the pinhole 32b and is photoelectrically detected by the photomultiplier 33, thereby producing analog image data. Therefore, even though a confocal optical system is employed for detecting fluorescence emission 25 released from the fluorescent dye on the surface of the micro-array using the slide glass plate as a substrate with a high S/N ratio, stimulated emission 25 released from a predetermined region in the depth direction of the stimulable phosphor layer formed on the stimulable phosphor sheet can nevertheless be detected with high signal intensity.

The analog data produced by the photomultiplier 33 are converted to digital data by the A/D converter 34 and the digital data are forwarded to the data processing apparatus 35 to be stored in the line memory 100.

Although the focus position of the confocal optical system, namely, the position of the lens 19 of the optical head 15 is determined by correcting the focus position data $P_{640}$ of the confocal optical system determined with respect to the reference position of the distance measuring device 92a set in the first opening 51, which is the first sample position in the sample carrier 21, when the first laser stimulating ray source 1 for emitting the laser beam 4 having a wavelength of 640 nm is used, using the average value $K_{AV}$ of the temperature coefficient K1 of the first sample position to the temperature coefficient K5 of the fifth sample position and the average value $\Delta D_{AV}$ of the distance correction value ΔD1 of the first sample position to the distance correction value ΔD5 of the fifth sample position, since the distance between the stimulable phosphor layer of the stimulable phosphor sheet and the lens 19 of the optical head 15 when the sample stage 20 is scanned with the laser beam 4 is not constant, the thus produced digital data of the radioactive labeling substance contained in the stimulable phosphor layer of the stimulable phosphor sheet inevitably contain shading.

Therefore, the data processing section 101 reads shading correction data of the first sample position to the fifth sample position produced when the first laser stimulating ray source 1 for emitting a laser beam 4 having a wavelength of 640 nm was used at 15° C., 25° C., and 35° C. and stored in the shading correction data storing section 102 and corrects them based on the temperature T in the scanner detected by the temperature sensor 84, thereby producing shading correction data of the radioactive labeling substance corresponding to the temperature T in the scanner.

Further, based on the thus produced shading correction data of the fluorescence sample at the temperature T in the scanner, the data processing section 101 corrects the shading of the digital data of the radioactive labeling substance read from the line memory 100 and stores the thus corrected digital data in the data storing section 103.

In the above described embodiment, the distance measuring devices 92a, 92b, 92c, 92d, 92e each constituted as a slide glass plate 90 formed with a chromium layer 91 formed by sputtering on the whole surface thereof are set in the first opening 51 to the fifth opening 55 corresponding to the first sample position to the fifth sample position in the sample carrier 21 into which five micro-arrays including a slide glass plate as a substance are set, the displacements in positions of the reference point determined on the distance measuring device 92a and the eight measurement points on the distance measuring device 92a at 25° C. and 35° C. with respect to the position of the reference point on the distance measuring device 92a at 15° C. and the displacements in positions of the nine measurement points on each of the distance measuring devices 92b, 92c, 92d, 92e at 15° C., 25° C. and 35° C. with respect to the position of the reference point on the distance measuring device 92a at 15° C. are measured by the electrostatic capacitance displacement meter 79, the temperature coefficients of the nine measurement points on each of the distance measuring devices 92a, 92b, 92c, 92d, 92e are calculated, the average values thereof are determined as the temperature coefficients K1, K2, K3, K4, K5 of the first sample position, the second sample position, the third sample position, the fourth sample position and the fifth sample position in the sample carrier 21 to be stored in the EPROM 82, average values of the displacements in positions of the nine measurement points on each of the distance measuring devices 92a, 92b, 92c, 92d, 92e at 25° C. with respect to the position of the reference point on the distance measuring device 92a at 15° C. are calculated, and the distance correction values ΔD1, ΔD2, ΔD3, ΔD4, ΔD5 of the first sample position, the second sample position, the third sample position, the fourth sample position and the fifth sample position in the sample carrier 21 to be stored in the EPROM 82.

Further, in the above described embodiment, the focus position determination device 95 constituted as a slide glass plate 96 on which the spot 97 containing Fluor-X (registered trademark), Cy3 (registered trademark) and Cy5 (registered trademark) is formed at the reference position corresponding to the reference point of the distance measuring device 92a when the focus position determination device 95 is set in the first opening 51 in the sample carrier 21 is set in the first opening 51, which is the first sample position in the sample carrier 21, drive pulses are applied to the stepping motor 76 of the lens height position adjusting apparatus 70, the focus position determination device 95 is sequentially scanned with the laser beam 4 having a wavelength of 640 nm, the laser beam 4 having a wavelength of 532 nm and the laser beam 4 having a wavelength of 473 nm while the lens 19 of the optical head 15 is being moved to stimulate sequentially Fluor-X, Cy3 and Cy5 contained in the spot 97, fluorescence emission 25 released from Fluor-X, Cy3 and Cy5 is photo-electrically detected to produce analog data, the analog data are converted by the A/D converter 34 to digital data, the integrated values of signal intensity of fluorescence emission 25 in the digital data are plotted for each wavelength of the laser beam 4 to produce plotted data, the position of the lens 19 of the optical head 15 at which the integrated value of signal intensity is maximum in each set of the plotted data is determined as the focus position of the confocal optical system of the laser beam 4 of each wavelength, the numbers of drive pulses to be applied to the stepping motor 76 for moving the lens 19 of the optical head 15 from the zero position of the lens 19 of the optical head 15 as a reference position to the focus position of the confocal optical system for each wavelength of the laser beam 4 are determined as the focus position data $P_{640}$, $P_{532}$, $P_{473}$ of the confocal optical system for the laser beam 4 having a wavelength of 640 nm, the laser beam 4 having a wavelength of 532 nm and the laser beam 4 having a wavelength of 473 nm, and the focus position data $P_{640}$, $P_{532}$, $P_{473}$ of the confocal optical system for the laser beam 4 having a wavelength of 640 nm, the laser beam 4 having a wavelength of 532 nm and the laser beam 4 having a wavelength of 473 nm are stored in the EPROM together with the temperature T0 at which the focus position data $P_{640}$, $P_{532}$, $P_{473}$ of the confocal optical system for the laser beam 4 having a wavelength of 640 nm, the laser beam 4 having a wavelength of 532 nm and the laser beam 4 having a wavelength of 473 nm were produced.

In the above described embodiment, based on the thus calculated temperature coefficients K1, K2, K3, K4, K5 of the first sample position, the second sample position, the third sample position, the fourth sample position and the fifth sample position in the sample carrier 21, the distance correction values ΔD1, ΔD2, ΔD3, ΔD4, ΔD5 of the first sample position, the second sample position, the third sample position, the fourth sample position and the fifth sample position in the sample carrier 21 and the focus position data $P_{640}$, $P_{532}$, $P_{473}$ of the confocal optical system for the laser beam 4 having a wavelength of 640 nm, the laser beam 4 having a wavelength of 532 nm and the laser beam 4 having a wavelength of 473 nm stored in the EPROM 82, the number of drive pulses P to be applied to the stepping motor 76 is determined so as to satisfy the following formula (1) in accordance with the wavelength of the laser beam 4 to be used, the temperature T in the scanner and the sample position of the sample carrier 21 in which a micro-array is set, and a drive signal is output to the stepping motor 76 to move the lens 19 of the optical head 15 to a predetermined position and hold it at the position. In the formula (1), A designates a conversion coefficient between drive pulses and a distance, λ designates the wavelength of a laser beam 4 used for stimulating a labeling substance and i designates an integer from 1 to 5 and indicates one of the first opening 51 to the fifth opening 55 in the sample carrier 21:

$$P = P_\lambda + A \times \{\Delta Di + Ki \times (T-T0)\} \quad (1).$$

Therefore, even though the optimum focus position of the confocal optical system depends upon the wavelength of the laser beam 4 and the temperature T in the scanner and also depends upon the sample position in the sample carrier 21, the above described embodiment nevertheless enables fluorescence emission 25 released from the fluorescent dye(s) contained in the micro-array to be condensed in a desired manner and led to the photomultiplier 33, thereby producing digital data of the fluorescent dye(s) contained in the micro-array, since the lens 19 of the optical head 15 can be moved to the optimum focus position and held there with respect to each micro-array set in one of the first opening 51 to the fifth opening 55, which are the first sample position to the fifth sample position in the sample carrier 21.

Furthermore, in the above described embodiment, the displacements in positions of the nine measurement points on each of the distance measuring devices 92a, 92b, 92c, 92d, 92e with respect to the position of the reference point on the distance measuring device 92a at 15° C. are stored in the EPROM 82 as the first measurement point displacement data V1, the second measurement point displacement data V2, the third measurement point displacement data V3, the fourth measurement point displacement data V4 and the fifth measurement point displacement data V5, the plotted data of the integrated values of signal intensity of fluorescence emission 25 for each wavelength of the laser beam 4 used for producing the focus position data $P_{640}$, $P_{532}$ or $P_{473}$ of the confocal optical system when the laser beam 4 having a wavelength of 640 nm, the laser beam 4 having a wavelength of 532 nm or the laser beam 4 having a wavelength of 473 nm was used are subjected to fitting with an nth order function, the coefficient of the nth order function is stored in the EPROM 82 for each wavelength of the laser beam 4, the measurement point displacement data V1 of the first sample position to the measurement point displacement data V5 of the fifth sample position, the coefficient of the nth order function for each wavelength of the laser beam 4 and the average value T0 of the temperature in the scanner stored in the EPROM 82 are read, and two-dimensional shading correction data of the first sample position to two-dimensional shading correction data of the fifth sample position for each wavelength of 640 nm, 532 nm and 473 nm at 15° C., 25° C. and 35° C. are produced by two-dimensional interpolation to be stored in the shading correction data storing section 102 in the data processing apparatus 35.

In the above described embodiment, the data processing section 101 of the data processing apparatus 35 is constituted so as to read, in accordance with the wavelength of the laser beam 4 to be used and the sample position in the sample carrier 21, two-dimensional shading correction data at 15° C., 25° C. and 35° C. of the corresponding sample position and for the corresponding wavelength of the laser beam 4 from among the thus stored two-dimensional shading correction data of the first sample position to two-dimensional shading correction data of the fifth sample position for each wavelength of the laser beam 4 in the EPROM 82, to correct them based on the temperature T in the scanner detected by the temperature sensor 84 to produce shading data corresponding to the temperature T in the scanner, to correct, based on the thus produced shading correction data, the shading of the digital data of the fluorescent dye(s) contained in the micro-array obtained by scanning the micro-array set in the corresponding sample position in the sample carrier 21 with the laser beam 4 having the corresponding wavelength, and to store the digital data of the fluorescent dye(s) contained in the micro-array, shadings have been corrected, in the data storing section 103.

Therefore, even though the shading of the digital data of the fluorescent dye(s) contained in the micro-array depends upon the wavelength of the laser beam 4, the position of the micro-array set in the sample carrier 21 and the temperature in the scanner, the above described embodiment enables the shading of the digital data of the fluorescent dye(s) contained in the micro-array to be corrected in a desired manner irrespective of the wavelength of the laser beam 4, the position of the micro-array set in the sample carrier 21 and the temperature in the scanner,.

Moreover, according to the above described embodiment, the focus position of the confocal optical system is determined in advance and stored in the EPROM 82, and the position of the lens 19 of the optical head 15 is adjusted based on the focus position data of the confocal optical system stored in the EPROM 82. Therefore, unlike the case where the focus of a confocal optical system is adjusted using an auto-focusing system, no special devices, such as a reflected light detecting optical system, a sensor, a detection circuit and the like, are needed, and the focus position of the confocal optical system can be adjusted without increasing cost.

Figure 14:
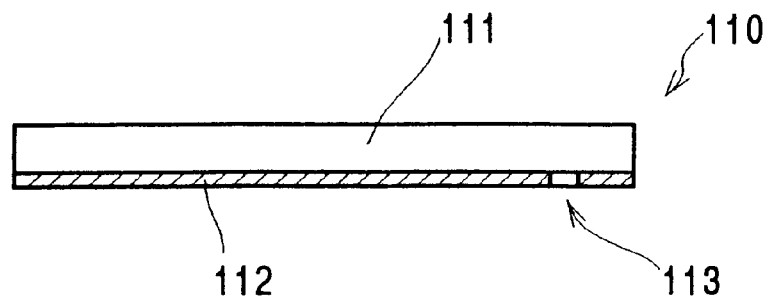
FIG. 14 is a schematic cross-sectional view showing a focus position determination device used for determining the focus of a confocal optical system of a scanner, which is another preferred embodiment of the present invention.
Figure 15:
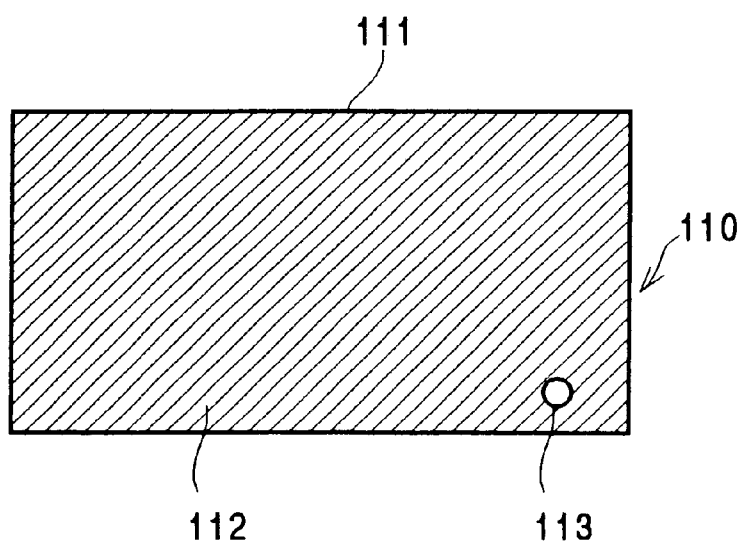
FIG. 15 is a schematic plan view showing a focus position determination device used for determining the focus of a confocal optical system of a scanner, which is another preferred embodiment of the present invention.

FIG. 14 is a schematic cross-sectional view showing a focus position determination device used for determining the focus of the confocal optical system of the scanner, which is another preferred embodiment of the present invention, and FIG. 15 is a schematic plan view thereof.

As shown in FIGS. 14 and 15, a focus position determination device 110 includes a support 111 constituted as a color glass filter formed by doping glass containing material selected from a group consisting of silica sand, soda ash and limestone as a principal component with a solid solution of CdS—CdSe. A chromium layer 112 is formed on the support 111 by sputtering, and a pinhole 113 is formed at a position of the chromium layer 112 corresponding to the reference point of the distance measuring device 92a.

In this embodiment, the focus position determination device 110 is shaped to be substantially rectangular, and the pinhole 113 is formed so that the width thereof in a scanning direction of the laser beam 4 is substantially equal to the diameter of the laser beam 4.

The support 111 constituted as a color glass filter formed by doping glass containing material selected from a group consisting of silica sand, soda ash and limestone as a principal component with a solid solution of CdS—CdSe has a property to be excited and emit fluorescence emission upon being irradiated with the laser beam 4 having a wavelength of 640 nm, the laser beam 4 having a wavelength of 532 nm and the laser beam 4 having a wavelength of 473 nm. Therefore, it is possible to produce the focus position data $P_{640}$, $P_{532}$ or $P_{473}$ of the confocal optical system for the laser beam 4 having a wavelength of 640 nm, the laser beam 4 having a wavelength of 532 nm and the laser beam 4 having a wavelength of 473 nm similarly to the previous embodiment by setting the focus position determination device 110 in the first opening 51, which is the first sample position in the sample carrier 21, so that the position of the pinhole 113 coincides with the position of the spot 97 of the focus position determination device 95 shown in FIG. 11, sequentially scanning the focus position determination device 110 with the laser beam 4 having a wavelength of 640 nm, the laser beam 4 having a wavelength of 532 nm and the laser beam 4 having a wavelength of 473 nm to stimulate the color glass filter 111 via the pinhole 113, photoelectrically detecting fluorescence emission released from the color glass filter 111 via the pinhole 113 by the photomultiplier 33 to produce analog data, and digitizing the analog data by the A/D converter 34, to store the the focus position data $P_{640}$, $P_{532}$ or $P_{473}$ of the confocal optical system in the EPROM 82, and move the lens 19 of the optical head 15 to the optimum focus position of the confocal optical system in accordance with the wavelength of the laser beam 4, the sample position of a micro-array set in the sample carrier 21 and the temperature in the scanner, thereby holding the lens 19 of the optical head 15.

In the case where a spot 97 containing a fluorescent dye(s) is formed on a slide glass plate 96 and irradiated with a laser beam 4 to determine the focus position of the confocal optical system, the fluorescent dye(s) is sometimes degraded during the irradiation with the laser beam 4, thereby decreasing the amount of fluorescence emission released from the fluorescent dye(s) with the elapse of time and it is sometimes difficult to accurately determine the focus position of the confocal optical system. However, according to this embodiment, since the color glass filter 111 is not degraded by irradiation with the laser beam 4, it is possible to accurately determine the focus position of the confocal optical system and the focus position determination device 110 can be repeatedly used for determining the focus position of the confocal optical system.

Figure 16:
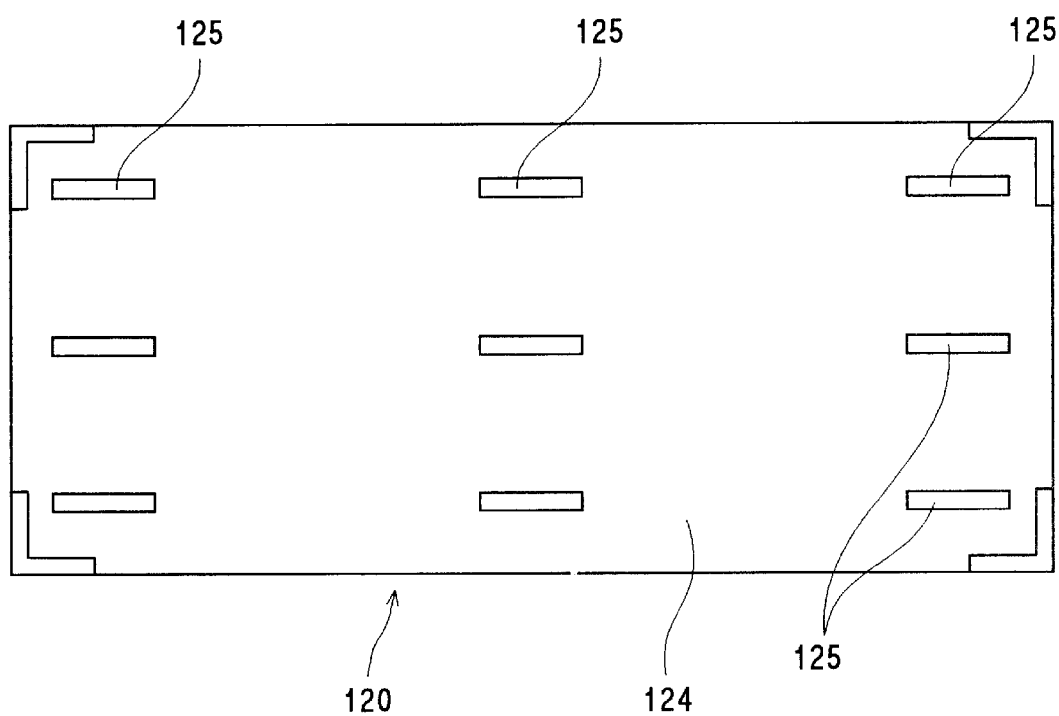
FIG. 16 is a schematic plan view showing a shading estimation device used for producing shading correction data of a scanner, which is a further preferred embodiment of the present invention.
Figure 17:
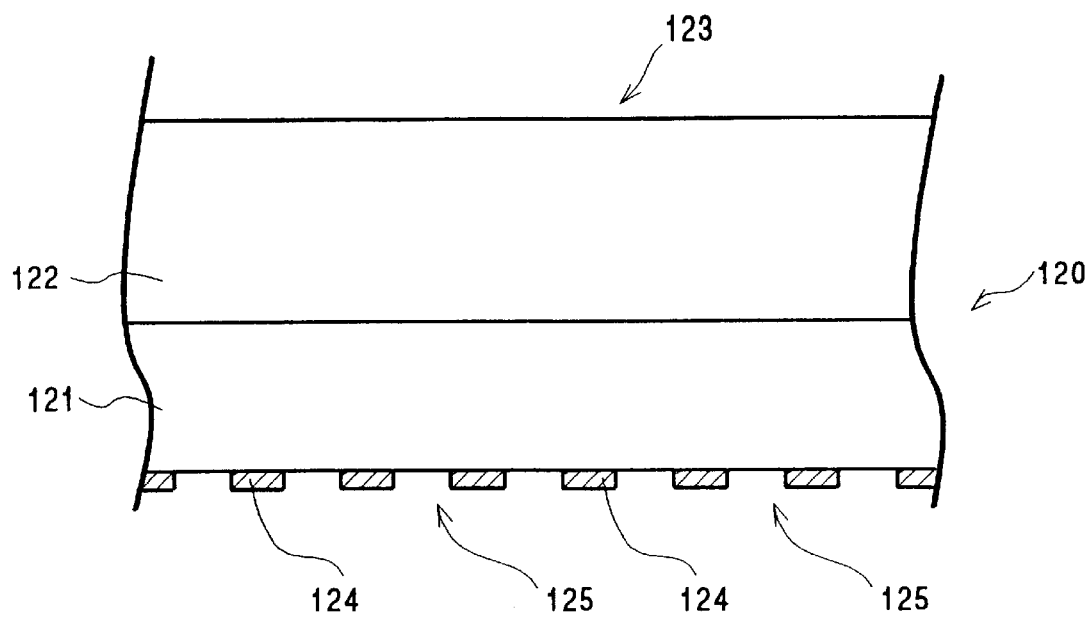
FIG. 17 is a schematic longitudinal cross-sectional view showing a shading estimation device used for producing shading correction data of a scanner, which is a further preferred embodiment of the present invention.

FIG. 16 is a schematic plan view showing a shading estimation device used for producing shading correction data in the scanner, which is a further preferred embodiment of the present invention, and FIG. 17 is a schematic longitudinal cross-sectional view thereof.

As shown in FIGS. 16 and 17, a shading estimation device 120 according to this embodiment includes a substantially rectangular laminate 123 formed by laminating an InGaAsP layer 121 and a GaAs layer 122. A chromium layer 124 is formed on the surface of the InGaAsP layer 121 by chemical vapor deposition and slits 125 are regularly formed at the position of the reference point indicated by the black circle and positions of the measurement points indicated by the white circles on the distance measuring devices 92a, 92b, 92c, 92d, 92e in FIG. 8.

Each slit 125 is formed so that the width thereof in the scanning direction of the laser beam 4 is substantially equal to the diameter of the laser beam 4.

The laminate 123 composed of the InGaAsP layer 121 and the GaAs layer 122 has a property to be excited upon being irradiated with the laser beam 4 having a wavelength of 640 nm, the laser beam 4 having a wavelength of 532 nm and the laser beam 4 having a wavelength of 473 nm and emit fluorescence emission. Therefore, it is possible to produce shading correction data using five shading estimation devices 120 in the following manner.

Five shading estimation devices 120 are first set in the first opening 51 to the fifth opening 55 in the sample carrier 21 so that the positions of nine slits 125 in each of the shading estimation device 120 coincide with the position of the reference point indicated by the black circle and positions of the measurement points indicated by the white circles on the distance measuring device 92a or, positions of the measurement points indicated by the white circles on the distance measuring devices 92b, 92c, 92d, 92e in FIG. 8.

When a shading data producing signal is then input by the operator through the keyboard 88, the shading data producing signal is sent to the control unit 80.

When the control unit 80 receives the shading data producing signal, it first sets the temperature in the scanner to 15° C. and outputs a drive signal to the filter unit motor 85, thereby causing it to move the filter unit 27 so that the filter 28a having a property to cut off a light component having a wavelength of 640 nm and transmit light components having wavelengths longer than 640 nm is located in the optical path.

At the same time, the control unit 80 reads from the EPROM 82, the focus position data $P_{640}$ of the confocal optical system when the first laser stimulating ray source 1 is used, the temperature coefficient K1 of the first sample position, the distance correction value ΔD1 of the first sample position, the focus position data of the confocal optical system for the laser beam 4 having a wavelength of 640 nm and the average value T0 of the temperature in the scanner when the focus position data of the confocal optical system and the coefficient of the nth order function were obtained, determines the number of drive pulses P to be applied to the stepping motor 76 in accordance with the following formula (1) using a temperature T in the scanner detected by and received from the temperature sensor 84, outputs a drive signal to the stepping motor 76 to move the lens 19 of the optical head 15 to a predetermined position and holds it at the position:

$$P = P_\lambda + A \times \{\Delta Di + Ki \times (T - T0)\} \quad (1).$$

In the formula (1), A designates a conversion coefficient between drive pulses and a distance, λ designates the wavelength of a laser beam 4 used for stimulating a labeling substance and i designates an integer from 1 to 5 and indicates the position of one of openings 51, 52, 53, 54, 55. When a micro-array 22 set in the first opening 51 in the sample carrier 21 is scanned with a laser beam 4 having a wavelength of 640 nm, $P_\lambda = P_{640}$, ΔDi=ΔD1 and Ki=K1.

The control unit 80 then outputs a drive signal to the first laser stimulating ray source 1 to turn it on.

The laser beam 4 emitted from the first laser stimulating ray source 1 passes through a collimator lens 5, thereby being made a parallel beam, and advances to the mirror 6 to be reflected thereby. The laser beam 4 reflected by the mirror 6 passes through the first dichroic mirror 7 and the second dichroic mirror 8 and enters the optical head 15.

The laser beam 4 entering the optical unit 15 is reflected by the mirror 16, passes through the hole 17 formed in the perforated mirror 18 and through the lens 19 to impinge on the shading estimation device 120 set in the first opening 51, which is the first sample position in the sample carrier 21.

Since the sample stage 20 is moved by the main scanning motor 43 in the main scanning direction indicated by the arrow X in FIG. 3 with a pixel pitch substantially equal to the diameter of the laser beam 4 and is moved by the sub-scanning motor 47 in the sub-scanning direction indicated by the arrow Y in FIG. 3, the whole surface of the shading estimation device 120 set in the first opening 51, which is the first sample position in the sample carrier 21, is scanned with the laser beam 4.

When being irradiated through the nine slits regularly formed in the shading estimation device 120 with the laser beam 4, the laminate 123 composed of the InGaAsP layer 121 and the GaAs layer 122 is stimulated to release fluorescence emission 25.

The fluorescence emission 25 released from the laminate 123 composed of the InGaAsP layer 121 and the GaAs layer 122 passes through the lens 19, thereby being made a parallel beam, and is reflected by the perforated mirror 18, thereby entering the filter unit 27.

Since the filter unit 27 has been moved so that the filter 28a is located in the optical path, the fluorescence emission enters the filter 28a, thereby cutting light having a wavelength of 640 nm and transmitting only light having a wavelength longer than 640 nm.

Since the wavelength of fluorescence emission 25 is longer than that of the laser beam 4, i.e., the stimulating ray, the laser beam 4 is cut off by the filter 28a and only the fluorescence emission 25 released from the laminate 123 composed of the InGaAsP layer 121 and the GaAs layer 122 passes through the filter 28a.

The fluorescence emission transmitted through the filter 28a is reflected by the mirror 29, condensed by the lens 30 onto the pinhole 32a having the smallest diameter and photoelectrically detected by the photomultiplier 33, thereby producing analog data.

The analog data produced by the photomultiplier 33 are converted to digital data by the A/D converter 34 and the digital data are forwarded to the data processing apparatus 35.

Digital data converted by the A/D converter 34 and sent to the data processing apparatus 35 are stored in the line memory 100.

When the whole surface of the shading estimation device 120 has been scanned with the laser beam 4 having a wavelength of 640 nm and the digital data of the shading estimation device 120 have been stored in the line memory 100, the control unit 80 turns off the first laser stimulating ray source 1.

The digital data stored in the line memory 100 are read by the data processing section 101.

The data processing section 101 integrates the signal intensity of fluorescence emission 25 for each slit 125 based on the digital data read from the line memory 100, thereby producing digital data of the shading estimation device 120.

Here, the focus of the confocal optical system is adjusted to only the reference point on the distance measuring device 92a indicated by the black circle in FIG. 8 but is not adjusted to other portions.

As a result, shading is generated in the thus produced digital data of the shading estimation device 120 read by the data processing section 101 due to the fact that the distance between the lens 19 of the optical head 15 and the InGaAsP layer 121 at the eight slits 125 formed at other positions of the shading estimation device 120 than the reference position thereof corresponding to the reference point on the distance measuring device 92a is not equal to the distance between the lens 19 of the optical head 15 and the InGaAsP layer 121 at the slit 125 formed at the reference position of the shading estimation device 120. Therefore, the signal intensity of the digital data produced by scanning the laminate 123 composed of the InGaAsP layer 121 and the GaAs layer 122 via the slit 125 formed at the reference position of the shading estimation device 120 corresponding to the reference point on the distance measuring device 92a with the laser beam 4 having a wavelength of 640 nm and photoelectrically detecting fluorescence emission 25 released from the laminate 123 composed of the InGaAsP layer 121 and the GaAs layer 122 via the slit 125 is greater than the signal intensity of the digital data produced by scanning the laminate 123 composed of the InGaAsP layer 121 and the GaAs layer 122 via the slits 125 formed in the shading estimation device 120 at positions other than the reference position with the laser beam 4 and photoelectrically detecting fluorescence emission 25 released from the laminate 123 composed of the InGaAsP layer 121 and the GaAs layer 122.

Therefore, if shading correction data are produced, which can correct the digital data so that the signal intensity of the digital data produced by scanning the laminate 123 composed of the InGaAsP layer 121 and the GaAs layer 122 via the eight slits 125 formed in the shading estimation device 120 at positions other than the reference position with the laser beam 4 and photoelectrically detecting fluorescence emission 25 released from the laminate 123 composed of the InGaAsP layer 121 and the GaAs layer 122 becomes equal to the signal intensity of the digital data produced by scanning the laminate 123 composed of the InGaAsP layer 121 and the GaAs layer 122 via the slit 125 formed at the reference position of the shading estimation device 120 corresponding to the reference point on the distance measuring device 92a with the laser beam 4 having a wavelength of 640 nm and photoelectrically detecting fluorescence emission 25 released from the laminate 123 composed of the InGaAsP layer 121 and the GaAs layer 122 via the slit 125 and the shading correction data are stored in the shading correction data storing section 102, it is possible to eliminate the shading in the digital data of the fluorescent substance(s) contained in the micro-array by correcting the digital data of the fluorescent substance(s) contained in the micro-array set in the first opening 51, which is the first sample position in the sample carrier 21, using the shading correction data stored in the shading correction data storing section 102.

In view of the above, based on the thus obtained digital data of the shading estimation device 120, the data processing section 101 produces shading correction data which can correct the digital data of the shading estimation device 120 so that the signal intensity of the digital data produced by scanning the laminate 123 composed of the InGaAsP layer 121 and the GaAs layer 122 via the eight slits 125 formed in the shading estimation device 120 at positions other than the reference position with the laser beam 4 and photoelectrically detecting fluorescence emission 25 released from the laminate 123 composed of the InGaAsP layer 121 and the GaAs layer 122 becomes equal to the signal intensity of the digital data produced by scanning the laminate 123 composed of the InGaAsP layer 121 and the GaAs layer 122 via the slit 125 formed at the reference position of the shading estimation device 120 corresponding to the reference point on the distance measuring device 92a with the laser beam 4 having a wavelength of 640 nm and photoelectrically detecting fluorescence emission 25 released from the laminate 123 composed of the InGaAsP layer 121 and the GaAs layer 122 via the slit 125 and stores the thus produced shading correction data in the shading correction data storing section 102 of the data processing apparatus 35 as shading correction data used when digital data of a fluorescent substance(s) contained in a micro-array are to be produced at 15° C. by setting the micro-array in the first opening 51, which is the first sample position in the sample carrier 21, using the first laser stimulating ray source 1 for emitting a laser beam 4 having a wavelength of 640 nm.

When in this manner shading correction data to be used for producing digital data of a fluorescent substance(s) contained in a micro-array at 15° C. by setting the micro-array in the first opening 51, which is the first sample position in the sample carrier 21, using the first laser stimulating ray source 1 for emitting a laser beam 4 having a wavelength of 640 nm have been produced by the data processing section 101 and stored in the shading correction data storing section 102, the control unit 80 starts irradiating the shading estimation device 120 set in the second opening 52, which is the second sample position in the sample carrier 21, with the laser beam 4 having a wavelength of 640 nm.

Prior to the irradiation of the shading estimation device 120 set in the second opening 52, which is the second sample position with the laser beam 4 having a wavelength of 640 nm, the control unit 80 first reads the temperature coefficient K2 of the second sample position and the distance correction value ΔD2 of the second sample position stored in the EPROM 82, determines the number of drive pulses P to be applied to the stepping motor 76 in accordance with the following formula, outputs a drive signal to the stepping motor 76 to move the lens 19 of the optical head 15 to a predetermined position and holds it at the position:

$$P=P_{640}+A\times\{\Delta D2+K2\times(T-T0)\}.$$

The control unit 80 then outputs a drive signal to the first laser stimulating ray source 1 to turn it on. Similarly to the case where digital data were produced based on the shading estimation device 120 set in the in the first opening 51, which is the first sample position in the sample carrier 21, the InGaAsP layer 121 at the nine slits 125 of the shading estimation device 120 set in the second opening 52, which is the second sample position in the sample carrier 21, is scanned with the laser beam 4 having a wavelength of 640 nm, fluorescence emission 25 released from the laminate 123 composed of the InGaAsP layer 121 and the GaAs layer 122 is photoelectrically detected by the photomultiplier 33 to produce analog data, the analog data are converted by the A/D converter 34 to digital data and the thus produced digital data are stored in the line memory 100.

When the whole surface of the shading estimation device 120 has been scanned with the laser beam 4 and digital data of the shading estimation device 120 have been stored in the line memory 100, the control unit 80 turns off the first laser stimulating ray source 1.

The digital data stored in the line memory 100 are read by the data processing section 101 and the data processing section 101 integrates the signal intensity of fluorescence emission 25 for each slit 125 based on the digital data read from the line memory 100, thereby producing digital data of the shading estimation device 120.

Since the focus of the confocal optical system is adjusted to only the reference point on the distance measuring device 92a indicated by the black circle in FIG. 8 but is not adjusted to other portions, shading is generated in the thus produced digital data of the shading estimation device 120 read by the data processing section 101 due to the fact that the distance between the lens 19 of the optical head 15 and the InGaAsP layer 121 at the nine slits 125 formed in the shading estimation device 120 set in the second opening 52, which is the second sample position in the sample carrier 21, is not equal to the distance between the lens 19 of the optical head 15 and the InGaAsP layer 121 at the slit 125 formed at the reference position of the shading estimation device 120 set in the first opening 51, which is the first sample position in the sample carrier 21.

Therefore, the data processing section 101 produces shading correction data which can correct the digital data of the shading estimation device 120 so that the signal intensity of the digital data produced by scanning the laminate 123 composed of the InGaAsP layer 121 and the GaAs layer 122 via the nine slits 125 formed in the shading estimation device 120 set in the second opening 52, which is the second sample position in the sample carrier 21, with the laser beam 4 and photoelectrically detecting fluorescence emission 25 released from the laminate 123 composed of the InGaAsP layer 121 and the GaAs layer 122 becomes equal to the signal intensity of the digital data produced by scanning the laminate 123 composed of the InGaAsP layer 121 and the GaAs layer 122 via the slit 125 formed at the reference position of the shading estimation device 120 set in the first opening 51, which is the first sample position in the sample carrier 21, corresponding to the reference point on the distance measuring device 92a with the laser beam 4 having a wavelength of 640 nm and photoelectrically detecting fluorescence emission 25 released from the laminate 123 composed of the InGaAsP layer 121 and the GaAs layer 122 via the slit 125 formed at the reference position of the shading estimation device 120 set in the first opening 51, which is the first sample position in the sample carrier 21, and stores the thus produced shading correction data in the shading correction data storing section 102 of the data processing apparatus 35 as shading correction data used when digital data of a fluorescent substance(s) contained in a micro-array are to be produced at 15° C. by setting the micro-array in the second opening 52, which is the second sample position in the sample carrier 21, using the first laser stimulating ray source 1 for emitting a laser beam 4 having a wavelength of 640 nm.

When in this manner the shading correction data to be used for producing digital data of a fluorescent substance(s) contained in a micro-array at 15° C. by setting the micro-array in the second opening 52, which is the second sample position in the sample carrier 21, using the first laser stimulating ray source 1 for emitting a laser beam 4 having a wavelength of 640 nm have been produced by the data processing section 101 and stored in the shading correction data storing section 102, the control unit 80 starts irradiating the shading estimation device 120 set in the third opening 53, which is the third sample position in the sample carrier 21, with the laser beam 4 having a wavelength of 640 nm.

For the shading estimation device 120 set in the third opening 53, which is the third sample position in the sample carrier 21, the control unit 80 reads the temperature coefficient K3 of the third sample position and the distance correction value ΔD3 of the third sample position stored in the EPROM 82, determines the number of drive pulses P to be applied to the stepping motor 76 in accordance with the following formula, outputs a drive signal to the stepping motor 76 to move the lens 19 of the optical head 15 to a predetermined position, holds it at the position, produces digital data of the shading estimation device 120, similarly to the case where the digital data were produced based on the shading estimation device 120 set in the first opening 51, which is the first sample position in the sample carrier 21, by scanning the InGaAsP layer 121 at the nine slits 125 of the shading estimation device 120 set in the third opening 53, which is the third sample position in the sample carrier 21, with laser beam 4 having a wavelength of 640 nm and photoelectrically detecting fluorescence emission 25 released from the laminate 123 composed of the InGaAsP layer 121 and the GaAs layer 122 by the photomultiplier 33, producing analog data and digitizing the analog data by the A/D converter 34, and stores the thus produced digital data in the line memory 100:

$$P = P_{640} + A \times \{\Delta D3 + K3 \times (T-T0)\}.$$

When the whole surface of the shading estimation device 120 has been scanned with the laser beam 4 and digital data of the shading estimation device 120 have been stored in the line memory 100, the control unit 80 turns off the first laser stimulating ray source 1.

The digital data stored in the line memory 100 are read by the data processing section 101 and the data processing section 101 integrates the signal intensity of fluorescence emission 25 for each slit 125 based on the digital data read from the line memory 100, thereby producing digital data of the shading estimation device 120.

Since the focus of the confocal optical system is adjusted to only the reference point on the distance measuring device 92*a* indicated by the black circle in FIG. 8 but is not adjusted to other portions, shading is generated in the thus produced digital data of the shading estimation device 120 read by the data processing section 101 due to the fact that the distance between the lens 19 of the optical head 15 and the InGaAsP layer 121 at the nine slits 125 formed in the shading estimation device 120 set in the third opening 53, which is the third sample position in the sample carrier 21, is not equal to the distance between the lens 19 of the optical head 15 and the InGaAsP layer 121 at the slit 125 formed at the reference position of the shading estimation device 120 set in the first opening 51, which is the first sample position in the sample carrier 21.

Therefore, the data processing section 101 produces shading correction data which can correct the digital data of the shading estimation device 120 so that the signal intensity of the digital data produced by scanning the laminate 123 composed of the InGaAsP layer 121 and the GaAs layer 122 via the nine slits 125 formed in the shading estimation device 120 set in the third opening 53, which is the third sample position in the sample carrier 21, with the laser beam 4 and photoelectrically detecting fluorescence emission 25 released from the laminate 123 composed of the InGaAsP layer 121 and the GaAs layer 122 becomes equal to the signal intensity of the digital data produced by scanning the laminate 123 composed of the InGaAsP layer 121 and the GaAs layer 122 via the slit 125 formed at the reference position of the shading estimation device 120 set in the first opening 51, which is the first sample position in the sample carrier 21, corresponding to the reference point on the distance measuring device 92*a* with the laser beam 4 having a wavelength of 640 nm and photoelectrically detecting fluorescence emission 25 released from the laminate 123 composed of the InGaAsP layer 121 and the GaAs layer 122 via the slit 125 formed at the reference position of the shading estimation device 120 set in the first opening 51, which is the first sample position in the sample carrier 21, and stores the thus produced shading correction data in the shading correction data storing section 102 of the data processing apparatus 35 as shading correction data used when digital data of a fluorescent substance(s) contained in a micro-array are to be produced at 15° C. by setting the micro-array in the third opening 53, which is the third sample position in the sample carrier 21, using the first laser stimulating ray source 1 for emitting a laser beam 4 having a wavelength of 640 nm.

When in this manner the shading correction data to be used for producing digital data of a fluorescent substance(s) contained in a micro-array at 15° C. by setting the micro-array in the third opening 53, which is the third sample position in the sample carrier 21, using the first laser stimulating ray source 1 for emitting a laser beam 4 having a wavelength of 640 nm have been produced by the data processing section 101 and stored in the shading correction data storing section 102, the control unit 80 starts irradiating the shading estimation device 120 set in the fourth opening 54, which is the fourth sample position in the sample carrier 21, with the laser beam 4 having a wavelength of 640 nm.

For the shading estimation device 120 set in the fourth opening 54, which is the fourth sample position in the sample carrier 21, the control unit 80 reads the temperature coefficient K4 of the fourth sample position and the distance correction value ΔD4 of the fourth sample position stored in the EPROM 82, determines the number of drive pulses P to be applied to the stepping motor 76 in accordance with the following formula, outputs a drive signal to the stepping motor 76 to move the lens 19 of the is optical head 15 to a predetermined position, holds it at the position, produces digital data of the shading estimation device 120, similarly to the case where the digital data were produced based on the shading estimation device 120 set in the first opening 51, which is the first sample position in the sample carrier 21, by scanning the InGaAsP layer 121 at the nine slits 125 of the shading estimation device 120 set in the fourth opening 54, which is the fourth sample position in the sample carrier 21, with laser beam 4 having a wavelength of 640 nm and photoelectrically detecting fluorescence emission 25 released from the laminate 123 composed of the InGaAsP layer 121 and the GaAs layer 122 by the photomultiplier 33, producing analog data and digitizing the analog data by the A/D converter 34, and stores the thus produced digital data in the line memory 100:

$$P = P_{640} + A \times \{\Delta D4 + K4 \times (T - T0)\}.$$

When the whole surface of the shading estimation device 120 has been scanned with the laser beam 4 and digital data of the shading estimation device 120 have been stored in the line memory 100, the control unit 80 turns off the first laser stimulating ray source 1.

The digital data stored in the line memory 100 are read by the data processing section 101 and the data processing section 101 integrates the signal intensity of fluorescence emission 25 for each slit 125 based on the digital data read from the line memory 100, thereby producing digital data of the shading estimation device 120.

Since the focus of the confocal optical system is adjusted to only the reference point on the distance measuring device 92*a* indicated by the black circle in FIG. 8 but is not adjusted to other portions, shading is generated in the thus produced digital data of the shading estimation device 120 read by the data processing section 101 due to the fact that the distance between the lens 19 of the optical head 15 and the InGaAsP layer 121 at the nine slits 125 formed in the shading estimation device 120 set in the fourth opening 54, which is the fourth sample position in the sample carrier 21, is not equal to the distance between the lens 19 of the optical head 15 and the InGaAsP layer 121 at the slit 125 formed at the reference position of the shading estimation device 120 set in the first opening 51, which is the first sample position in the sample carrier 21.

Therefore, the data processing section 101 produces shading correction data which can correct the digital data of the shading estimation device 120 so that the signal intensity of the digital data produced by scanning the laminate 123 composed of the InGaAsP layer 121 and the GaAs layer 122 via the nine slits 125 formed in the shading estimation device 120 set in the fourth opening 54, which is the fourth sample position in the sample carrier 21, with the laser beam 4 and photoelectrically detecting fluorescence emission 25 released from the laminate 123 composed of the InGaAsP layer 121 and the GaAs layer 122 becomes equal to the signal intensity of the digital data produced by scanning the laminate 123 composed of the InGaAsP layer 121 and the GaAs layer 122 via the slit 125 formed at the reference position of the shading estimation device 120 set in the first opening 51, which is the first sample position in the sample carrier 21, corresponding to the reference point on the distance measuring device 92*a* with the laser beam 4 having a wavelength of 640 nm and photoelectrically detecting fluorescence emission 25 released from the laminate 123 composed of the InGaAsP layer 121 and the GaAs layer 122 via the slit 125 formed at the reference position of the shading estimation device 120 set in the first opening 51, which is the first sample position in the sample carrier 21, and stores the thus produced shading correction data in the shading correction data storing section 102 of the data processing apparatus 35 as shading correction data used when digital data of a fluorescent substance(s) contained in a micro-array are to be produced at 15° C. by setting the micro-array in the fourth opening 54, which is the fourth sample position in the sample carrier 21, using the first laser stimulating ray source 1 for emitting a laser beam 4 having a wavelength of 640 nm.

When in this manner the shading correction data to be used for producing digital data of a fluorescent substance(s) contained in a micro-array at 15° C. by setting the micro-array in the fourth opening 54, which is the fourth sample position in the sample carrier 21, using the first laser stimulating ray source 1 for emitting a laser beam 4 having a wavelength of 640 nm have been produced by the data processing section 101 and stored in the shading correction data storing section 102, the control unit 80 starts irradiating the shading estimation device 120 set in the fifth opening 55, which is the fifth sample position in the sample carrier 21, with the laser beam 4 having a wavelength of 640 nm.

For the shading estimation device 120 set in the fifth opening 55, which is the fifth sample position in the sample carrier 21, the control unit 80 reads the temperature coefficient K5 of the fifth sample position and the distance correction value ΔD5 of the fifth sample position stored in the EPROM 82, determines the number of drive pulses P to be applied to the stepping motor 76 in accordance with the following formula, outputs a drive signal to the stepping motor 76 to move the lens 19 of the optical head 15 to a predetermined position, holds it at the position, produces digital data of the shading estimation device 120, similarly to the case where the digital data were produced based on the shading estimation device 120 set in the first opening 51, which is the first sample position in the sample carrier 21, by scanning the InGaAsP layer 121 at the nine slits 125 of the shading estimation device 120 set in the fifth opening 55, which is the fifth sample position in the sample carrier 21, with laser beam 4 having a wavelength of 640 nm and photoelectrically detecting fluorescence emission 25 released from the laminate 123 composed of the InGaAsP layer 121 and the GaAs layer 122 by the photomultiplier 33, producing analog data and digitizing the analog data by the A/D converter 34, and stores the thus produced digital data in the line memory 100:

$$P = P_{640} + A \times \{\Delta D5 + K5 \times (T - T0)\}.$$

When the whole surface of the shading estimation device 120 has been scanned with the laser beam 4 and digital data of the shading estimation device 120 have been stored in the line memory 100, the control unit 80 turns off the first laser stimulating ray source 1.

The digital data stored in the line memory 100 are read by the data processing section 101 and the data processing section 101 integrates the signal intensity of fluorescence emission 25 for each slit 125 based on the digital data read from the line memory 100, thereby producing digital data of the shading estimation device 120.

Since the focus of the confocal optical system is adjusted to only the reference point on the distance measuring device 92*a* indicated by the black circle in FIG. 8 but is not adjusted to other portions, shading is generated in the thus produced digital data of the shading estimation device 120 read by the data processing section 101 due to the fact that the distance between the lens 19 of the optical head 15 and the InGaAsP layer 121 at the nine slits 125 formed in the shading estimation device 120 set in the fifth opening 55, which is the fifth sample position in the sample carrier 21, is not equal to the distance between the lens 19 of the optical head 15 and the InGaAsP layer 121 at the slit 125 formed at the reference position of the shading estimation device 120 set in the first opening 51, which is the first sample position in the sample carrier 21.

Therefore, the data processing section 101 produces shading correction data which can correct the digital data of the shading estimation device 120 so that the signal intensity of the digital data produced by scanning the laminate 123 composed of the InGaAsP layer 121 and the GaAs layer 122 via the nine slits 125 formed in the shading estimation device 120 set in the fifth opening 55, which is the fifth sample position in the sample carrier 21, with the laser beam 4 and photoelectrically detecting fluorescence emission 25 released from the laminate 123 composed of the InGaAsP layer 121 and the GaAs layer 122 becomes equal to the signal intensity of the digital data produced by scanning the laminate 123 composed of the InGaAsP layer 121 and the GaAs layer 122 via the slit 125 formed at the reference position of the shading estimation device 120 set in the first opening 51, which is the first sample position in the sample carrier 21, corresponding to the reference point on the distance measuring device 92a with the laser beam 4 having a wavelength of 640 nm and photoelectrically detecting fluorescence emission 25 released from the laminate 123 composed of the InGaAsP layer 121 and the GaAs layer 122 via the slit 125 formed at the reference position of the shading estimation device 120 set in the first opening 51, which is the first sample position in the sample carrier 21, and stores the thus produced shading correction data in the shading correction data storing section 102 of the data processing apparatus 35 as shading correction data used when digital data of a fluorescent substance(s) contained in a micro-array are to be produced at 15° C. by setting the micro-array in the fifth opening 55, which is the fifth sample position in the sample carrier 21, using the first laser stimulating ray source 1 for emitting the laser beam 4 having a wavelength of 640 nm.

When in this manner shading correction data to be used for producing digital data of the fluorescent substance(s) contained in the micro-array at 15° C. in the scanner by setting micro-arrays in the first opening 51 to the fifth opening 55, which are the first sample position to the fifth sample position in the sample carrier 21, and using the first laser stimulating ray source 1 for emitting the laser beam 4 having a wavelength of 640 nm have been produced and stored in the shading correction data storing section 102 of the data processing apparatus 35, the control unit 80 sets the temperature in the scanner to 25° C. and similarly to when the shading correction data were produced at 15° C. by scanning the shading estimation device 120 set in the first opening 51 to the fifth opening 55, which are the first sample position to the fifth sample position in the sample carrier 21, with the laser beam 4 having a wavelength of 640 nm, shading correction data to be used for producing digital data of the fluorescent substance(s) contained in the micro-array at 25° C. in the scanner by setting micro-arrays in the first opening 51 to the fifth opening 55, which are the first sample position to the fifth sample position in the sample carrier 21, and using the first laser stimulating ray source 1 for emitting the laser beam 4 having a wavelength of 640 nm are produced and stored in the shading correction data storing section 102 of the data processing apparatus 35.

Then, the control unit 80 sets the temperature in the scanner to 35° C. and similarly to when the shading correction data were produced at 15° C. by scanning the shading estimation device 120 set in the first opening 51 to the fifth opening 55, which are the first sample position to the fifth sample position in the sample carrier 21, with the laser beam 4 having a wavelength of 640 nm, shading correction data to be used for producing digital data of the fluorescent substance(s) contained in the micro-array at 35° C. in the scanner by setting micro-arrays in the first opening 51 to the fifth opening 55, which are the first sample position to the fifth sample position in the sample carrier 21, and using the first laser stimulating ray source 1 for emitting the laser beam 4 having a wavelength of 640 nm are produced and stored in the shading correction data storing section 102 of the data processing apparatus 35.

When in this manner the shading correction data to be used for producing digital data of the fluorescent substance (s) contained in the micro-array by setting micro-arrays are set in the first opening 51 to the fifth opening 55, which are the first sample position to the fifth sample position in the sample carrier 21, and using the first laser stimulating ray source 1 for emitting the laser beam 4 having a wavelength of 640 nm in the case where the temperatures in the scanner are set to 15° C., 25° C. and 35° C. have been produced and stored in the shading correction data storing section 102 of the data processing apparatus 35, the control unit 80 turns off the first laser stimulating ray source 1, outputs a drive signal to the stepping motor 76, thereby causing it to return the sample stage 20 to the original position thereof and sets the temperature in the scanner to 15° C. while the confocal switching member 31 is held so that the pinhole 32a having the smallest diameter is located in the optical path.

At the same time, the control unit 80 reads from the EPROM 82 the focus position data $P_{532}$ of the confocal optical system when the second laser stimulating ray source 2 is used, the temperature coefficient K1 of the first sample position, the distance correction value $\Delta D1$ of the first sample position, the focus position data of the confocal optical system for the laser beam 4 having a wavelength of 532 nm and the average value T0 of the temperature in the scanner when the focus position data of the confocal optical system and the coefficient of the nth order function were obtained, determines the number of drive pulses P to be applied to the stepping motor 76 in accordance with the following formula (1) using a temperature T in the scanner detected by and received from the temperature sensor 84, outputs a drive signal to the stepping motor 76 to move the lens 19 of the optical head 15 to a predetermined position and holds it at the position:

$$P=P_\lambda+A\times\{\Delta Di+Ki\times(T-T0)\} \tag{1}.$$

In the formula (1), A designates a conversion coefficient between drive pulses and a distance, $\lambda$ designates the wavelength of a laser beam 4 used for stimulating a labeling substance and i designates an integer from 1 to 5 and indicates the position of one of openings 51, 52, 53, 54, 55. In this case, $P_\lambda=P_{532}$, $\Delta Di=\Delta D1$ and Ki=K1.

The control unit 80 then outputs a drive signal to filter unit motor 85, thereby causing it to move the filter unit 27 so that the filter 28b having a property to cut off a light component having a wavelength of 532 nm and transmit light components having wavelengths longer than 532 nm is located in the optical path.

The laser beam 4 emitted from the second laser stimulating ray source 2 passes through a collimator lens 9, thereby being made a parallel beam, and advances to the first dichroic mirror 7 to be reflected thereby.

The laser beam 4 reflected by the first dichroic mirror 7 passes through the second dichroic mirror 8 and enters the optical head 15.

The laser beam 4 entering the optical unit 15 is reflected by the mirror 16, passes through the hole 17 formed in the perforated mirror 18 and through the lens 19 to impinge on the shading estimation device 120 set in the first opening 51, which is the first sample position in the sample carrier 21.

Since the sample stage 20 is moved by the main scanning motor 43 in the main scanning direction indicated by the arrow X in FIG. 3 with a pixel pitch substantially equal to the diameter of the laser beam 4 and is moved by the sub-scanning motor 47 in the sub-scanning direction indicated by the arrow Y in FIG. 3, the whole surface of the shading estimation device 120 set in the first opening 51, which is the first sample position in the sample carrier 21, is scanned with the laser beam 4.

When being irradiated through the nine slits regularly formed in the shading estimation device 120 with the laser beam 4, the laminate 123 composed of the InGaAsP layer 121 and the GaAs layer 122 is stimulated to release fluorescence emission 25.

The fluorescence emission 25 released from the laminate 123 composed of the InGaAsP layer 121 and the GaAs layer 122 passes through the lens 19, thereby being made a parallel beam, and is reflected by the perforated mirror 18, thereby entering the filter unit 27.

Since the filter unit 27 has been moved so that the filter 28b is located in the optical path, the fluorescence emission enters the filter 28b, thereby cutting light having a wavelength of 532 nm and transmitting only light having a wavelength longer than 532 nm.

Since the wavelength of fluorescence emission 25 is longer than that of the laser beam 4, i.e., the stimulating ray, the laser beam 4 is cut off by the filter 28b and only the fluorescence emission 25 released from the laminate 123 composed of the InGaAsP layer 121 and the GaAs layer 122 passes through the filter 28b.

The fluorescence emission transmitted through the filter 28b is reflected by the mirror 29, condensed by the lens 30 onto the pinhole 32a having the smallest diameter and photoelectrically detected by the photomultiplier 33, thereby producing analog data.

The analog data produced by the photomultiplier 33 are converted to digital data by the A/D converter 34 and the digital data are forwarded to the data processing apparatus 35.

Digital data converted by the A/D converter 34 and forwarded to the data processing apparatus 35 are stored in the line memory 100.

As described above, shading is generated in the thus produced digital data of the shading estimation device 120 stored in the line memory 100 due to the fact that the distance between the lens 19 of the optical head 15 and the InGaAsP layer 121 at the eight slits 125 formed at other positions of the shading estimation device 120 than the reference position thereof corresponding to the reference point on the distance measuring device 92a is not equal to the distance between the lens 19 of the optical head 15 and the InGaAsP layer 121 at the slit 125 formed at the reference position of the shading estimation device 120.

Therefore, similarly to the case where the shading estimation device 120 set in the first opening 51, which is the first sample position in the sample carrier 21, was scanned with the laser beam 4 having a wavelength of 640 nm, the data processing section 101, based on the thus obtained digital data of the shading estimation device 120, produces shading correction data which can correct the digital data of the shading estimation device 120 so that the signal intensity of the digital data produced by scanning the laminate 123 composed of the InGaAsP layer 121 and the GaAs layer 122 via the eight slits 125 formed at other positions of the shading estimation device 120 than the reference position thereof with the laser beam 4 having a wavelength of 532 nm and photoelectrically detecting fluorescence emission 25 released from the laminate 123 composed of the InGaAsP layer 121 and the GaAs layer 122 becomes equal to the signal intensity of the digital data produced by scanning the laminate 123 composed of the InGaAsP layer 121 and the GaAs layer 122 via the slit 125 formed at the reference position of the shading estimation device 120 corresponding to the reference point on the distance measuring device 92a with the laser beam 4 having a wavelength of 532 nm and photoelectrically detecting fluorescence emission 25 released from the laminate 123 composed of the InGaAsP layer 121 and the GaAs layer 122 via the slit 125 formed at the reference position of the shading estimation device 120 and stores the thus produced shading correction data in the shading correction data storing section 102 of the data processing apparatus 35 as shading correction data to be used for producing digital data of a fluorescent substance(s) contained in a micro-array at 15° C. by setting the micro-array in the second opening 52, which is the second sample position in the sample carrier 21, using the second laser stimulating ray source 2 for emitting a laser beam 4 having a wavelength of 532 nm.

When in this manner the shading correction data to be used for producing digital data of a fluorescent substance(s) contained in a micro-array are at 15° C. by setting the micro-array in the first opening 51, which is the first sample position in the sample carrier 21, using the second laser stimulating ray source 2 for emitting a laser beam 4 having a wavelength of 532 nm have been produced by the data processing section 101 and stored in the shading correction data storing section 102, the control unit 80 starts irradiating the shading estimation device 120 set in the second opening 52, which is the second sample position in the sample carrier 21, with the laser beam 4 having a wavelength of 532 nm.

Prior to the irradiation of the shading estimation device 120 set in the second opening 52, which is the second sample position, with the laser beam 4 having a wavelength of 532 nm, the control unit 80 first reads the temperature coefficient K2 of the second sample position and the distance correction value ΔD2 of the second sample position stored in the EPROM 82, determines the number of drive pulses P to be applied to the stepping motor 76 in accordance with the following formula, outputs a drive signal to the stepping motor 76 to move the lens 19 of the optical head 15 to a predetermined position and holds it at the position:

$$P = P_{532} + A \times \{\Delta D2 + K2 \times (T - T0)\}.$$

The control unit 80 then outputs a drive signal to the second laser stimulating ray source 2 to turn it on. Similarly to the case where digital data were produced based on the shading estimation device 120 set in the in the first opening 51, which is the first sample position in the sample carrier 21, the InGaAsP layer 121 at the nine slits 125 of the shading estimation device 120 set in the second opening 52, which is the second sample position in the sample carrier 21, is scanned with the laser beam 4 having a wavelength of 532 nm, fluorescence emission 25 released from the laminate 123 composed of the InGaAsP layer 121 and the GaAs layer 122 is photoelectrically detected by the photomultiplier 33 to produce analog data, the analog data are converted by the A/D converter 34 to digital data and the thus produced digital data are stored in the line memory 100.

When the whole surface of the shading estimation device 120 has been scanned with the laser beam 4 and digital data of the shading estimation device 120 have been stored in the line memory 100, the control unit 80 turns off the second laser stimulating ray source 2.

The digital data stored in the line memory 100 are read by the data processing section 101 and the data processing section 101 integrates the signal intensity of fluorescence emission 25 for each slit 125 based on the digital data read from the line memory 100, thereby producing digital data of the shading estimation device 120.

As described above, since the focus of the confocal optical system is adjusted to only the reference point on the distance measuring device 92a indicated by the black circle in FIG. 8 but is not adjusted to other portions, shading is generated in the thus produced digital data of the shading estimation device 120 read by the data processing section 101 due to the fact that the distance between the lens 19 of the optical head 15 and the InGaAsP layer 121 at the nine slits 125 formed in the shading estimation device 120 set in the second opening 52, which is the second sample position in the sample carrier 21, is not equal to the distance between the lens 19 of the optical head 15 and the InGaAsP layer 121 at the slit 125 formed at the reference position of the shading estimation device 120 set in the first opening 51, which is the first sample position in the sample carrier 21.

Therefore, similarly to the case where the shading estimation device 120 set in the first opening 51, which is the first sample position in the sample carrier 21, was scanned with the laser beam 4 having a wavelength of 640 nm, the data processing section 101 produces shading correction data which can correct the digital data of the shading estimation device 120 so that the signal intensity of the digital data produced by scanning the laminate 123 composed of the InGaAsP layer 121 and the GaAs layer 122 via the nine slits 125 formed in the shading estimation device 120 set in the second opening 52, which is the second sample position in the sample carrier 21, with the laser beam 4 having a wavelength of 532 nm and photoelectrically detecting fluorescence emission 25 released from the laminate 123 composed of the InGaAsP layer 121 and the GaAs layer 122 becomes equal to the signal intensity of the digital data produced by scanning the laminate 123 composed of the InGaAsP layer 121 and the GaAs layer 122 via the slit 125 formed at the reference position of the shading estimation device 120 set in the first opening 51, which is the first sample position in the sample carrier 21, corresponding to the reference point on the distance measuring device 92a with the laser beam 4 having a wavelength of 532 nm and photoelectrically detecting fluorescence emission 25 released from the laminate 123 composed of the InGaAsP layer 121 and the GaAs layer 122 via the slit 125 formed at the reference position of the shading estimation device 120 set in the first opening 51, which is the first sample position in the sample carrier 21, and stores the thus produced shading correction data in the shading correction data storing section 102 of the data processing apparatus 35 as shading correction data to be used for producing digital data of a fluorescent substance(s) contained in a micro-array at 15° C. by setting the micro-array in the second opening 52, which is the second sample position in the sample carrier 21, using the second laser stimulating ray source 2 for emitting a laser beam 4 having a wavelength of 532 nm.

In the case where the shading estimation device 120 set in one of the third opening 53 to the fifth opening 55, which are the third sample position to the fifth sample position, is scanned with the laser beam 4 having a wavelength of 532 nm, the scanning is conducted similarly to the case where the shading estimation device 120 set in one of the third opening 53 to the fifth opening 55, which are the third sample position to the fifth sample position, was scanned with the laser beam 4 having a wavelength of 640 nm, except that the focus position data $P_{532}$ produced using the second laser stimulating ray source 2 for emitting a laser beam 4 having a wavelength of 532 nm are used, and shading correction data are produced and stored in the shading correction data storing section 102 of the data processing apparatus 35.

When in this manner shading correction data to be used for producing digital data of the fluorescent substance(s) contained in the micro-array at 15° C. in the scanner by setting micro-arrays in the first opening 51 to the fifth opening 55 which, are the first sample position to the fifth sample position in the sample carrier 21, and using the second laser stimulating ray source 2 for emitting the laser beam 4 having a wavelength of 532 nm have been produced and stored in the shading correction data storing section 102 of the data processing apparatus 35, the control unit 80 sets the temperature in the scanner to 25° C. and similarly to when the shading correction data were produced at 15° C. by scanning the shading estimation device 120 set in the first opening 51 to the fifth opening 55, which are the first sample position to the fifth sample position in the sample carrier 21, with the laser beam 4 having a wavelength of 532 nm, shading correction data to be used for producing digital data of the fluorescent substance(s) contained in the micro-array at 25° C. in the scanner by setting micro-arrays in the first opening 51 to the fifth opening 55, which are the first sample position to the fifth sample position in the sample carrier 21, and using the second laser stimulating ray source 2 for emitting the laser beam 4 having a wavelength of 532 nm are produced and stored in the shading correction data storing section 102 of the data processing apparatus 35.

Then, the control unit 80 sets the temperature in the scanner to 35° C. and similarly to when the shading correction data were produced at 15° C. by scanning the shading estimation device 120 set in the first opening 51 to the fifth opening 55, which are the first sample position to the fifth sample position in the sample carrier 21, with the laser beam 4 having a wavelength of 532 nm, shading correction data to be used for producing digital data of the fluorescent substance(s) contained in the micro-array at 35° C. in the scanner by setting micro-arrays in the first opening 51 to the fifth opening 55, which are the first sample position to the fifth sample position in the sample carrier 21, and using the second laser stimulating ray source 2 for emitting the laser beam 4 having a wavelength of 532 nm are produced and stored in the shading correction data storing section 102 of the data processing apparatus 35.

When in this manner the shading correction data to be used for producing digital data of the fluorescent substance(s) contained in the micro-array by setting micro-arrays in the first opening 51 to the fifth opening 55 which, are the first sample position to the fifth sample position in the sample carrier 21, and using the second laser stimulating ray source 2 for emitting the laser beam 4 having a wavelength of 532 nm in the case where the temperatures in the scanner are set to 15° C., 25° C. and 35° C. have been produced and stored in the shading correction data storing section 102 of the data processing apparatus 35, the control unit 80 turns off the second laser stimulating ray source 2, outputs a drive signal to the stepping motor 76, thereby causing it to return the sample stage 20 to the original position thereof and sets the temperature in the scanner to 15° C. while the confocal switching member 31 is held so that the pinhole 32a having the smallest diameter is located in the optical path.

At the same time, the control unit 80 reads from the EPROM 82 the focus position data $P_{473}$ of the confocal optical system when the third laser stimulating ray source 3 is used, the temperature coefficient K1 of the first sample position, the distance correction value ΔD1 of the first sample position, the focus position data of the confocal optical system for the laser beam 4 having a wavelength of 473 nm and the average value T0 of the temperature in the scanner when the focus position data of the confocal optical system and the coefficient of the nth order function were obtained, determines the number of drive pulses P to be applied to the stepping motor 76 in accordance with the following formula (1) using a temperature T in the scanner detected by and received from the temperature sensor 84, outputs a drive signal to the stepping motor 76 to move the lens 19 of the optical head 15 to a predetermined position and holds it at the position:

$$P=P_\lambda+A\times\{\Delta Di+Ki\times(T-T0)\} \qquad (1).$$

In the formula (1), A designates a conversion coefficient between drive pulses and a distance, λ designates the wavelength of a laser beam 4 used for stimulating a labeling substance and i designates an integer from 1 to 5 and indicates the position of one of openings 51, 52, 53, 54, 55. In this case, $P_\lambda=P_{473}$, $\Delta Di=\Delta D1$ and $Ki=K1$.

The control unit 80 then outputs a drive signal to filter unit motor 85, thereby causing it to move the filter unit 27 so that the filter 28c having a property to cut off a light component having a wavelength of 473 nm and transmit light components having wavelengths longer than 473 nm is located in the optical path.

The laser beam 4 emitted from the third laser stimulating ray source 3 passes through a collimator lens 10, thereby being made a parallel beam, and is reflected by second dichroic mirror 8 to enter the optical head 15.

The laser beam 4 entering the optical unit 15 is reflected by the mirror 16, passes through the hole 17 formed in the perforated mirror 18 and through the lens 19 to impinge on the shading estimation device 120 set in the first opening 51, which is the first sample position in the sample carrier 21.

Since the sample stage 20 is moved by the main scanning motor 43 in the main scanning direction indicated by the arrow X in FIG. 3 with a pixel pitch substantially equal to the diameter of the laser beam 4 and is moved by the sub-scanning motor 47 in the sub-scanning direction indicated by the arrow Y in FIG. 3, the whole surface of the shading estimation device 120 set in the first opening 51, which is the first sample position in the sample carrier 21, is scanned with the laser beam 4 having a wavelength of 473 nm.

When being irradiated through the nine slits regularly formed in the shading estimation device 120 with the laser beam 4, the laminate 123 composed of the InGaAsP layer 121 and the GaAs layer 122 is stimulated to release fluorescence emission 25.

The fluorescence emission 25 released from the laminate 123 composed of the InGaAsP layer 121 and the GaAs layer 122 passes through the lens 19, thereby being made a parallel beam, and is reflected by the perforated mirror 18, thereby entering the filter unit 27.

Since the filter unit 27 has been moved so that the filter 28c is located in the optical path, the fluorescence emission enters the filter 28c, thereby cutting light having a wavelength of 473 nm and transmitting only light having a wavelength longer than 473 nm.

Since the wavelength of fluorescence emission 25 is longer than that of the laser beam 4, i.e., the stimulating ray, the laser beam 4 is cut off by the filter 28c and only the fluorescence emission 25 released from the laminate 123 composed of the InGaAsP layer 121 and the GaAs layer 122 passes through the filter 28c.

The fluorescence emission transmitted through the filter 28c is reflected by the mirror 29, condensed by the lens 30 onto the pinhole 32a having the smallest diameter and photoelectrically detected by the photomultiplier 33, thereby producing analog data.

The analog data produced by the photomultiplier 33 are converted to digital data by the A/D converter 34 and the digital data are forwarded to the data processing apparatus 35.

Digital data converted by the A/D converter 34 and sent to the data processing apparatus 35 are stored in the line memory 100.

When the whole surface of the shading estimation device 120 has been scanned with the laser beam 4 and digital data of the shading estimation device 120 have been stored in the line memory 100, the control unit 80 turns off the third laser stimulating ray source 2.

As described above, shading is generated in the thus produced digital data of the shading estimation device 120 stored in the line memory 100 due to the fact that the distance between the lens 19 of the optical head 15 and the InGaAsP layer 121 at the eight slits 125 formed at other positions of the shading estimation device 120 than the reference position thereof corresponding to the reference point on the distance measuring device 92a is not equal to the distance between the lens 19 of the optical head 15 and the InGaAsP layer 121 at the slit 125 formed at the reference position of the shading estimation device 120.

Therefore, similarly to the case where the shading estimation device 120 set in the first opening 51, which is the first sample position in the sample carrier 21, was scanned with the laser beam 4 having a wavelength of 640 nm, the data processing section 101, based on the thus obtained digital data of the shading estimation device 120, produces shading correction data which can correct the digital data of the shading estimation device 120 so that the signal intensity of the digital data produced by scanning the laminate 123 composed of the InGaAsP layer 121 and the GaAs layer 122 via the eight slits 125 formed at other positions of the shading estimation device 120 than the reference position thereof with the laser beam 4 having a wavelength of 473 nm and photoelectrically detecting fluorescence emission 25 released from the laminate 123 composed of the InGaAsP layer 121 and the GaAs layer 122 becomes equal to the signal intensity of the digital data produced by scanning the laminate 123 composed of the InGaAsP layer 121 and the GaAs layer 122 via the slit 125 formed at the reference position of the shading estimation device 120 corresponding to the reference point on the distance measuring device 92a with the laser beam 4 having a wavelength of 473 nm and photoelectrically detecting fluorescence emission 25 released from the laminate 123 composed of the InGaAsP layer 121 and the GaAs layer 122 via the slit 125 formed at the reference position of the shading estimation device 120 and stores the thus produced shading correction data in the shading correction data storing section 102 of the data processing apparatus 35 as shading correction data to be used for producing digital data of a fluorescent substance(s) contained in a micro-array at 15° C. by setting the micro-array in the second opening 52, which is the second sample position in the sample carrier 21, using the third laser stimulating ray source 3 for emitting a laser beam 4 having a wavelength of 473 nm.

When in this manner the shading correction data to be used for producing digital data of a fluorescent substance(s) contained in a micro-array at 15° C. by setting the micro-array in the first opening 51, which is the first sample position in the sample carrier 21, and using the third laser stimulating ray source 3 for emitting a laser beam 4 having a wavelength of 473 nm have been produced by the data processing section 101 and stored in the shading correction data storing section 102, the control unit 80 starts irradiating the shading estimation device 120 set in the second opening 52, which is the second sample position in the sample carrier 21, with the laser beam 4 having a wavelength of 473 nm.

Prior to the irradiation of the shading estimation device 120 set in the second opening 52, which is the second sample position, with the laser beam 4 having a wavelength of 473 nm, the control unit 80 first reads the temperature coefficient K2 of the second sample position and the distance correction value ΔD2 of the second sample position stored in the EPROM 82, determines the number of drive pulses P to be applied to the stepping motor 76 in accordance with the following formula, outputs a drive signal to the stepping motor 76 to move the lens 19 of the optical head 15 to a predetermined position and holds it at the position:

$$P=P_{473}+A\times\{\Delta D2+K2\times(T-T0)\}.$$

The control unit 80 then outputs a drive signal to the second laser stimulating ray source 3 to turn it on. Similarly to the case where digital data were produced based on the shading estimation device 120 set in the first opening 51, which is the first sample position in the sample carrier 21, the InGaAsP layer 121 at the nine slits 125 of the shading estimation device 120 set in the second opening 52, which is the second sample position in the sample carrier 21, is scanned with the laser beam 4 having a wavelength of 473 nm, fluorescence emission 25 released from the laminate 123 composed of the InGaAsP layer 121 and the GaAs layer 122 is photoelectrically detected by the photomultiplier 33 to produce analog data, the analog data are converted by the A/D converter 34 to digital data and the thus produced digital data are stored in the line memory 100.

When the whole surface of the shading estimation device 120 has been scanned with the laser beam 4 and digital data of the shading estimation device 120 have been stored in the line memory 100, the control unit 80 turns off the third laser stimulating ray source 2.

The digital data stored in the line memory 100 are read by the data processing section 101 and the data processing section 101 integrates the signal intensity of fluorescence emission 25 for each slit 125 based on the digital data read from the line memory 100, thereby producing digital data of the shading estimation device 120.

As described above, since the focus of the confocal optical system is adjusted to only the reference point on the distance measuring device 92a indicated by the black circle in FIG. 8 but is not adjusted to other portions, shading is generated in the thus produced digital data of the shading estimation device 120 read by the data processing section 101 due to the fact that the distance between the lens 19 of the optical head 15 and the InGaAsP layer 121 at the nine slits 125 formed in the shading estimation device 120 set in the second opening 52, which is the second sample position in the sample carrier 21, is not equal to the distance between the lens 19 of the optical head 15 and the InGaAsP layer 121 at the slit 125 formed at the reference position of the shading estimation device 120 set in the first opening 51, which is the first sample position in the sample carrier 21.

Therefore, similarly to the case where the shading estimation device 120 set in the first opening 51, which is the first sample position in the sample carrier 21, was scanned with the laser beam 4 having a wavelength of 640 nm, the data processing section 101 produces shading correction data which can correct the digital data of the shading estimation device 120 so that the signal intensity of the digital data produced by scanning the laminate 123 composed of the InGaAsP layer 121 and the GaAs layer 122 via the nine slits 125 formed in the shading estimation device 120 set in the second opening 52, which is the second sample position in the sample carrier 21, with the laser beam 4 having a wavelength of 473 nm and photoelectrically detecting fluorescence emission 25 released from the laminate 123 composed of the InGaAsP layer 121 and the GaAs layer 122 becomes equal to the signal intensity of the digital data produced by scanning the laminate 123 composed of the InGaAsP layer 121 and the GaAs layer 122 via the slit 125 formed at the reference position of the shading estimation device 120 set in the first opening 51, which is the first sample position in the sample carrier 21, corresponding to the reference point on the distance measuring device 92a with the laser beam 4 having a wavelength of 473 nm and photoelectrically detecting fluorescence emission 25 released from the laminate 123 composed of the InGaAsP layer 121 and the GaAs layer 122 via the slit 125 formed at the reference position of the shading estimation device 120 set in the first opening 51, which is the first sample position in the sample carrier 21, and stores the thus produced shading correction data in the shading correction data storing section 102 of the data processing apparatus 35 as shading correction data to be used for producing digital data of a fluorescent substance(s) contained in a micro-array at 15° C. by setting the micro-array in the second opening 52, which is the second sample position in the sample carrier 21, using the third laser stimulating ray source 3 for emitting a laser beam 4 having a wavelength of 473 nm.

In the case where the shading estimation device 120 set in one of the third opening 53 to the fifth opening 55, which are the third sample position to the fifth sample position, is scanned with the laser beam 4 having a wavelength of 473 nm, the scanning is conducted similarly to the case where the shading estimation device 120 set in one of the third opening 53 to the fifth opening 55, which are the third sample position to the fifth sample position, was scanned with the laser beam 4 having a wavelength of 640 nm, except that the focus position data $P_{473}$ produced using the third laser stimulating ray source 3 for emitting a laser beam 4 having a wavelength of 473 nm are used, and shading correction data are produced and stored in the shading correction data storing section 102 of the data processing apparatus 35.

When in this manner shading correction data to be used for producing digital data of the fluorescent substance(s) contained in the micro-array at 15° C. in the scanner by setting micro-arrays in the first opening 51 to the fifth opening 55, which are the first sample position to the fifth sample position in the sample carrier 21, and using the third laser stimulating ray source 3 for emitting the laser beam 4 having a wavelength of 473 nm have been produced and stored in the shading correction data storing section 102 of the data processing apparatus 35, the control unit 80 sets the temperature in the scanner to 25° C. and similarly to when the shading correction data were produced at 15° C. by scanning the shading estimation device 120 set in the first opening 51 to the fifth opening 55, which are the first sample position to the fifth sample position in the sample carrier 21, with the laser beam 4 having a wavelength of 473 nm, shading correction data to be used for producing digital data of the fluorescent substance(s) contained in the micro-array at 25° C. in the scanner by setting micro-arrays in the first opening 51 to the fifth opening 55, which are the first sample position to the fifth sample position in the sample carrier 21, and using the third laser stimulating ray source 3 for emitting the laser beam 4 having a wavelength of 473 nm are produced and stored in the shading correction data storing section 102 of the data processing apparatus 35.

Then, the control unit 80 sets the temperature in the scanner to 35° C. and similarly to when the shading correction data were produced at 15° C. by scanning the shading estimation device 120 set in the first opening 51 to the fifth opening 55, which are the first sample position to the fifth sample position in the sample carrier 21, with the laser beam 4 having a wavelength of 473 nm, shading correction data to be used for producing digital data of the fluorescent substance(s) contained in the micro-array at 35° C. in the scanner by setting micro-arrays in the first opening 51 to the fifth opening 55, which are the first sample position to the fifth sample position in the sample carrier 21, and using the second laser stimulating ray source 2 for emitting the laser beam 4 having a wavelength of 473 nm are produced and stored in the shading correction data storing section 102 of the data processing apparatus 35.

According to this embodiment, shading correction data can be produced merely by scanning the shading correction device 120 with the laser beam 4 having a wavelength of 640 nm, the laser beam 4 having a wavelength of 532 nm and the laser beam 4 having a wavelength of 473 nm to produce digital data of the shading correction device 120, and producing, based on the thus produced digital data of the shading correction device 120, digital data which can correct the digital data of the shading correction device 120 so that the signal intensity of the digital data produced by scanning the laminate 123 composed of the InGaAsP layer 121 and the GaAs layer 122 via the nine slits 125 formed in the shading estimation device 120 with the laser beam 4 having a wavelength of 640 nm, the laser beam 4 having a wavelength of 532 nm and the laser beam 4 having a wavelength of 473 nm and photoelectrically detecting fluorescence emission 25 released from the laminate 123 composed of the InGaAsP layer 121 and the GaAs layer 122 becomes equal to the signal intensity of the digital data produced by scanning the laminate 123 composed of the InGaAsP layer 121 and the GaAs layer 122 via the slit 125 formed at the reference position of the shading estimation device 120 corresponding to the reference point shown in FIG. 8 on the distance measuring device 92a set in the first opening 51, which is the first sample position in the sample carrier 21, with the laser beam 4 having a wavelength of 640 nm, the laser beam 4 having a wavelength of 532 nm and the laser beam 4 having a wavelength of 473 nm and photoelectrically detecting fluorescence emission 25 released from the laminate 123 composed of the InGaAsP layer 121 and the GaAs layer 122 via the slit 125 formed at the reference position of the shading estimation device 120 set in the first opening 51, which is the first sample position in the sample carrier 21, and it is unnecessary to effect fitting on the curves A, B and C obtained by plotting the integrated values of signal intensity of digital data produced by irradiating the focus determination device 95 with the laser beam 4 having a wavelength of 640 nm, the laser beam 4 having a wavelength of 532 nm and the laser beam 4 having a wavelength of 473 nm with an nth order function to calculate a coefficient of the nth order function for each wavelength of the laser beam 4, produce measurement point displacement data V1 of the first sample position to measurement point displacement data V5 of the fifth sample position, or produce shading correction data based on the coefficient of the nth order function calculated for each wavelength of the laser beam 4 and the measurement point displacement data V1 of the first sample position to the measurement point displacement data V5 of the fifth sample position. Therefore, shading correction data can be produced by simple calculation.

Further, in the case where a spot 97 containing a fluorescent dye(s) is formed on a slide glass plate 96 and irradiated with a laser beam 4 to determine the focus position of the confocal optical system, the fluorescent dye(s) is sometimes degraded during the irradiation with the laser beam 4, thereby decreasing the amount of fluorescence emission released from the fluorescent dye(s) with the elapse of time, and it is sometimes difficult to accurately determine the focus position of the confocal optical system and impossible to produce shading correction data in a desired manner. However, according to this embodiment, since the laminate 123 composed of the InGaAsP layer 121 and the GaAs layer 122 is not degraded by irradiation with the laser beam 4, it is possible to produce shading correction data in a desired manner and the focus position determination device 110 can be repeatedly used for producing the shading correction data.

The present invention has thus been shown and described with reference to specific embodiments. However, it should be noted that the present invention is in no way limited to the details of the described arrangements but changes and modifications may be made without departing from the scope of the appended claims.

For example, in the above described embodiments, although the distance data representing the distance between the distance measuring devices 92a, 92b, 92c, 92d, 92e set in the first opening 51 to the fifth opening 55 in the sample carrier 21 and the lens 19 of the optical head 15 are produced by the electrostatic capacitance displacement meter 79, the distance data representing the distance between the distance measuring devices 92a, 92b, 92c, 92d, 92e set in the first opening 51 to the fifth opening 55 in the sample carrier 21 and the lens 19 of the optical head 15 may be instead produced using an optical means such as an auto-focus system, a laser displacement meter or the like and it is unnecessary to form a metal layer such as a chromium layer 91 or the like when the distance data are produced using an optical means.

Further, in the above described embodiments, the temperature in the scanner is set to 15° C., 25° C. or 35° C., the distance data representing distance between the distance measuring devices 92a, 92b, 92c, 92d, 92e set in the first opening 51 to the fifth opening 55 in the sample carrier 21 and the lens 19 of the optical head 15 are produced by the electrostatic capacitance displacement meter 79, and the temperature coefficient K1 of the first sample position to the temperature coefficient K5 of the fifth sample position are calculated based on the distance data representing distance between the distance measuring devices 92a, 92b, 92c, 92d, 92e set in the first opening 51 to the fifth opening 55 in the sample carrier 21 and the lens 19 of the optical head 15. However, the temperature coefficient K1 of the first sample position to the temperature coefficient K5 of the fifth sample position may instead be calculated based on the shape of a micro-array and the linear expansion coefficient of the substrate of the micro-array.

Furthermore, in the above described embodiments, although the focus position of the confocal optical system is determined for each of the first sample position to the fifth sample position corresponding to the first opening 51 to the fifth opening 55 in the sample carrier 21 and the vertical position of the lens 19 of the optical head 15 is adjusted using the lens height position adjusting apparatus 70, it is possible instead to determine the focus position of the confocal optical system for each main scanning line or a predetermined number of main scanning lines and adjust the vertical position of the lens 19 of the optical head 15 using the lens height position adjusting apparatus 70.

Moreover, although the distance data are measured for nine measurement points on each of the distance measuring devices 92a, 92b, 92c, 92d, 92e in the above described embodiments, the number of points whose distance data are to be measured is not limited to nine but the number and the positions of the measurement points may be arbitrarily determined.

Further, although the shading correction data are produced and stored in the shading correction data storing section 102 in advance in the above described embodiments, it is not absolutely necessary to produce the shading correction data and store them in the shading correction data storing section 102 in advance.

Furthermore, although the data processing section 101 is constituted so as to produce the shading correction data in the above described embodiments, the control unit 80 may be instead constituted so as to produce the shading correction data.

Moreover, in the embodiment shown in FIGS. 1 to 13 and the embodiment shown in FIGS. 14 and 15, the control unit 80 produces shading correction data based on the coefficient of the nth order function for each wavelength of the laser beam 4 produced by fitting with an nth order function the curves A, B and C obtained by plotting the integrated values of signal intensity of digital data and stored in the EPROM 82, the measurement point displacement data V1 of the first sample position to the measurement point displacement data V5 of the fifth sample position stored in the EPROM 82 and the average value T0 of the temperature in the scanner when the coefficient of the nth order function for each wavelength of the laser beam 4 was obtained, and stores the shading correction data in the shading correction data storing section 102 of the data processing apparatus 35. However, the data processing section 101 of the data processing apparatus 35 may be instead constituted so as to produce shading correction data based on the coefficient of the nth order function for each wavelength of the laser beam 4 stored in the EPROM 82, the measurement point displacement data V1 of the first sample position to the measurement point displacement data V5 of the fifth sample position stored in the EPROM 82 and the average value T0 of the temperature in the scanner when the coefficient of the nth order function for each wavelength of the laser beam 4 was obtained and store the shading correction data in the shading correction data storing section 102 of the data processing apparatus 35.

Further, the coefficient of the nth order function for each wavelength of the laser beam 4 is calculated by fitting the curves A, B and C obtained by plotting the integrated values of signal intensity of digital data with an nth order function in the embodiment shown in FIGS. 1 to 13 and the embodiment shown in FIGS. 14 and 15. However, instead of the nth order function, other functions such as a Gaussian function, a Lorenz function or the like and a parameter thereof may be employed and the coefficient of the nth order function for each wavelength of the laser beam 4 may be calculated by storing the measurement point data and effecting interpolation thereon with a straight line or an nth order function instead of the fitting.

Furthermore, although the data processing section 101 of the data processing apparatus 35 produces shading correction data and stores them in the shading correction data storing section 102 of the data processing apparatus 35 in the embodiment shown in FIGS. 16 and 17, the control unit 80 may be instead constituted so as to produce the shading correction data and store them in the shading correction data storing section 102 of the data processing apparatus 35.

Moreover, although the shading correction data are stored in the shading correction data storing section 102 of the data processing apparatus 35 in the above described embodiments, the shading correction data may instead be stored in the EPROM 82.

Further, in the above described embodiments, the shading of the digital data of a fluorescent dye(s) contained in the micro-array are corrected in each of the cases where the temperature in the scanner is set to 15° C., 25° C. or 35° C. by producing shading data, storing them in the shading correction data storing section 102, and producing shading correction data corresponding to the temperature in the scanner detected by the temperature sensor 84 based on the shading data at 15° C., 25° C. or 35° C. stored in the shading correction data storing section 102. Instead, however, it is possible to produce shading correction data for each temperature in the scanner in advance based on the shading data at 15° C., 25° C. or 35° C. and store them in the shading correction data storing section 102 and it is also possible to store only the shading correction data at 25° C., for example, in the shading correction data storing section 102 and correct the shading of the digital data of a fluorescent dye(s) contained in the micro-array using the shading correction data at 25° C. irrespective of the temperature in the scanner.

Furthermore, in the above described embodiments, the distance data representing distance between distance measuring devices 92a, 92b, 92c, 92d, 92e set in the first opening 51 to the fifth opening 55 in the sample carrier 21 and the lens 19 of the optical head 15 are produced in the cases where the temperatures in the scanner are set to 15° C., 25° C. or 35° C. However, the temperature at which the distance data representing distance between distance measuring devices 92a, 92b, 92c, 92d, 92e set in the first opening 51 to the fifth opening 55 in the sample carrier 21 and the lens 19 of the optical head 15 are produced can be arbitrarily determined.

Moreover, in the above described embodiments, the temperature coefficient K1 of the first sample position to the temperature coefficient K5 of the fifth sample position are calculated based on the distance data representing distance between distance measuring devices 92a, 92b, 92c, 92d, 92e set in the first opening 51 to the fifth opening 55 in the sample carrier 21 and the lens 19 of the optical head 15 at 15° C., 25° C. or 35° C. and the focus position data of the confocal optical system are corrected in accordance with the temperature in the scanner. However, it is possible instead to measure the distance data only at 25° C., for example, to determine the focus position of the confocal optical system, thereby omitting the correction operation of the focus position data of the confocal optical system using the temperature in the scanner.

Further, although each of the distance measuring devices 92a, 92b, 92c, 92d, 92e is constituted as the slide glass plate 90 having the chromium layer 91 formed by sputtering on the whole surface thereof in the above described embodiments, it is unnecessary to form the chromium layer 91 on the whole surface of the slide glass plate 90 and it is sufficient to form the chromium layer 91 at least at measurement points on the distance measuring devices 92a, 92b, 92c, 92d, 92e.

Furthermore, although each of the distance measuring devices 92a, 92b, 92c, 92d, 92e is constituted as the slide glass plate 90 having the chromium layer 91 formed by sputtering on the whole surface thereof in the above described embodiments, instead of the chromium layer 91, a metal layer formed of a material selected from a group consisting of aluminum, gold, nickel-chromium alloy and titanium-nickel-chromium alloy may be formed.

Moreover, in embodiment shown in FIGS. 14 and 15, the focus position determination device 110 includes a support 111 constituted as a color glass filter formed by doping glass containing material selected from a group consisting of silica sand, soda ash and limestone as a principal component with a solid solution of CdS—CdSe. However, instead of the color glass filter formed by doping with a solid solution of CdS—CdSe, a color glass filter formed by doping glass containing material selected from a group consisting of silica sand, soda ash and limestone as a principal component with a solid solution of ZnS—CdS may be employed. Further, similarly to the shading estimation device 120 shown in FIGS. 16 and 17, the support 111 of the focus position determination device 110 may be a laminate 123 formed by laminating an InGaAsP layer 121 and a GaAs layer 122 and it is sufficient for the support 111 of the focus position determination device 110 to be formed of a material selected from a group consisting of IV group elements, II–VI group compounds, III–V group compounds and complexes thereof.

Furthermore, the shading estimation device 120 includes a laminate 123 formed by laminating an InGaAsP layer 121 and a GaAs layer 122 in the embodiment shown in FIGS. 16 and 17. However, instead of the laminate 123 formed by laminating an InGaAsP layer 121 and a GaAs layer 122, similarly to the support 111 of the focus position determination device 110 in the embodiment shown in FIGS. 14 and 15, a color glass filter may be employed as the shading estimation device 120 and the shading estimation device 120 may be formed of a material selected from a group consisting of a solid solution of CdS—CdSe and a solid solution of ZnS—CdS or a material selected from a group consisting of IV group elements, II–VI group compounds, III–V group compounds and complexes thereof.

Moreover, although the spot 97 containing Fluor-X (registered trademark), Cy3 (registered trademark) and Cy5 (registered trademark) is formed on the slide glass plate 96 of the focus position determination device 95 in the embodiment shown in FIG. 11, it is sufficient for the spot 97 to contain a fluorescent dye capable of being effectively stimulated by a laser beam 4 having a wavelength of 473 nm, a fluorescent dye capable of being effectively stimulated by a laser beam 4 having a wavelength of 532 nm and a fluorescent dye capable of being effectively stimulated by a laser beam 4 having a wavelength of 640 nm and it is not absolutely necessary for the spot 97 to contain Fluor-X, Cy3 and Cy5.

Further, the slide glass plate 96 formed with the spot 97 containing Fluor-X (registered trademark), Cy3 (registered trademark) and Cy5 (registered trademark) on the surface thereof is used as the focus position determination device 95 in the embodiment shown in FIG. 11 and the focus position determination device 110 includes the support 111 formed of a color glass filter in the embodiment shown in FIGS. 14 and 15 and both focus position determination device 95, 110 are constituted so as to be stimulated and release fluorescence emission upon being irradiated with a laser beam 4. However, the focus position determination device (95, 110) may be instead constituted so as to be stimulated and release photoluminescence emission upon being irradiated with a laser beam 4.

Furthermore, in the embodiment shown in FIGS. 16 and 17, the shading estimation device 120 includes the laminate 123 formed by laminating an InGaAsP layer 121 and a GaAs layer 122 and is constituted so as to be stimulated and release fluorescence emission upon being irradiated with a laser beam 4. However, the shading estimation device 120 may be constituted so as to be stimulated and release photoluminescence emission upon being irradiated with a laser beam 4.

Moreover, in the above described embodiments, although the sample carrier 21 is formed with five openings 51, 52, 53, 54, 55 so as to carry five micro-arrays, the number of micro-arrays to be carried in the sample carrier 21 may be arbitrarily determined and is not limited to five.

Further, in the above described embodiments, although the lens 19 of the optical head 15 is moved using the stepping motor 76, the lens 19 of the optical head 15 may be moved using other driving means.

Furthermore, in the above described embodiments, the scanner is constituted so as to produce image data for biochemical analysis by scanning a micro-array including a slide glass plate on which a number of spots of a specimen selectively labeled with a fluorescent dye are formed as a substrate with a laser beam 4 to stimulate the fluorescent dye and photoelectrically detecting fluorescence emission released from the fluorescent dye, further to produce image data for biochemical analysis by scanning a fluorescence sample including a transfer support containing denatured DNA fragments selectively labeled with a fluorescent dye as a substrate with a laser beam 4 to stimulate the fluorescent dye and photoelectrically detecting fluorescence emission released from the fluorescent dye, and further to produce image data for biochemical analysis by scanning a stimulable phosphor layer of a stimulable phosphor sheet in which locational information of a radioactive labeling substance are recorded by closely contacting a substrate such as a membrane filter having a number of spots of a specimen selectively labeled with a radioactive labeling substance and the stimulable phosphor sheet formed with the stimulable phosphor layer containing a stimulable phosphor to expose the stimulable phosphor layer with the radioactive labeling substance with a laser beam 4 to excite the stimulable phosphor and photoelectrically detecting stimulated emission released from the stimulable phosphor. However, it is sufficient for the scanner to be able to produce image data for biochemical analysis by scanning a micro-array including a slide glass plate on which a number of spots of a specimen selectively labeled with a fluorescent dye are formed as a substrate with a laser beam 4 to stimulate the fluorescent dye and photoelectrically detecting fluorescence emission released from the fluorescent dye and it is not absolutely necessary for the scanner to be further constituted so as to produce image data for biochemical analysis by scanning a fluorescence sample including a transfer support containing denatured DNA fragments selectively labeled with a fluorescent dye as a substrate with a laser beam 4 to stimulate the fluorescent dye and photoelectrically detecting fluorescence emission released from the fluorescent dye, and to produce image data for biochemical analysis by scanning a stimulable phosphor layer of a stimulable phosphor sheet in which locational information of a radioactive labeling substance are recorded by closely contacting a substrate such as a membrane filter having a number of spots of a specimen selectively labeled with a radioactive labeling substance and the stimulable phosphor sheet formed with the stimulable phosphor layer containing a stimulable phosphor to expose the stimulable phosphor layer with the radioactive labeling substance with a laser beam 4 to excite the stimulable phosphor and photoelectrically detecting stimulated emission released from the stimulable phosphor.

Moreover, in the above described embodiments, although the scanner includes the first laser stimulating ray source 1, the second laser stimulating ray source 2 and the third laser stimulating ray source 3, it is not absolutely necessary for the scanner to include three laser stimulating ray sources.

Further, in the above described embodiments, although a semiconductor laser beam source for emitting a laser beam 4 having a wavelength of 640 nm is employed as the first laser stimulating ray source 1, a He—Ne laser beam source for emitting a laser beam 4 having a wavelength of 633 nm or a semiconductor laser beam source for emitting a laser beam 4 having a wavelength of 635 nm may be employed instead of the semiconductor laser beam source for emitting a laser beam 4 having a wavelength of 640 nm and a laser beam source for emitting a laser beam 4 having a wavelength of 630 to 650 nm may be used as the first laser stimulating ray source 1.

Moreover, in the above described embodiment, a laser beam source for emitting a laser beam 4 having a wavelength of 532 nm is used as the second laser stimulating ray source 2 and a laser beam source for emitting a laser beam 4 having a wavelength of 473 nm is used as the third laser stimulating ray source 3. However, depending upon the kind of a fluorescent substance, a laser beam source for emitting a laser beam 4 having a wavelength of 530 to 540 nm may be used as the second laser stimulating ray source 2 and a laser beam source for emitting a laser beam 4 having a wavelength of 470 to 480 nm may be used as the third laser stimulating ray source 3.

Furthermore, in the above described embodiments, the scanner includes the first laser stimulating ray source 1 for emitting a laser beam 4 having a wavelength of 640 nm, the second laser stimulating ray source 2 for emitting a laser beam 4 having a wavelength of 532 nm and the third laser stimulating ray source 3 for emitting a laser beam 4 having a wavelength of 473 nm and the focus position of the confocal optical system is determined for each case where the first laser stimulating ray source 1 for emitting a laser beam 4 having a wavelength of 640 nm, the second laser stimulating ray source 2 for emitting a laser beam 4 having a wavelength of 532 nm or the third laser stimulating ray source 3 for emitting a laser beam 4 having a wavelength of 473 nm is used and the focus position data are stored in the EPROM 82. However, the wavelength of a laser beam 4 may be arbitrarily selected and it is sufficient to determine the focus position of the confocal optical system in accordance with the wavelength of a laser beam 4 to be used, store the focus position data in the EPROM 82 and adjust the position of the lens 19 of the optical head 15 using the focus position data and it is not absolutely necessary to determine the focus position of the confocal optical system for each case where the first laser stimulating ray source 1 for emitting a laser beam 4 having a wavelength of 640 nm, the second laser stimulating ray source 2 for emitting a laser beam 4 having a wavelength of 532 nm or the third laser stimulating ray source 3 for emitting a laser beam 4 having a wavelength of 473 nm is used and store the focus position data in the EPROM 82.

In addition, in the above described embodiments, the confocal switching member 31 is formed with three pinholes 32a, 32b, 32c having different diameters so that when biochemical analysis data are to be produced by scanning the micro-array 22 in which a plurality of spots of a specimen selectively labeled with a fluorescent dye are formed on the slide glass plate 23 to stimulate the fluorescent dye and photoelectrically detecting fluorescence emission released from the fluorescent dye, the pinhole 32a is used, when biochemical analysis data are to be produced by scanning the stimulable phosphor layer of the stimulable phosphor sheet in which locational information of a radioactive labeling substance obtained by exposing the stimulable phosphor layer to radiation is recorded with a laser beam 4 to stimulate a stimulable phosphor and photoelectrically detecting stimulated emission released from the stimulable phosphor, the pinhole 32b is used, and when biochemical analysis data are to be produced by scanning the fluorescence sample including a transfer support with a laser beam 4 to stimulate the fluorescent dye and photoelectrically detecting fluorescence emission released from the fluorescent dye, the pinhole 32c is used. However, it is possible to form only the pinholes 32a, 32b in the confocal switching member 31 so that when biochemical analysis data are to be produced by scanning the micro-array 22 in which a plurality of spots of a specimen selectively labeled with a fluorescent dye are formed on the slide glass plate 23 to stimulate the fluorescent dye and photoelectrically detecting fluorescence emission 25 released from the fluorescent dye, fluorescence emission 25 is detected through the pinhole 32a, when biochemical analysis data are to be produced by photoelectrically detecting stimulated emission 25 released from the stimulable phosphor layer, the stimulated emission 25 is detected through the pinhole 32b, and when biochemical analysis data are to be produced by photoelectrically detecting fluorescence emission 25 released from the fluorescence sample including the transfer support as a substrate, the confocal switching member 31 is retracted from the optical path of fluorescence emission 25, thereby increasing the light amount received by the photomultiplier 33, and it is also possible to form only the pinhole 32a in the confocal switching member 31 so that only when biochemical analysis data are to be produced by scanning the micro-array 22 in which a plurality of spots of a specimen selectively labeled with a fluorescent dye are formed on the slide glass plate 23 to stimulate the fluorescent dye and photoelectrically detecting fluorescence emission 25 released from the fluorescent dye, fluorescence emission 25 is detected through the pinhole 32a and when biochemical analysis data are to be produced by photoelectrically detecting stimulated emission 25 released from the stimulable phosphor layer and when biochemical analysis data are to be produced by photoelectrically detecting fluorescence emission 25 released from the fluorescence sample including the transfer support as a substrate, the confocal switching member 31 is retracted from the optical path of fluorescence emission 25, thereby increasing the light amount received by the photomultiplier 33.

Further, in the above described embodiments, the adjustment of the focus of the confocal optical system in the case where the sample 22 is a fluorescence sample including a transfer support as a substrate and in the case where a stimulable phosphor sheet is conducted similarly to the case where the sample 22 is a micro-array. However, since the focus of the confocal optical system does not need to be adjusted as accurately for a fluorescence sample including a transfer support as a substrate and a stimulable phosphor sheet as for a micro-array, it is possible instead to set the number of drive pulses P to be $P_{532}$ without effecting temperature correction and displacement correction in accordance with the positions of the fluorescence sample and the stimulable phosphor sheet, output a drive signal to the stepping motor 76, thereby causing it to move the lens 19 of the optical head 15 to a predetermined position, and hold it at the position.

According to the present invention, it is possible to provide a scanner having a confocal optical system, a method for producing focus position data of a confocal optical system of a scanner having a confocal optical system and a method for producing digital data of a scanner having a confocal optical system, which can adjust the focus of a confocal optical system with high accuracy without need for special devices and produce digital data for biochemical analysis in a desired manner.

What is claimed is:

1. A scanner comprising at least one laser stimulating ray source for emitting a laser beam, a sample stage on which a sample carrier for carrying at least one sample is to be placed, a scanning means for moving the sample stage in a main scanning direction and in a sub-scanning direction, a confocal optical system, a drive means for an objective lens incorporated in the confocal optical system, a light detector for photoelectrically detecting light, a non-volatile memory, and a control means, the non-volatile memory being constituted so as to store position data produced by setting at least one distance measuring device in the sample carrier for carrying at least one sample, placing the sample carrier on the sample stage, and measuring a distance between the objective lens incorporated in the confocal optical system and a reference position on a surface of the at least one distance measuring device set in the sample carrier and a distance between the objective lens and at least one of the measurement positions on a surface of the at least one distance measuring device different from the reference position, and to store focus position data produced by setting a focus position determination device including a luminescent material having a property to release fluorescence emission or photoluminescence emission upon being irradiated with the laser beam in the sample carrier so that the luminescent material is located at the reference position, scanning the focus position determination device with the laser beam to stimulate the luminescent material located at the reference position, photoelectrically detecting fluorescence emission or photoluminescence emission released from the luminescent material by the light detector, changing the position of the objective lens of the confocal optical system with a predetermined pitch, and determining a focus position of the confocal optical system, the control means being constituted so as to correct the focus position data of the confocal optical system stored in the non-volatile memory with the position data stored in the non-volatile memory, and output a drive signal to the drive means based on the thus corrected focus position data of the confocal optical system, thereby causing it to move the objective lens of the confocal optical system and adjust the position of the objective lens.

2. A scanner in accordance with claim 1 wherein the position of the objective lens of the confocal optical system at which an integrated value of signal intensity of fluorescence emission or photoluminescence emission detected by the light detector becomes maximum is determined as the focus position of the confocal optical system and is stored in the non-volatile memory as the focus position data.

3. A scanner in accordance with claim 1 wherein the position data are produced by measuring the distance between the objective lens incorporated in the confocal optical system and the reference position on the surface of the at least one distance measuring device set in the sample carrier and the distance between the objective lens and the at least one measurement position on the surface of the at least one distance measuring device different from the reference position and calculating a displacement of the at least one measurement position on the surface of the at least one distance measuring device set in the sample carrier different from the reference position with respect to the reference position on the surface of the at least one distance measuring device and are stored in the non-volatile memory.

4. A scanner in accordance with claim 1 wherein the position data are produced by measuring the distance between the objective lens incorporated in the confocal optical system and the reference position on the surface of the at least one distance measuring device set in the sample carrier and the distance between the objective lens and two or more measurement positions different from the reference position on the surface of the at least one distance measuring device, calculating displacements of the two or more measurement positions different from the reference position on the surface of the at least one distance measuring device set in the sample carrier with respect to the reference position on the surface of the at least one distance measuring device, and averaging the displacements of the two or more measurement positions different from the reference position on the surface of the at least one distance measuring device with respect to the reference position, and are stored in the non-volatile memory.

5. A scanner in accordance with claim 4 which further comprises a temperature sensor for detecting a temperature in the scanner and wherein the non-volatile memory is constituted so as to store the temperature coefficients of displacements of the two or more measurement positions different from the reference position on the surface of the at least one distance measuring device with respect to the reference position produced by measuring the distance between the objective lens incorporated in the confocal optical system and the reference position on the surface of the at least one distance measuring device set in the sample carrier and the distance between the objective lens and two or more measurement positions different from the reference position on the surface of the at least one distance measuring device at two or more different temperatures from each other, and calculating displacements of the two or more measurement positions different from the reference position on the surface of the at least one distance measuring device set in the sample carrier with respect to the reference position on the surface of the at least one distance measuring device, and to store an average value of temperatures in the scanner detected by the temperature sensor when the focus position data of the confocal optical system were produced, and the control means is constituted so as to correct the focus position data of the confocal optical system stored in the non-volatile memory according to difference in temperature between a temperature in the scanner detected by the temperature sensor and the average value of temperatures in the scanner when the focus position data of the confocal optical system were produced and in accordance with the temperature coefficients of the two or more measurement positions different from the reference position on the surface of each of the two or more distance measuring devices with respect to the reference position stored in the non-volatile memory.

6. A scanner in accordance with claim 4 wherein the sample carrier is constituted so as to carry two or more distance measuring devices, the non-volatile memory is constituted so as to store the position data produced by placing the sample carrier carrying two or more samples on the sample stage, measuring distances between the objective lens incorporated in the confocal optical system and three or more measurement positions different from each other on each of the two or more distance measuring devices, determining one of the measurement positions on one of the two or more distance measuring devices as the reference position, calculating displacements of the measurement positions on each of the two or more distance measuring devices with respect to the reference position, and averaging the displacements of the measurement positions on each of the two or more distance measuring devices, and the control means is constituted so as to correct the focus position data of the confocal optical system stored in the non-volatile memory based on the position data stored in the non-volatile memory for each of samples set at positions corresponding to positions of the two or more distance measuring devices set in the sample carrier, and output a drive signal to the drive means in accordance with the thus corrected focus position data of the confocal optical system, thereby causing it to move the objective lens of the confocal optical system and adjust the position of the objective lens.

7. A scanner in accordance with claim 5 wherein the sample carrier is constituted so as to carry two or more distance measuring devices, the non-volatile memory is constituted so as to store the position data produced by placing the sample carrier carrying two or more samples on the sample stage, measuring distances between the objective lens incorporated in the confocal optical system and three or more measurement positions different from each other on each of the two or more distance measuring devices, determining one of the measurement positions on one of the two or more distance measuring devices as the reference position, calculating displacements of the measurement positions on each of the two or more distance measuring devices with respect to the reference position, and averaging the displacements of the measurement positions on each of the two or more distance measuring devices, and the control means is constituted so as to correct the focus position data of the confocal optical system stored in the non-volatile memory based on the position data stored in the non-volatile memory for each of samples set at positions corresponding to positions of the two or more distance measuring devices set in the sample carrier, and output a drive signal to the drive means in accordance with the thus corrected focus position data of the confocal optical system, thereby causing it to move the objective lens of the confocal optical system and adjust the position of the objective lens.

8. A scanner in accordance with claim 7 wherein the temperature coefficients of displacements of the measurement positions with respect to the reference position are calculated by measuring distances between the objective lens incorporated in the confocal optical system and the three or more measurement positions on each of the two or more distance measuring devices at two or more temperatures different from each other, determining one of the measurement positions on one of the two or more distance measuring devices as the reference position and calculating displacements of the measurement positions on each of the two or more distance measuring devices with respect to the reference position, the non-volatile memory is constituted so as to store an average value of the temperature coefficients of displacements of the measurement positions with respect to the reference position as the temperature coefficient of each of the two or more distance measuring devices and to store an average value of the temperatures in the scanner detected by the temperature sensor when the focus position data were produced, and the control means is constituted so as to correct the focus position data of the confocal optical system stored in the non-volatile memory for each of the two or more distance measuring devices according to difference in temperature between a temperature in the scanner detected by the temperature sensor and the average value of temperatures in the scanner when the focus position data of the confocal optical system were produced and in accordance with the temperature coefficients of the two or more measurement positions different from the reference position on the surface of each of the two or more distance measuring devices with respect to the reference position stored in the non-volatile memory, and output a drive signal to the drive means in accordance with the thus corrected focus position data of the confocal optical system, thereby causing it to move the objective lens of the confocal optical system and adjust the position of the objective lens.

9. A scanner in accordance with claim 7 wherein the non-volatile memory is constituted so as to store the position data produced by measuring distances between the objective lens incorporated in the confocal optical system and at least two measurement positions different from each other in each main scanning line on each of the two or more distance measuring devices set in the sample carrier, determining one of the measurement positions on one of the two or more distance measuring devices as the reference position, calculating displacements of the measurement positions on each of the two or more distance measuring devices with respect to the reference position, and averaging the displacements of the measurement positions on each of the two or more distance measuring devices.

10. A scanner in accordance with claim 8 wherein the non-volatile memory is constituted so as to store the position data produced by measuring distances between the objective lens incorporated in the confocal optical system and at least two measurement positions different from each other in each main scanning line on each of the two or more distance measuring devices set in the sample carrier, determining one of the measurement positions on one of the two or more distance measuring devices as the reference position, calculating displacements of the measurement positions on each of the two or more distance measuring devices with respect to the reference position, and averaging the displacements of the measurement positions on each of the two or more distance measuring devices.

11. A scanner in accordance with claim 10 wherein the temperature coefficients of displacements of the measurement positions with respect to the reference position are calculated by measuring distances between the objective lens incorporated in the confocal optical system and the at least two measurement positions in each main scanning line on each of the two or more distance measuring devices at two or more temperatures different from each other, determining one of the measurement positions on one of the two or more distance measuring devices as the reference position and calculating displacements of the measurement positions on each of the two or more distance measuring devices with respect to the reference position, the non-volatile memory is constituted so as to store an average value of the temperature coefficients of displacements of the measurement positions with respect to the reference position as the temperature coefficient of each of the two or more distance measuring devices and to store an average value of the temperatures in the scanner detected by the temperature sensor when the focus position data were produced, and the control means is constituted so as to correct the focus position data of the confocal optical system stored in the non-volatile memory for each of the two or more distance measuring devices according to difference in temperature between a temperature in the scanner detected by the temperature sensor and the average value of temperatures in the scanner when the focus position data of the confocal optical system were produced and in accordance with the temperature coefficients of the two or more distance measuring devices stored in the non-volatile memory, and output a drive signal to the drive means in accordance with the thus corrected focus position data of the confocal optical system, thereby causing it to move the objective lens of the confocal optical system and adjust the position of the objective lens.

12. A scanner in accordance with claim 9 wherein the non-volatile memory is constituted so as to store the position data produced by measuring distances between the objective lens incorporated in the confocal optical system and three measurement positions different from each other in each main scanning line on each of the two or more distance measuring devices set in the sample carrier, determining one of the measurement positions on one of the two or more distance measuring devices as the reference position, calculating displacements of the measurement positions on each of the two or more distance measuring devices with respect to the reference position, and averaging the displacements of the measurement positions on each of the two or more distance measuring devices.

13. A scanner in accordance with claim 10 wherein the non-volatile memory is constituted so as to store the position data produced by measuring distances between the objective lens incorporated in the confocal optical system and three measurement positions different from each other in each main scanning line on each of the two or more distance measuring devices set in the sample carrier, determining one of the measurement positions on one of the two or more distance measuring devices as the reference position, calculating displacements of the measurement positions on each of the two or more distance measuring devices with respect to the reference position, and averaging the displacements of the measurement positions on each of the two or more distance measuring devices.

14. A scanner in accordance with claim 13 wherein the temperature coefficients of displacements of the measurement positions with respect to the reference position are calculated by measuring distances between the objective lens incorporated in the confocal optical system and the three measurement positions in each main scanning line on each of the two or more distance measuring devices at two or more temperatures different from each other, determining one of the measurement positions on one of the two or more distance measuring devices as the reference position and calculating displacements of the measurement positions on each of the two or more distance measuring devices with respect to the reference position, the non-volatile memory is constituted so as to store an average value of the temperature coefficients of displacements of the measurement positions with respect to the reference position as the temperature coefficient of each of the two or more distance measuring devices and to store an average value of the temperatures in the scanner detected by the temperature sensor when the focus position data were produced, and the control means is constituted so as to correct the focus position data of the confocal optical system stored in the non-volatile memory for each of the two or more distance measuring devices according to difference in temperature between a temperature in the scanner detected by the temperature sensor and the average value of temperatures in the scanner when the focus position data of the confocal optical system were produced and in accordance with the temperature coefficients of the two or more distance measuring devices stored in the non-volatile memory, and output a drive signal to the drive means in accordance with the thus corrected focus position data of the confocal optical system, thereby causing it to move the objective lens of the confocal optical system and adjust the position of the objective lens.

15. A scanner in accordance with claim 6 wherein the non-volatile memory is constituted so as to store the position data produced by averaging the displacements of the measurement positions with respect to the reference position for each predetermined number of main scanning lines on each of the two or more distance measuring devices, and the control means is constituted so as to correct the focus position data of the confocal optical system stored in the non-volatile memory for each number of main scanning lines corresponding to the predetermined number of main scanning lines of the samples set at positions in the sample carrier corresponding to positions where the two or more distance measuring devices were set based on the position data stored in the non-volatile memory, and output a drive signal to the drive means in accordance with the thus corrected focus position data of the confocal optical system, thereby causing it to move the objective lens of the confocal optical system and adjust the position of the objective lens.

16. A scanner in accordance with claim 7 wherein the non-volatile memory is constituted so as to store the position data produced by averaging the displacements of the measurement positions with respect to the reference position for each predetermined number of main scanning lines on each of the two or more distance measuring devices, and the control means is constituted so as to correct the focus position data of the confocal optical system stored in the non-volatile memory for each number of main scanning lines corresponding to the predetermined number of main scanning lines of the samples set at positions in the sample carrier corresponding to positions where the two or more distance measuring devices were set based on the position data stored in the non-volatile memory, and output a drive signal to the drive means in accordance with the thus corrected focus position data of the confocal optical system, thereby causing it to move the objective lens of the confocal optical system and adjust the position of the objective lens.

17. A scanner in accordance with claim 16 wherein the temperature coefficients of displacements of the measurement positions with respect to the reference position are calculated by measuring distances between the objective lens incorporated in the confocal optical system and three measurement positions in each main scanning line for each predetermined number of main scanning lines on each of the two or more distance measuring devices at two or more temperatures different from each other, determining one of the measurement positions on one of the two or more distance measuring devices as the reference position and calculating displacements of the measurement positions for each predetermined number of main scanning lines on each of the two or more distance measuring devices with respect to the reference position, the non-volatile memory is constituted so as to store an average value of the temperature coefficients of displacements of the measurement positions with respect to the reference position for each predetermined number of main scanning lines as the temperature coefficient of each predetermined number of main scanning lines of each of the two or more distance measuring devices and to store an average value of the temperatures in the scanner detected by the temperature sensor when the focus position data were produced, and the control means is constituted so as to correct the focus position data of the confocal optical system stored in the non-volatile memory for each number of main scanning lines corresponding to the predetermined number of main scanning lines of the samples set at positions in the sample carrier corresponding to positions where the two or more distance measuring devices were set according to difference in temperature between a temperature in the scanner detected by the temperature sensor and the average value of temperatures in the scanner when the focus position data of the confocal optical system were produced and in accordance with the temperature coefficients of the predetermined number of main scanning lines on each of the two or more distance measuring devices, and output a drive signal to the drive means in accordance with the thus corrected focus position data of the confocal optical system, thereby causing it to move the objective lens of the confocal optical system and adjust the position of the objective lens.

18. A scanner in accordance with claim 1 which further comprises two or more laser stimulating ray sources for emitting laser beams having different wavelengths from each other and wherein the non-volatile memory is constituted so as to store the focus position data of the confocal optical system produced for each wavelength of the laser beam, and the control means is constituted so as to read from the non-volatile memory the focus position data of the confocal optical system corresponding to the wavelength of the laser beam emitted from the laser stimulating ray source to be used for scanning the at least one sample from among the two or more laser stimulating ray sources, and output a drive signal to the drive means in accordance with the thus read focus position data of the confocal optical system, thereby causing it to move the objective lens of the confocal optical system and adjust the position of the objective lens.

19. A scanner in accordance with claim 1 which further comprises a data processing apparatus and wherein the non-volatile memory is constituted so as to store coefficients of an nth order function produced by plotting integrated values of signal intensity of fluorescence emission or photoluminescence emission detected by the light detector and fitting the plotted values with the nth order function by the control means and displacements of measurement positions on the at least one distance measuring device with respect to the reference position, the control means or the data processing apparatus is constituted so as to produce shading correction data for correcting shading of digital data of the at least one sample based on the coefficients of the nth order function and the displacements of measurement positions on the at least one distance measuring device with respect to the reference position stored in the non-volatile memory, and the data processing apparatus is constituted so as to correct the digital data of the at least one sample based on the shading correction data.

20. A scanner in accordance with claim 1 which further comprises a data processing apparatus, and wherein the non-volatile memory is constituted so as to store shading correction data for correcting shading of digital data of the at least one sample produced based on coefficients of an nth order function produced by plotting integrated values of signal intensity of fluorescence emission or photoluminescence emission detected by the light detector and fitting the plotted values with the nth order function by the control means and displacements of measurement positions on the at least one distance measuring device with respect to the reference position, and the data processing apparatus is constituted so as to correct the digital data of the at least one sample based on the shading correction data.

21. A scanner in accordance with claim 1 which further comprises a data processing apparatus provided with a memory, the data processing apparatus is constituted so as to produce shading correction data based on digital data of a shading estimation device produced by setting the shading estimation device in which a mask of metal is formed on a support having a property to release fluorescence emission upon being irradiated with a laser beam and capable of being processed while retaining optical flatness, thereby regularly forming a plurality of openings through which the support is exposed in the sample carrier, placing the sample carrier on the sample stage, scanning the shading estimation device with the laser beam emitted from the at least one laser stimulating ray source via the openings to stimulate the support at the plurality of openings, photoelectrically detecting fluorescence emission released from the support via the plurality of openings by the light detector to produce analog data, digitizing the analog data, to store the shading correction data of the shading estimation device in the non-volatile memory or the memory of the data processing apparatus, and to correct digital data of the at least one sample based on the shading correction data stored in the non-volatile memory or the memory of the data processing apparatus.

22. A scanner in accordance with claim 21 wherein the shading correction data are produced by integrating signal intensity of digital signals obtained by the photoelectrically detecting fluorescence emission released from the support every opening.

23. A scanner in accordance with claim 21 wherein the digital data of the shading estimation device are produced by scanning the shading estimation device with the laser beam via the plurality of openings after a focus of the confocal optical system is adjusted to the opening located at the reference position among the plurality of openings regularly formed in the shading estimation device, photoelectrically detecting fluorescence emission released from the support to produce analog data and digitizing the analog data.

24. A method for producing focus position data of a confocal optical system of a scanner having a confocal optical system comprising steps of setting at least one distance measuring device in a sample carrier for carrying at least one sample, placing the sample carrier on the sample stage, measuring a distance between an objective lens incorporated in the confocal optical system and a reference position on a surface of the at least one distance measuring device set in the sample carrier and a distance between the objective lens and at least one measurement position on a surface of the at least one distance measuring device different from the reference position, thereby producing position data, storing them in a non-volatile memory, setting a focus position determination device including a luminescent material having a property to release fluorescence emission or photoluminescence emission upon being irradiated with the laser beam in the sample carrier so that the luminescent material is located at the reference position, scanning the focus position determination device with the laser beam to stimulate the luminescent material located at the reference position, photoelectrically detecting fluorescence emission or photoluminescence emission released from the luminescent material, changing the position of the objective lens of the confocal optical system with a predetermined pitch, determining a focus position of the confocal optical system, thereby producing the position data, and storing them in the non-volatile memory.

25. A method for producing focus position data of a confocal optical system of a scanner having a confocal optical system in accordance with claim 24 wherein the position of the objective lens of the confocal optical system at which an integrated value of signal intensity of fluorescence emission or photoluminescence emission detected by the light detector becomes maximum is determined as the focus position of the confocal optical system.

26. A method for producing focus position data of a confocal optical system of a scanner having a confocal optical system in accordance with claim 24 which comprises steps of measuring the distance between the objective lens incorporated in the confocal optical system and the reference position on the surface of the at least one distance measuring device set in the sample carrier and the distance between the objective lens and the at least one measurement position on the surface of the at least one distance measuring device different from the reference position and calculating a displacement of the at least one measurement position on the surface of the at least one distance measuring device set in the sample carrier different from the reference position with respect to the reference position on the surface of the at least one distance measuring device, thereby producing the position data.

27. A method for producing focus position data of a confocal optical system of a scanner having a confocal optical system in accordance with claim 24 which comprises steps of measuring the distance between the objective lens incorporated in the confocal optical system and the reference position on the surface of the at least one distance measuring device set in the sample carrier and the distance between the objective lens and two or more measurement positions different from the reference position on the surface of the at least one distance measuring device, calculating displacements of the two or more measurement positions different from the reference position on the surface of the at least one distance measuring device set in the sample carrier with respect to the reference position on the surface of the at least one distance measuring device, and averaging the displacements of the two or more measurement positions different from the reference position on the surface of the at least one distance measuring device with respect to the reference position, thereby producing the position data.

28. A method for producing focus position data of a confocal optical system of a scanner having a confocal optical system in accordance with claim 27 which comprises steps of measuring the distance between the objective lens incorporated in the confocal optical system and the reference position on the surface of the at least one distance measuring device set in the sample carrier and the distance between the objective lens and two or more measurement positions different from the reference position on the surface of the at least one distance measuring device at two or more different temperatures from each other, calculating displacements of the two or more measurement positions different from the reference position on the surface of the at least one distance measuring device set in the sample carrier with respect to the reference position on the surface of the at least one distance measuring device, and storing temperature coefficients of the displacements of the two or more measurement positions different from the reference position on the surface of the at least one distance measuring device with respect to the reference position and an average temperature in the scanner when the focus position data were produced in the non-volatile memory.

29. A method for producing focus position data of a confocal optical system of a scanner having a confocal optical system in accordance with claim 27 wherein the sample carrier is constituted so as to carry two or more distance measuring devices, and which comprises steps of placing the sample carrier carrying two or more samples on the sample stage, measuring distances between the objective lens incorporated in the confocal optical system and three or more measurement positions different from each other on each of the two or more distance measuring devices, determining one of the measurement positions on one of the two or more distance measuring devices as the reference position, calculating displacements of the measurement positions on each of the two or more distance measuring devices with respect to the reference position, averaging the displacements of the measurement positions on each of the two or more distance measuring devices to produce the position data, and storing them in the non-volatile memory.

30. A method for producing focus position data of a confocal optical system of a scanner having a confocal optical system in accordance with claim 29 which the method for producing focus position data of a confocal optical system of a scanner comprises steps of measuring distances between the objective lens incorporated in the confocal optical system and the three or more measurement positions on each of the two or more distance measuring devices with respect to the reference position determined by one of measurement positions on one of the two or more distance measuring device at two or more temperatures different from each other, calculating displacements of the measurement positions on each of the two or more distance measuring devices with respect to the reference position to calculate the temperature coefficients of displacements of the measurement positions with respect to the reference position, and storing the thus calculated temperature coefficients and an average temperature in the scanner when the focus position data were produced in the non-volatile memory.

31. A method for producing focus position data of a confocal optical system of a scanner having a confocal optical system in accordance with claim 29 which comprises steps of measuring distances between the objective lens incorporated in the confocal optical system and at least two measurement positions different from each other in each main scanning line on each of the two or more distance measuring devices set in the sample carrier, determining one of the measurement positions on one of the two or more distance measuring devices as the reference position, calculating displacements of the measurement positions on each of the two or more distance measuring devices with respect to the reference position, averaging the displacements of the measurement positions on each of the two or more distance measuring devices to produce the position data, and storing the thus produced position data in the non-volatile memory.

32. A method for producing focus position data of a confocal optical system of a scanner having a confocal optical system in accordance with claim 30 which comprises steps of measuring distances between the objective lens incorporated in the confocal optical system and at least two measurement positions different from each other in each main scanning line on each of the two or more distance measuring devices set in the sample carrier, determining one of the measurement positions on one of the two or more distance measuring devices as the reference position, calculating displacements of the measurement positions on each of the two or more distance measuring devices with respect to the reference position, averaging the displacements of the measurement positions on each of the two or more distance measuring devices to produce the position data, and storing the thus produced position data in the non-volatile memory.

33. A method for producing focus position data of a confocal optical system of a scanner having a confocal optical system in accordance with claim 32 which comprises steps of measuring distances between the objective lens incorporated in the confocal optical system and the at least two measurement positions in each main scanning line on each of the two or more distance measuring devices at two or more temperatures different from each other, determining one of the measurement positions on one of the two or more distance measuring devices as the reference position, calculating displacements of the measurement positions on each of the two or more distance measuring devices with respect to the reference position to produce the temperature coefficients of displacements of the measurement positions with respect to the reference position, and storing an average value of the temperature coefficients of displacements of the measurement positions with respect to the reference position and an average temperature in the scanner when the focus position data were produced.

34. A method for producing focus position data of a confocal optical system of a scanner having a confocal optical system in accordance with claim 31 which comprises steps of measuring distances between the objective lens incorporated in the confocal optical system and three measurement positions different from each other in each main scanning line on each of the two or more distance measuring devices set in the sample carrier, determining one of the measurement positions on one of the two or more distance measuring devices as the reference position, calculating displacements of the measurement positions on each of the two or more distance measuring devices with respect to the reference position, averaging the displacements of the measurement positions on each of the two or more distance measuring devices to produce the position data, and storing the thus produced position data in the non-volatile memory.

35. A method for producing focus position data of a confocal optical system of a scanner having a confocal optical system in accordance with claim 32 which comprises steps of measuring distances between the objective lens incorporated in the confocal optical system and three measurement positions different from each other in each main scanning line on each of the two or more distance measuring devices set in the sample carrier, determining one of the measurement positions on one of the two or more distance measuring devices as the reference position, calculating displacements of the measurement positions on each of the two or more distance measuring devices with respect to the reference position, averaging the displacements of the measurement positions on each of the two or more distance measuring devices to produce the position data, and storing the thus produced position data in the non-volatile memory.

36. A method for producing focus position data of a confocal optical system of a scanner having a confocal optical system in accordance with claim 35 which comprises steps of measuring distances between the objective lens incorporated in the confocal optical system and the three measurement positions in each main scanning line on each of the two or more distance measuring devices at two or more temperatures different from each other, determining one of the measurement positions on one of the two or more distance measuring devices as the reference position, calculating displacements of the measurement positions on each of the two or more distance measuring devices with respect to the reference position to produce the temperature coefficients of displacements of the measurement positions with respect to the reference position, and storing an average value of the temperature coefficients of displacements of the measurement positions with respect to the reference position as a temperature coefficient and an average temperature in the scanner when the focus position data were produced in the non-volatile memory.

37. A method for producing focus position data of a confocal optical system of a scanner having a confocal optical system in accordance with claim 36 which comprises steps of averaging displacements of the measurement positions with respect to the reference position for every predetermined number of the main scanning lines on each of the two or more distance measuring devices to produce the position data and storing the thus produced position data.

38. A method for producing focus position data of a confocal optical system of a scanner having a confocal optical system in accordance with claim 37 which the method for producing focus position data of a confocal optical system of a scanner comprises steps of measuring distances between the objective lens incorporated in the confocal optical system and three measurement positions in each main scanning line for each predetermined number of main scanning lines on each of the two or more distance measuring devices at two or more temperatures different from each other, determining one of the measurement positions on one of the two or more distance measuring devices as the reference position to produce the temperature coefficients of displacements of the measurement positions with respect to the reference position, and storing an average value of the temperature coefficients of displacements of the measurement positions with respect to the reference position every predetermined number of the main scanning lines on each of the two or more distance measuring devices as a temperature coefficient and an average temperature in the scanner when the focus position data were produced in the non-volatile memory.

39. A method for producing focus position data of a confocal optical system of a scanner having a confocal optical system in accordance with claim 24 wherein the focus position data of the confocal optical system are produced for each wavelength of a laser beam and stored in the non-volatile memory.

40. A method for producing focus position data of a confocal optical system of a scanner having a confocal optical system in accordance with claim 24 which further comprises steps of plotting integrated values of signal intensity of fluorescence emission or photoluminescence emission, fitting the plotted values with the nth order function to produce coefficients of the nth order function and storing the coefficients of the nth order function in the non-volatile memory as well as displacements of measurement positions on the at least one distance measuring device with respect to the reference position.

41. A method for producing focus position data of a confocal optical system of a scanner having a confocal optical system in accordance with claim 24 which further comprises steps of plotting integrated values of signal intensity of detected fluorescence emission or photoluminescence emission, fitting the plotted values with the nth order function to produce coefficients of the nth order function, producing shading correction data for correcting shading of digital data of the at least one sample based on the coefficients of the nth order function and the displacements of measurement positions on the at least one distance measuring device with respect to the reference position and storing the thus produced shading correction data in the non-volatile memory.

42. A method for producing focus position data of a confocal optical system of a scanner having a confocal optical system in accordance with claim 24 which further comprises steps of setting a shading estimation device in which a mask of metal is formed on a support having a property to release fluorescence emission upon being irradiated with a laser beam and capable of being processed while retaining optical flatness, thereby regularly forming a plurality of openings through which the support is exposed in the sample carrier, placing the sample carrier on the sample stage, scanning the shading estimation device with the laser beam via the openings to stimulate the support at the plurality of openings, photoelectrically detecting fluorescence emission released from the support via the plurality of openings to produce analog data, digitizing the analog data, producing digital data of the shading estimation device based on the thus produced digital data, producing shading correction data based on the digital data of the shading estimation device, and storing the thus produced shading correction data in the non-volatile memory or the memory of the scanner.

43. A method for producing focus position data of a confocal optical system of a scanner having a confocal optical system in accordance with claim 24 wherein digital data of the shading estimation device are produced by integrating signal intensity of digital signals obtained by the photoelectrically detecting fluorescence emission released from the support through every opening.

44. A method for producing focus position data of a confocal optical system of a scanner having a confocal optical system in accordance with claim 42 which further comprises steps of adjusting a focus of the confocal optical system to the opening located at the reference position among the plurality of openings regularly formed in the shading estimation device, scanning the shading estimation device with the laser beam via the plurality of openings, stimulating the support via the plurality of openings, photoelectrically detecting fluorescence emission released from the support to produce analog data, digitizing the analog data to produce digital data of the shading estimation device.

45. A method for producing focus position data of a confocal optical system of a scanner having a confocal optical system in accordance with claim 42 wherein the shading correction data are produced for each wavelength of the laser beam and stored in the non-volatile memory or the memory of the scanner.

46. A method for producing digital data of a scanner having a confocal optical system comprising steps of reading position data produced by setting at least one distance measuring device in the sample carrier for carrying at least one sample, placing the sample carrier on the sample stage, and measuring a distance between the objective lens incorporated in the confocal optical system and a reference position on a surface of the at least one distance measuring device set in the sample carrier and a distance between the objective lens and at least one measurement position on a surface of the at least one distance measuring device different from the reference position thereby producing position data and stored in a non-volatile memory of a scanner from the non-volatile memory, reading focus position data produced by setting a focus position determination device including a luminescent material having a property to release fluorescence emission or photoluminescence emission upon being irradiated with the laser beam in the sample carrier so that the luminescent material is located at the reference position, scanning the focus position determination device with the laser beam to stimulate the luminescent material located at the reference position, photoelectrically detecting fluorescence emission or photoluminescence emission released from the luminescent material, changing the position of the objective lens of the confocal optical system with a predetermined pitch, and determining a focus position of the confocal optical system and stored in the non-volatile memory, correcting the focus position data of the confocal optical system in accordance with the position data, and adjusting the position of the objective lens of the confocal optical system based on the thus corrected focus position data of the confocal optical system.

47. A method for producing digital data of a scanner having a confocal optical system in accordance with claim 46 wherein the position data are produced by measuring the distance between the objective lens incorporated in the confocal optical system and the reference position on the surface of the at least one distance measuring device set in the sample carrier and the distance between the objective lens and the at least one measurement position on the surface of the at least one distance measuring device different from the reference position and calculating a displacement of the at least one measurement position on the surface of the at least one distance measuring device set in the sample carrier different from the reference position with respect to the reference position on the surface of the at least one distance measuring device, and are stored in the non-volatile memory.

48. A method for producing digital data of a scanner having a confocal optical system in accordance with claim 46 wherein the position data are produced by measuring the distance between the objective lens incorporated in the confocal optical system and the reference position on the surface of the at least one distance measuring device set in the sample carrier and the distance between the objective lens and two or more measurement positions different from the reference position on the surface of the at least one distance measuring device, calculating displacements of the two or more measurement positions different from the reference position on the surface of the at least one distance measuring device set in the sample carrier with respect to the reference position on the surface of the at least one distance measuring device, and averaging the displacements of the two or more measurement positions different from the reference position on the surface of the at least one distance measuring device with respect to the reference position, and are stored in the non-volatile memory.

49. A method for producing digital data of a scanner having a confocal optical system in accordance with claim 46 which further comprises steps of reading from the non-volatile memory temperature coefficients of the displacements of the two or more measurement positions different from the reference position on the surface of the at least one distance measuring device with respect to the reference position produced by measuring the distance between the objective lens incorporated in the confocal optical system and the reference position on the surface of the at least one distance measuring device set in the sample carrier and the distance between the objective lens and two or more measurement positions different from the reference position on the surface of the at least one distance measuring device at two or more different temperatures from each other, and calculating displacements of the two or more measurement positions different from the reference position on the surface of the at least one distance measuring device set in the sample carrier with respect to the reference position on the surface of the at least one distance measuring device and stored in the non-volatile memory, reading from the non-volatile memory an average temperature in the scanner when the focus position data were produced stored in the non-volatile memory, correcting the focus position data of the confocal optical system according to difference in temperature between the temperature in the scanner and the average temperature in the scanner when the focus position data of the confocal optical system were produced and in accordance with the temperature coefficients of the displacements of the two or more measurement positions different from the reference position on the surface of the at least one distance measuring device with respect to the reference position, and adjusting the position of the objective lens of the confocal optical system based on the thus corrected focus position data of the confocal optical system.

50. A method for producing digital data of a scanner having a confocal optical system in accordance with claim 48 wherein the sample carrier is constituted so as to carry two or more distance measuring devices, and which further comprises steps of reading from the non-volatile memory the position data produced by placing the sample carrier carrying two or more samples on the sample stage, measuring distances between the objective lens incorporated in the confocal optical system and three or more measurement positions different from each other on each of the two or more distance measuring devices, determining one of the measurement positions on one of the two or more distance measuring devices as the reference position, calculating displacements of the measurement positions on each of the two or more distance measuring devices with respect to the reference position, and averaging the displacements of the measurement positions on each of the two or more distance measuring devices and stored in the non-volatile memory, correcting the focus position data of the confocal optical system based on the position data for each of samples set at positions corresponding to positions of the two or more distance measuring devices set in the sample carrier, and moving the objective lens of the confocal optical system in accordance with the thus corrected focus position data of the confocal optical system, thereby adjusting the position of the objective lens.

51. A method for producing digital data of a scanner having a confocal optical system in accordance with claim 49 wherein the sample carrier is constituted so as to carry two or more distance measuring devices, and which further comprises steps of reading from the non-volatile memory the position data produced by placing the sample carrier carrying two or more samples on the sample stage, measuring distances between the objective lens incorporated in the confocal optical system and three or more measurement positions different from each other on each of the two or more distance measuring devices, determining one of the measurement positions on one of the two or more distance measuring devices as the reference position, calculating displacements of the measurement positions on each of the two or more distance measuring devices with respect to the reference position, and averaging the displacements of the measurement positions on each of the two or more distance measuring devices and stored in the non-volatile memory, correcting the focus position data of the confocal optical system based on the position data for each of samples set at positions corresponding to positions of the two or more distance measuring devices set in the sample carrier, and moving the objective lens of the confocal optical system in accordance with the thus corrected focus position data of the confocal optical system, thereby adjusting the position of the objective lens.

52. A method for producing digital data of a scanner having a confocal optical system in accordance with claim 51, which further comprises steps of reading from the non-volatile memory the temperature coefficients of displacements of the measurement positions with respect to the reference position produced by measuring distances between the objective lens incorporated in the confocal optical system and the three or more measurement positions on each of the two or more distance measuring devices with respect to the reference position determined by one of the measurement positions on one of the two or more distance measuring devices at two or more temperatures different from each other, and calculating displacements of the measurement positions on each of the two or more distance measuring devices with respect to the reference position and stored in the non-volatile memory, reading from the non-volatile memory the average temperature in the scanner when the focus position data of the confocal optical system were produced stored in the non-volatile memory, correcting the focus position data of the confocal optical system for each of the two or more distance measuring devices according to difference in temperature between the temperature in the scanner and the average temperature in the scanner when the focus position data of the confocal optical system were produced and in accordance with the temperature coefficients of the two or more distance measuring devices stored in the non-volatile memory, and moving the objective lens of the confocal optical system in accordance with the thus corrected focus position data of the confocal optical system, thereby adjusting the position of the objective lens.

53. A method for producing digital data of a scanner having a confocal optical system in accordance with claim 50 which further comprises steps of reading the position data produced by measuring distances between the objective lens incorporated in the confocal optical system and at least two measurement positions different from each other in each main scanning line on each of the two or more distance measuring devices set in the sample carrier, determining one of the measurement positions on one of the two or more distance measuring devices as the reference position, and calculating displacements of the measurement positions on each of the two or more distance measuring devices with respect to the reference position, averaging the displacements of the measurement positions on each of the two or more distance measuring devices and stored in the non-volatile memory, correcting the focus position data of the confocal optical system read from the non-volatile memory based on the position data for each of the samples set at positions corresponding to positions of the two or more distance measuring devices set in the sample carrier, and moving the objective lens of the confocal optical system in accordance with the thus corrected focus position data of the confocal optical system, thereby adjusting the position of the objective lens.

54. A method for producing digital data of a scanner having a confocal optical system in accordance with claim 51, which further comprises steps of reading the position data produced by measuring distances between the objective lens incorporated in the confocal optical system and at least two measurement positions different from each other in each main scanning line on each of the two or more distance measuring devices set in the sample carrier, determining one of the measurement positions on one of the two or more distance measuring devices as the reference position, and calculating displacements of the measurement positions on each of the two or more distance measuring devices with respect to the reference position, averaging the displacements of the measurement positions on each of the two or more distance measuring devices and stored in the non-volatile memory, correcting the focus position data of the confocal optical system read from the non-volatile memory based on the position data for each of the samples set at positions corresponding to positions of the two or more distance measuring devices set in the sample carrier, and moving the objective lens of the confocal optical system in accordance with the thus corrected focus position data of the confocal optical system, thereby adjusting the position of the objective lens.

55. A method for producing digital data of a scanner having a confocal optical system in accordance with claim 54 which further comprises steps of reading from the non-volatile memory an average value of the temperature coefficients of displacements of the measurement positions on each of the two or more distance measuring devices with respect to the reference position produced by measuring distances between the objective lens incorporated in the confocal optical system and the at least two measurement positions in each main scanning line on each of the two or more distance measuring devices at two or more temperatures different from each other, determining one of the measurement positions on one of the two or more distance measuring devices as the reference position, calculating displacements of the measurement positions on each of the two or more distance measuring devices with respect to the reference position to produce the temperature coefficients of displacements of the measurement positions with respect to the reference position, and averaging the temperature coefficients and stored in the non-volatile memory, reading from the non-volatile memory the average temperature in the scanner when the focus position data were produced stored in the non-volatile memory, correcting the focus position data of the confocal optical system read from the non-volatile memory for each of the two or more distance measuring devices according to difference in temperature between the temperature in the scanner and the average temperature in the scanner when the focus position data of the confocal optical system were produced and in accordance with the temperature coefficients of the two or more distance measuring devices, and moving the objective lens of the confocal optical system in accordance with the thus corrected focus position data of the confocal optical system, thereby adjusting the position of the objective lens.

56. A method for producing digital data of a scanner having a confocal optical system in accordance with claim 53 which further comprises steps of reading the position data produced by measuring distances between the objective lens incorporated in the confocal optical system and three measurement positions different from each other in each main scanning line on each of the two or more distance measuring devices set in the sample carrier, determining one of the measurement positions on one of the two or more distance measuring devices as the reference position, calculating displacements of the measurement positions on each of the two or more distance measuring devices with respect to the reference position, and averaging the displacements of the measurement positions on each of the two or more distance measuring devices and stored in the non-volatile memory, correcting the focus position data of the confocal optical system read from the non-volatile memory based on the position data for each of the samples set at positions corresponding to positions of the two or more distance measuring devices set in the sample carrier, and moving the objective lens of the confocal optical system in accordance with the thus corrected focus position data of the confocal optical system, thereby adjusting the position of the objective lens.

57. A method for producing digital data of a scanner having a confocal optical system in accordance with claim 54 which further comprises steps of reading the position data produced by measuring distances between the objective lens incorporated in the confocal optical system and three measurement positions different from each other in each main scanning line on each of the two or more distance measuring devices set in the sample carrier, determining one of the measurement positions on one of the two or more distance measuring devices as the reference position, calculating displacements of the measurement positions on each of the two or more distance measuring devices with respect to the reference position, and averaging the displacements of the measurement positions on each of the two or more distance measuring devices and stored in the non-volatile memory, correcting the focus position data of the confocal optical system read from the non-volatile memory based on the position data for each of the samples set at positions corresponding to positions of the two or more distance measuring devices set in the sample carrier, and moving the objective lens of the confocal optical system in accordance with the thus corrected focus position data of the confocal optical system, thereby adjusting the position of the objective lens.

58. A method for producing digital data of a scanner having a confocal optical system in accordance with claim 57 which further comprises steps of reading from the non-volatile memory an average value of the temperature coefficients of displacements of the measurement positions on each of the two or more distance measuring devices with respect to the reference position produced as temperature coefficients of the two or more distance measuring devices by measuring distances between the objective lens incorporated in the confocal optical system and the three measurement positions in each main scanning line on each of the two or more distance measuring devices at two or more temperatures different from each other, determining one of the measurement positions on one of the two or more distance measuring devices as the reference position, calculating displacements of the measurement positions on each of the two or more distance measuring devices with respect to the reference position to produce the temperature coefficients of displacements of the measurement positions with respect to the reference position, and averaging the temperature coefficients and stored in the non-volatile memory, reading from the non-volatile memory the average temperature in the scanner when the focus position data were produced stored in the non-volatile memory, correcting the focus position data of the confocal optical system read from the non-volatile memory for each of the two or more distance measuring devices according to difference in temperature between the temperature in the scanner and the average temperature in the scanner when the focus position data of the confocal optical system were produced and in accordance with the temperature coefficients of the two or more distance measuring devices, and moving the objective lens of the confocal optical system in accordance with the thus corrected focus position data of the confocal optical system, thereby adjusting the position of the objective lens.

59. A method for producing digital data of a scanner having a confocal optical system in accordance with claim 52 which further comprises steps of reading from the non-volatile memory the position data produced by averaging displacements of the measurement positions with respect to the reference position for every predetermined number of the main scanning lines on each of the two or more distance measuring devices, correcting the focus position data of the confocal optical system read from the non-volatile memory based on the position data for every predetermined number of the main scanning lines corresponding to the predetermined number of the main scanning lines on each of the samples set at positions in the sample carrier corresponding to positions where the two or more distance measuring devices are set, and moving the objective lens of the confocal optical system in accordance with the thus corrected focus position data of the confocal optical system, thereby adjusting the position of the objective lens.

60. A method for producing digital data of a scanner having a confocal optical system in accordance with claim 59 which further comprises steps of reading from the non-volatile memory an average value of the temperature coefficients of displacements of the measurement positions on each of the two or more distance measuring devices with respect to the reference position produced by measuring distances between the objective lens incorporated in the confocal optical system and three measurement positions in each main scanning line for each predetermined number of main scanning lines on each of the two or more distance measuring devices at two or more temperatures different from each other, determining one of the measurement positions on one of the two or more distance measuring devices as the reference position, calculating displacements of the measurement positions with respect to the reference position for every predetermined number of the main scanning lines on each of the two or more distance measuring devices to produce the temperature coefficients of displacements of the measurement positions with respect to the reference position, averaging the temperature coefficients of displacements of the measurement positions with respect to the reference position and stored in the non-volatile memory as temperature coefficients for every predetermined number of the main scanning lines on each of the two or more distance measuring devices, reading from the non-volatile memory the average temperature in the scanner when the focus position data were produced stored in the non-volatile memory, correcting the focus position data of the confocal optical system read from the non-volatile memory according to difference in temperature between the temperature in the scanner and the average temperature in the scanner when the focus position data of the confocal optical system were produced and in accordance with the temperature coefficients for every predetermined number of the main scanning lines on each of the two or more distance measuring devices for every predetermined number of the main scanning lines corresponding to the predetermined number of the main scanning lines on each of the samples set at positions in the sample carrier corresponding to positions where the two or more distance measuring devices are set, and moving the objective lens of the confocal optical system in accordance with the thus corrected focus position data of the confocal optical system, thereby adjusting the position of the objective lens.

61. A method for producing digital data of a scanner having a confocal optical system in accordance with claim 46 which further comprises steps of reading from the non-volatile memory coefficients of an nth order function produced by plotting integrated values of signal intensity of fluorescence emission or photoluminescence emission and fitting the plotted values with the nth order function and stored in the non-volatile memory, reading from the non-volatile memory displacements of measurement positions on the at least one distance measuring device with respect to the reference position stored in the non-volatile memory, producing shading correction data for correcting shading of digital data of the at least one sample based on the coefficients of the nth order function and the displacements of measurement positions on the at least one distance measuring device with respect to the reference position, and correcting digital data of the at least one sample based on the shading correction data.

62. A method for producing digital data of a scanner having a confocal optical system in accordance with claim 46 which further comprises steps of setting a shading estimation device in which a mask of metal is formed on a support having a property to release fluorescence emission upon being irradiated with a laser beam and capable of being processed while retaining optical flatness, thereby regularly forming a plurality of openings through which the support is exposed in the sample carrier, placing the sample carrier on the sample stage, scanning the shading estimation device with the laser beam via the openings to stimulate the support at the plurality of openings, photoelectrically detecting fluorescence emission released from the support via the plurality of openings to produce analog data, digitizing the analog data, producing digital data of the shading estimation device based on the thus produced digital data, producing shading correction data based on the digital data of the shading estimation device, storing the thus produced shading correction data in the non-volatile memory or the memory of the scanner, and reading the shading correction data to correct digital data of the at least one samples therewith.

63. A method for producing digital data of a scanner having a confocal optical system in accordance with claim 62 which further comprises steps of adjusting a focus of the confocal optical system to the opening located at the reference position among the plurality of openings regularly formed in the shading estimation device, scanning the shading estimation device with the laser beam via the plurality of openings, stimulating the support via the plurality of openings, photoelectrically detecting fluorescence emission released from the support to produce analog data, digitizing the analog data to produce digital data of the shading estimation device, producing the shading correction data based on the digital data of the shading estimation device, and storing the thus produced shading correction data in the non-volatile memory or the memory of the scanner.

* * * * *